US010767169B1

(12) United States Patent
Kim et al.

(10) Patent No.: US 10,767,169 B1
(45) Date of Patent: Sep. 8, 2020

(54) NUCLEIC ACID-GUIDED NUCLEASES

(71) Applicant: Inscripta, Inc., Boulder, CO (US)

(72) Inventors: Juhan Kim, Boulder, CO (US); Benjamin Mijts, Boulder, CO (US); Aamir Mir, Boulder, CO (US); Andrew Garst, Boulder, CO (US); Kyle Seamon, Boulder, CO (US)

(73) Assignee: Inscripta, Inc., Boulder, CO (US)

( * ) Notice: Subject to any disclaimer, the term of this patent is extended or adjusted under 35 U.S.C. 154(b) by 0 days.

(21) Appl. No.: 16/928,742

(22) Filed: Jul. 14, 2020

Related U.S. Application Data

(63) Continuation of application No. 16/868,472, filed on May 6, 2020, now Pat. No. 10,724,021, which is a continuation of application No. 16/714,320, filed on Dec. 13, 2019, now Pat. No. 10,704,033.

(51) Int. Cl.

| | |
|---|---|
| ***C12N 9/22*** | (2006.01) |
| ***C12N 15/90*** | (2006.01) |
| ***C12N 15/85*** | (2006.01) |
| ***C12N 15/74*** | (2006.01) |
| ***C12N 15/81*** | (2006.01) |
| ***C12N 15/10*** | (2006.01) |

(52) U.S. Cl.
CPC ............. *C12N 9/22* (2013.01); *C12N 15/102* (2013.01); *C12N 15/74* (2013.01); *C12N 15/81* (2013.01); *C12N 15/85* (2013.01); *C12N 15/905* (2013.01); *C12N 15/907* (2013.01); *C12N 2310/531* (2013.01)

(58) Field of Classification Search
CPC ...... C12N 9/22; C12N 15/905; C12N 15/102; C12N 15/907; C12N 15/81; C12N 15/85; C12N 15/74; C12N 2310/531
See application file for complete search history.

*Primary Examiner* — Ganapathirama Raghu

(74) *Attorney, Agent, or Firm* — Sarah Brashears; Dianna L. DeVore

(57) ABSTRACT

The present disclosure provides novel RNA-guided enzymes for making rational and direct edits to the genome of live cells.

12 Claims, 6 Drawing Sheets

Specification includes a Sequence Listing.

SEQUENCE LISTING

<160> NUMBER OF SEQ ID NOS: 52

<210> SEQ ID NO 1
<211> LENGTH: 3792
<212> TYPE: DNA
<213> ORGANISM: Eubacterium rectale

<400> SEQUENCE: 1
atgaacaacg gcacaaataa ttttcagaac ttcatcggga tctcaagttt gcagaaaacg 60
ctgcgcaatg ctctgatccc cacggaaacc acgcaacagt tcatcgtcaa gaacggaata 120
attaaagaag atgagttacg tggcgagaac cgccagattc tgaaagatat catggatgac 180
tactaccgcg gattcatctc tgagactctg agttctattg atgacataga ttggactagc 240
ctgttcgaaa aaatggaaat tcagctgaaa aatggtgata ataaagatac cttaattaag 300
gaacagacag agtatcggaa agcaatccat aaaaaatttg cgaacgacga tcggtttaag 360
aacatgttta gcgccaaact gattagtgac atattacctg aatttgtcat ccacaacaat 420
aattattcgg catcagagaa agaggaaaaa acccaggtga taaaattgtt ttcgcgcttt 480
gcgactagct ttaaagatta cttcaagaac cgtgcaaatt gcttttcagc ggacgatatt 540
tcatcaagca gctgccatcg catcgtcaac gacaatgcag agatattctt ttcaaatgcg 600
ctggtctacc gccggatcgt aaaatcgctg agcaatgacg atatcaacaa aatttcgggc 660

-continued

```
gatatgaaag attcattaaa agaaatgagt ctggaagaaa tatattctta cgagaagtat    720

ggggaattta ttacccagga aggcattagc ttctataatg atatctgtgg gaaagtgaat    780

tcttttatga acctgtattg tcagaaaaat aaagaaaaca aaaatttata caaacttcag    840

aaacttcaca aacagattct atgcattgcg gacactagct atgaggtccc gtataaattt    900

gaaagtgacg aggaagtgta ccaatcagtt aacggcttcc ttgataacat tagcagcaaa    960

catatagtcg aaagattacg caaaatcggc gataactata acggctacaa cctggataaa   1020

atttatatcg tgtccaaatt ttacgagagc gttagccaaa aaacctaccg cgactgggaa   1080

acaattaata ccgccctcga aattcattac aataatatct tgccgggtaa cggtaaaagt   1140

aaagccgaca aagtaaaaaa agcggttaag aatgatttac agaaatccat caccgaaata   1200

aatgaactag tgtcaaacta taagctgtgc agtgacgaca acatcaaagc ggagacttat   1260

atacatgaga ttagccatat cttgaataac tttgaagcac aggaattgaa atacaatccg   1320

gaaattcacc tagttgaatc cgagctcaaa gcgagtgagc ttaaaaacgt gctggacgtg   1380

atcatgaatg cgtttcattg gtgttcggtt tttatgactg aggaacttgt tgataaagac   1440

aacaattttt atgcggaact ggaggagatt tacgatgaaa tttatccagt aattagtctg   1500

tacaacctgg ttcgtaacta cgttacccag aaaccgtaca gcacgaaaaa gattaaattg   1560

aactttggaa taccgacgtt agcagacggt tggtcaaagt ccaaagagta ttctaataac   1620

gctatcatac tgatgcgcga caatctgtat tatctgggca tctttaatgc gaagaataaa   1680

ccggacaaga agattatcga gggtaatacg tcagaaaata agggtgacta caaaaagatg   1740

atttataatt tgctcccggg tcccaacaaa atgatcccga aagttttctt gagcagcaag   1800

acgggggtgg aaacgtataa accgagcgcc tatatcctag aggggtataa acagaataaa   1860

catatcaagt cttcaaaaga ctttgatatc actttctgtc atgatctgat cgactacttc   1920

aaaaactgta ttgcaattca tcccgagtgg aaaaacttcg gttttgattt tagcgacacc   1980

agtacttatg aagacatttc cgggttttat cgtgaggtag agttacaagg ttacaagatt   2040

gattggacat acattagcga aaaagacatt gatctgctgc aggaaaaagg tcaactgtat   2100

ctgttccaga tatataacaa agatttttcg aaaaaatcaa ccgggaatga caaccttcac   2160

accatgtacc tgaaaaatct tttctcagaa gaaaatctta aggatatcgt cctgaaactt   2220

aacggcgaag cggaaatctt cttcaggaag agcagcataa agaacccaat cattcataaa   2280

aaaggctcga ttttagtcaa ccgtacctac gaagcagaag aaaaagacca gtttggcaac   2340

attcaaattg tgcgtaaaaa tattccggaa aacatttatc aggagctgta caaatacttc   2400

aacgataaaa gcgacaaaga gctgtctgat gaagcagcca aactgaagaa tgtagtggga   2460

caccacgagg cagcgacgaa tatagtcaag gactatcgct acacgtatga taaatacttc   2520

cttcatatgc ctattacgat caatttcaaa gccaataaaa cgggttttat taatgatagg   2580

atcttacagt atatcgctaa agaaaaagac ttacatgtga tcggcattga tcggggcgag   2640

cgtaacctga tctacgtgtc cgtgattgat acttgtggta atatagttga acagaaaagc   2700

tttaacattg taaacggcta cgactatcag ataaaactga aacaacagga gggcgctaga   2760

cagattgcgc ggaaagaatg gaaagaaatt ggtaaaatta aagagatcaa agagggctac   2820

ctgagcttag taatccacga gatctctaaa atggtaatca aatacaatgc aattatagcg   2880

atggaggatt tgtcttatgg ttttaaaaaa gggcgcttta aggtcgaacg gcaagtttac   2940

cagaaatttg aaaccatgct catcaataaa ctcaactatc tggtatttaa agatatttcg   3000

attaccgaga atggcggtct cctgaaaggt tatcagctga catacattcc tgataaactt   3060
```

```
aaaaacgtgg gtcatcagtg cggctgcatt ttttatgtgc ctgctgcata cacgagcaaa   3120

attgatccga ccaccggctt tgtgaatatc tttaaattta aagacctgac agtggacgca   3180

aaacgtgaat tcattaaaaa atttgactca attcgttatg acagtgaaaa aaatctgttc   3240

tgctttacat ttgactacaa taactttatt acgcaaaaca cggtcatgag caaatcatcg   3300

tggagtgtgt atacatacgg cgtgcgcatc aaacgtcgct ttgtgaacgg ccgcttctca   3360

aacgaaagtg ataccattga cataaccaaa gatatggaga aaacgttgga aatgacggac   3420

attaactggc gcgatggcca cgatcttcgt caagacatta tagattatga aattgttcag   3480

cacatattcg aaattttccg tttaacagtg caaatgcgta actccttgtc tgaactggag   3540

gaccgtgatt acgatcgtct catttcacct gtactgaacg aaaataacat tttttatgac   3600

agcgcgaaag cgggggatgc acttcctaag gatgccgatg caaatggtgc gtattgtatt   3660

gcattaaaag ggttatatga aattaaacaa attaccgaaa attggaaaga agatggtaaa   3720

ttttcgcgcg ataaactcaa aatcagcaat aaagattggt tcgactttat ccagaataag   3780

cgctatctct aa                                                       3792
```

```
<210> SEQ ID NO 2
<211> LENGTH: 3792
<212> TYPE: DNA
<213> ORGANISM: Artificial Sequence
<220> FEATURE:
<223> OTHER INFORMATION: Human codon-optimized MAD7

<400> SEQUENCE: 2

atgaataatg gcactaacaa ctttcagaat ttcataggca tcagtagtct ccaaaagacg     60

ttgcgcaacg cacttattcc aaccgagaca actcaacagt tcatcgtgaa gaatgggatt    120

attaaagagg acgaactccg aggagagaac cggcaaattc ttaaggacat catggacgat    180

tattacagag ggtttatttc tgagacatta tcaagtattg acgacatcga ctggacctca    240

ctgttcgaga agatggaaat tcagttgaag aacggagaca acaaggacac tctaatcaag    300

gaacaaacag agtaccggaa agctatacat aagaagtttg ccaatgatga ccggtttaag    360

aacatgttct ccgcgaaact catcagcgac attctgccag aattcgtgat ccacaacaat    420

aactattcag cctctgagaa ggaggaaaag acccaggtca tcaagctttt ctctagattc    480

gccactagct tcaaggacta tttcaagaac cgcgccaatt gtttctctgc tgacgatatc    540

tccagcagca gttgccatag gatcgtgaac gacaatgctg aaatcttctt ctctaatgcc    600

cttgtataca gacggatcgt gaagtcactg agcaatgatg acattaacaa gataagcggt    660

gatatgaaag atagtctcaa ggaaatgtca ctcgaagaaa tttatagcta cgagaaatac    720

ggagagttca tcacccagga gggaatcagt ttctacaacg atatttgtgg caaggtaaac    780

tccttcatga atctatattg ccagaaaaac aaggagaata agaatcttta taagctgcag    840

aagttacata agcagatcct gtgtattgca gatacctcct atgaagtgcc atataagttt    900

gagtctgacg aggaagtgta tcaatccgta aatgggttcc tcgacaacat cagctctaag    960

catatagttg aacgacttag aaagataggc gacaactata atggctacaa cctcgacaag   1020

atttatatag tgtccaaatt ctacgagtcc gtatcccaaa agacatacag agattgggaa   1080

acaatcaata cagccctcga aatccactac aataatatcc tacccggcaa tgggaaatcc   1140

aaggcagata aggtaaagaa ggcagtcaag aacgacctcc agaagtccat caccgagatt   1200

aacgaactgg tgagcaatta caaactctgt agtgacgata atatcaaggc tgagacgtac   1260
```

-continued

```
atccatgaga tttcacacat attgaacaac ttcgaagcac aggaactgaa gtacaatccg   1320
gaaattcatc tcgtagaatc cgagcttaaa gccagcgagc ttaagaacgt gctcgatgtg   1380
attatgaacg cgtttcactg gtgtagtgtc ttcatgactg aagaattagt tgacaaggac   1440
aacaatttct atgccgaact ggaagaaatt tacgatgaga tctatcctgt tatcagtctg   1500
tataacctcg tacggaacta tgtgacccag aagccctact cgaccaaaaa gatcaaactg   1560
aacttcggca ttccaaccct ggccgatgga tggagcaaat ccaaagagta ctctaataac   1620
gctatcattc tcatgcgaga caatctctac tatctcggaa tattcaatgc aaagaataaa   1680
ccagacaaaa agattattga agggaacaca tccgagaaca aaggtgatta taagaaaatg   1740
atttacaacc tgcttccagg gcccaataag atgattccca aggtctttct ttcaagcaag   1800
actggagttg agacttacaa gccgtccgca tacattctcg agggctataa gcagaacaag   1860
cacattaaga gcagtaaaga cttcgatatc actttctgcc atgatctcat tgactacttt   1920
aagaattgta tcgctattca tccggaatgg aagaactttg gatttgactt cagcgataca   1980
agtacctacg aggatatctc tgggttctac cgggaagtgg aacttcaggg atacaagatc   2040
gactggacat atatctctga gaaagacatc gatctgctgc aggagaaagg ccagctgtac   2100
ctgttccaga tttataataa agatttctca aagaagagca caggaaacga taatcttcat   2160
actatgtatc tgaagaatct cttctccgaa gagaacctga aggatatcgt cctcaaactg   2220
aacggagaag ccgagatttt cttcaggaag agtagtatta agaatcccat tattcataag   2280
aaaggctcca tcttggttaa ccgcacttac gaggctgaag agaaggacca gtttggaaat   2340
atccaaatcg tgaggaagaa tattccagag aatatctacc aggaactgta taagtacttt   2400
aatgataaga gcgataaaga actgagcgac gaggcagcga agttgaagaa tgtggtgggc   2460
catcacgaag ctgccacaaa cattgtgaaa gactataggt acacatatga taaatacttt   2520
ctgcatatgc ctataaccat aaatttcaag gccaataaga ctgggttcat taatgaccgc   2580
atcctgcagt acatcgctaa ggagaaggac ctgcacgtca tagggatcga ccgcggtgaa   2640
cggaatttga tttatgtgtc cgttatcgat acctgcggga atatcgtgga gcaaaagagc   2700
tttaatatcg tcaatggata cgactaccag atcaagttaa agcagcaaga aggcgccagg   2760
caaatcgcca ggaaagagtg gaaagagatc ggcaagataa aggaaattaa ggaaggctac   2820
ctttccctgg tcatccatga aattagtaag atggtcatta agtacaatgc catcatagca   2880
atggaagact taagttacgg atttaagaag ggaagattca aagtggaaag gcaggtgtat   2940
cagaagtttg aaacgatgct aataaacaaa cttaattatc ttgtgttcaa agacattagc   3000
atcacagaga atggagggct tctcaaggga taccaactga cctacatccc agataagctt   3060
aagaacgttg gccaccaatg cggctgcata ttctacgtcc cggctgctta cacttctaag   3120
atcgatccaa ccaccggctt tgtgaatatc tttaagttta aagacttgac cgtggatgct   3180
aagcgcgagt tcatcaagaa gtttgacagc atcaggtacg actcagaaaa gaacctcttc   3240
tgtttcacat tcgattataa caactttatt actcagaata ctgtcatgag taagtcatcc   3300
tggtcagtgt atacctacgg agtgaggatc aagcgaaggt ttgtgaacgg caggtttagt   3360
aatgagtctg acacaatcga tattaccaaa gacatggaga aaacactgga gatgacagac   3420
atcaactgga gggatggaca tgacctgcgc caggatatca tagattacga gatcgtgcaa   3480
catatattcg aaatctttag gctgacagtg cagatgcgca actccctgag cgagctcgaa   3540
gacagagatt atgatagact aatcagtccg gttctgaacg agaacaatat cttctacgat   3600
agtgctaagg caggagacgc gctgcccaag gacgcagatg ccaatggcgc gtattgcatt   3660
```

```
gcacttaaag gactgtacga aattaagcag attaccgaga actggaagga ggacggcaag   3720

tttagcaggg ataagctgaa gattagtaac aaagattggt ttgactttat acagaataag   3780

cgttatctgt aa                                                       3792
```

```
<210> SEQ ID NO 3
<211> LENGTH: 3792
<212> TYPE: DNA
<213> ORGANISM: Artificial Sequence
<220> FEATURE:
<223> OTHER INFORMATION: Variant MAD7 nucleic acid sequence

<400> SEQUENCE: 3

atgaacaacg gcacaaataa ttttcagaac ttcatcggga tctcaagttt gcagaaaacg     60

ctgcgcaatg ctctgatccc cacggaaacc acgcaacagt tcatcgtcaa gaacggaata    120

attaaagaag atgagttacg tggcaaaaac cgccagattc tgaaagatat catggatgac    180

tactaccgcg gattcatctc tgagactctg agttctattg atgacataga ttggactagc    240

ctgttcgaaa aaatggaaat tcagctgaaa aatggtgata ataaagatac cttaattaag    300

gaacaggcgg agaaacggaa agcaatctat aaaaaatttg cggatgacga tcggtttaag    360

aacatgttta gcgccaaact gattagtgac atattacctg aatttgtcat ccacaacaat    420

aattattcgg catcagagaa aaaagaaaaa acccaggtga taaaattgtt ttcgcgcttt    480

gcgactagct ttaaagatta cttcaagaac cgtgcaaatt gcttttcagc ggacgatatt    540

tcatcaagca gctgccatcg catcgtcaac gacaatgcag agatattctt ttcaaatgcg    600

ctggtctacc gccggatcgt aaaaaacctg agcaatgacg atatcaacaa aatttcgggc    660

gatatgaaag attcattaaa agaaatgagt ctggaagaaa tatattctta cgagaagtat    720

ggggaattta ttacccagga aggcattagc ttctataatg atatctgtgg gaaagtgaat    780

tcttttatga acctgtattg tcagaaaaat aaagaaaaca aaaatttata caaacttcgt    840

aaacttcaca aacagattct atgcattgcg gacactagct atgaggtccc gtataaattt    900

gaaagtgacg aggaagtgta ccaatcagtt aacggcttcc ttgataacat tagcagcaaa    960

catatagtcg aaagattacg caaaatcggc gataactata acgattacaa cctggataaa   1020

atttatatcg tgtccaaatt ttacgagagc gttagccaaa aaacctaccg cgactgggaa   1080

acaattaata ccgccctcga aattcattac aataatatct tgccgggtaa cggtaaaagt   1140

aaagccgaca aagtaaaaaa agcggttaag aatgatttac agaaatccat caccgaaata   1200

aatgaactag tgtcaaacta taagctgtgc agtgacgaca acatcaaagc ggagacttat   1260

atacatgaga ttagccatat cttgaataac tttgaagcac atgaattgaa atacaatccg   1320

gaaattcacc tagttgaatc cgagctcaaa gcgagtgagc ttaaaaacgt gctggacatt   1380

atcatgaatg cgtttcattg gtgttcggtt tttatgactg aggaacttgt tgataaagac   1440

aacaattttt atgcggaact ggaggagatt tacgatgaaa tttatccagt aattagtctg   1500

tacaacctgg ttcgtaacta cgttacccag aaaccgtaca gcacgaaaaa gattaaattg   1560

aactttggaa taccgacgtt agcagacggt tggtcaaagt ccaaagagta ttctaataac   1620

gctatcatac tgatgcgcga caatctgtat tatctgggca tctttaatgc gaagaataaa   1680

ccggacaaga agattatcga gggtaatacg tcagaaaata agggtgacta caaaaagatg   1740

atttataatt tgctcccggg tcccaacaaa atgatcccga aagttttctt gagcagcaag   1800

acgggggtgg aaacgtataa accgagcgcc tatatcctag aggggtataa acagaataaa   1860
```

```
catctgaagt cttcaaaaga ctttgatatc actttctgtc atgatctgat cgactacttc   1920

aaaaactgta ttgcaattca tcccgagtgg aaaaacttcg gttttgattt tagcgacacc   1980

agtgcgtatg aagacatttc cgggttttat cgtgaggtag agttacaagg ttacaagatt   2040

gattggacat acattagcga aaaagacatt gatctgctgc aggaaaaagg tcaactgtat   2100

ctgttccaga tatataacaa agatttttcg aaaaaatcaa ccgggaatga caaccttcac   2160

accatgtacc tgaaaaatct tttctcagaa gaaaatctta aggatatcgt cctgaaactt   2220

aacggcgaag cggaaatctt cttcaggaag agcagcataa agaacccaat cattcataaa   2280

aaaggctcga ttttagtcaa ccgtacctac gaagcagaag aaaaagacca gtttggcaac   2340

attcaaattg tgcgtaaaac cattccggaa aacatttatc aggagctgta caaatacttc   2400

aacgataaaa gcgacaaaga gctgtctgat gaagcagcca aactgaagaa tgtagtggga   2460

caccacgagg cagcgacgaa tatagtcaag gactatcgct acacgtatga taaatacttc   2520

cttcatatgc ctattacgat caatttcaaa gccaataaaa cgagctttat taatgatagg   2580

atcttacagt atatcgctaa agaaaaagac ttacatgtga tcggcattga tcggggcgag   2640

cgtaacctga tctacgtgtc cgtgattgat acttgtggta atatagttga acagaaaagc   2700

tttaacattg taaacggcta cgactatcag ataaaactga aacaacagga gggcgctaga   2760

cagattgcgc ggaaagaatg gaaagaaatt ggtaaaatta aagagatcaa agagggctac   2820

ctgagcttag taatccacga gatctctaaa atggtaatca aatacaatgc aattatagcg   2880

atggaggatt tgtcttatgg ttttaaaaaa gggcgcttta aggtcgaacg gcaagtttac   2940

cagaaatttg aaaccatgct catcaataaa ctcaactatc tggtatttaa agatatttcg   3000

attaccgaga atggcggtct cctgaaaggt tatcagctga catacattcc tgataaactt   3060

aaaaacgtgg gtcatcagtg cggctgcatt ttttatgtgc ctgctgcata cacgagcaaa   3120

attgatccga ccaccggctt tgtgaatatc tttaaattta aagacctgac agtggacgca   3180

aaacgtgaat tcattaaaaa atttgactca attcgttatg acagtgaaaa aaatctgttc   3240

tgctttacat ttgactacaa taactttatt acgcaaaaca cggtcatgag caaatcatcg   3300

tggagtgtgt atacatacgg cgtgcgcatc aaacgtcgct ttgtgaacgg ccgcttctca   3360

aacgaaagtg ataccattga cataaccaaa gatatggaga aaacgttgga aatgacggac   3420

attaactggc gcgatggcca cgatcttcgt caagacatta tagattatga aattgttcag   3480

cacatattcg aaattttcaa attaacagtg caaatgcgta actccttgtc tgaactggag   3540

gaccgtgatt acgatcgtct catttcacct gtactgaacg aaaataacat tttttatgac   3600

agcgcgaaag cggggtatgc acttcctaag gatgccgatg caaatggtgc gtattgtatt   3660

gcattaaaag ggttatatga aattaaacaa attaccgaaa attggaaaga agatggtaaa   3720

ttttcgcgcg ataaactcaa aatcagcaat aaagattggt tcgactttat ccagaataag   3780

cgctatctct aa                                                       3792
```

```
<210> SEQ ID NO 4
<211> LENGTH: 3792
<212> TYPE: DNA
<213> ORGANISM: Artificial Sequence
<220> FEATURE:
<223> OTHER INFORMATION: Modified MAD7 nucleic acid sequence

<400> SEQUENCE: 4

atgaacaacg gcacaaataa ttttcagaac ttcatcggga tctcaagttt gcagaaaacg     60

ctgcgcaatg ctctgacccc cacggaaacc acgcaacagt tcatcgtcaa gaacggaata    120
```

```
attaaagaag atgagttacg tggcgagaac cgccagattc tgaaagatat catggatgac    180
tactaccgcg gattcatctc tgagactctg agttctattg atgacataga ttggactagc    240
ctgttcgaaa aaatggaaat tcagctgaaa aatggtgata ataaagatac cttaattaag    300
gaacaggcgg agaaacggaa agcaatctat aaaaaatttg cggatgacga tcggtttaag    360
aacatgttta gcgccaaact gattagtgac atattacctg aatttgtcat ccacaacaat    420
aattattcgg catcagagaa agaggaaaaa acccaggtga taaaattgtt ttcgcgcttt    480
gcgactagct ttaaagatta cttcaagaac cgtgcaaatt gcttttcagc ggacgatatt    540
tcatcaagca gctgccatcg catcgtcaac gacaatgcag agatattctt ttcaaatgcg    600
ctggtctacc gccggatcgt aaaaaacctg agcaatgacg atatcaacaa aatttcgggc    660
gatatgaaag attcattaaa aaaaatgagt ctggaaaaaa tatattctta cgagaagtat    720
ggggaattta ttacccagga aggcattagc ttctataatg atatctgtgg gaaagtgaat    780
tcttttatga acctgtattg tcagaaaaat aaagaaaaca aaaatttata caaacttcgt    840
aaacttcaca aacagattct atgcattgcg gacactagct atgaggtccc gtataaattt    900
gaaagtgacg aggaagtgta ccaatcagtt aacggcttcc ttgataacat tagcagcaaa    960
catatagtcg aaagattacg caaaatcggc gataactata acggctacaa cctggataaa   1020
atttatatcg tgtccaaatt ttacgagagc gttagccaaa aaacctaccg cgactgggaa   1080
acaattaata ccgccctcga aattcattac aataaatatct tgccgggtaa cggtaaaagt  1140
aaagccgaca aagtaaaaaa agcggttaag aatgatttac agaaatccat caccgaaata   1200
aatgaactag tgtcaaacta taagctgtgc ccggacgaca acatcaaagc ggagacttat   1260
atacatgaga ttagccatat cttgaataac tttgaagcac aggaattgaa atacaatccg   1320
gaaattcacc tagttgaatc cgagctcaaa gcgagtgagc ttaaaaacgt gctggacgtg   1380
atcatgaatg cgtttcattg gtgttcggtt tttatgactg aggaacttgt tgataaagac   1440
aacaattttt atgcggaact ggaggagatt tacgatgaaa tttatccagt aattagtctg   1500
tacaacctgg ttcgtaacta cgttacccag aaaccgtaca gcacgaaaaa gattaaattg   1560
aactttggaa taccgacgtt agcagacggt tggtcaaagt ccaaagagta ttctaataac   1620
gctatcatac tgatgcgcga caatctgtat tatctgggca tctttaatgc gaagaataaa   1680
ccggaaaaga agattatcga gggtaatacg tcagaaaata agggtgacta caaaaagatg   1740
atttataatt tgctcccggg tcccaacaaa atgatcccga aagttttctt gagcagcaag   1800
acgggggtgg aaacgtataa accgagcgcc tatatcctag aggggtataa acagaataaa   1860
catctgaagt cttcaaaaga ctttgatatc actttctgtc gtgatctgat cgactacttc   1920
aaaaactgta ttgcaattca tcccgagtgg aaaaacttcg gttttgattt tagcgacacc   1980
agtacttatg aagacatttc cgggttttat cgtgaggtag agttacaagg ttacaagatt   2040
gattggacat acattagcga aaaagacatt gatctgctgc aggaaaaagg tcaactgtat   2100
ctgttccaga tatataacaa agatttttcg aaaaaatcaa ccgggaatga caaccttcac   2160
accatgtacc tgaaaaatct tttctcagaa gaaaatctta aggatgtggt cctgaaactt   2220
aacggcgaag cggaaatctt cttcaggaag agcagcataa agaacccaat cattcataaa   2280
aaaggctcga ttttagtcaa ccgtacctac gaagcagaag aaaaagacca gtttggcaac   2340
attcaaattg tgcgtaaaac cattccggaa aacatttatc aggagctgta caaatacttc   2400
aacgataaaa gcgacaaaga gctgtctgat gaagcagcca aactgaagaa tgcggtggga   2460
```

```
caccacgagg cagcgacgaa tatagtcaag gactatcgct acacgtatga taaatacttc   2520
cttcatatgc ctattacgat caatttcaaa gccaataaaa cgagctttat taatgatagg   2580
atcttacagt atatcgctaa agaaaaagac ttacatgtga tcggcattga tcggggcgag   2640
cgtaacctga tctacgtgtc cgtgattgat acttgtggta atatagttga acagaaaagc   2700
tttaacattg taaacggcta cgactatcag ataaaactga aacaacagga gggcgctaga   2760
cagattgcgc ggaaagaatg gaaagaaatt ggtaaaatta aagagatcaa agagggctac   2820
ctgagcttag taatccacga gatctctaaa atggtaatca aatacaatgc aattatagcg   2880
atggaggatt tgtcttatgg ttttaaaaaa gggcgcttta aggtcgaacg gcaagtttac   2940
cagaaatttg aaaccatgct catcaataaa ctcaactatc tggtatttaa agatatttcg   3000
attaccgaga atggcggtct cctgaaaggt tatcagctga catacattcc tgaaaaactt   3060
aaaaacgtgg gtcatcagtg cggctgcatt ttttatgtgc ctgctgcata cacgagcaaa   3120
attgatccga ccaccggctt tgtgaatatc tttaaattta aagacctgac agtggacgca   3180
aaacgtgaat tcattaaaaa atttgactca attcgttatg acagtgataa aaatctgttc   3240
tgctttacat ttgactacaa taactttatt acgcaaaaca cggtcatgag caaatcatcg   3300
tggagtgtgt atacatacgg cgtgcgcatc aaacgtcgct ttgtgaacgg ccgcttctca   3360
aacgaaagtg ataccattga cataaccaaa gatatggaga aaacgttgga aatgacggac   3420
attaactggc gcgatggcca cgatcttcgt caagacatta tagattatga aattgttcag   3480
cacatattcg aaattttcaa attaacagtg caaatgcgta actccttgtc tgaactggag   3540
gaccgtaact acgatcgtct catttcacct gtactgaacg aaaataacat tttttatgac   3600
agcgcgaaag cgggggatgc acttcctaag gatgccgatg caaatggtgc gtattgtatt   3660
gcattaaaag ggttatatga aattaaacaa attaccgaaa attggaaaga agatggtaaa   3720
ttttcgcgcg ataaactcaa aatcagcaat aaagattggt tcgactttat ccagaataag   3780
cgctatctct aa                                                       3792
```

```
<210> SEQ ID NO 5
<211> LENGTH: 3792
<212> TYPE: DNA
<213> ORGANISM: Artificial Sequence
<220> FEATURE:
<223> OTHER INFORMATION: Modified MAD7 nucleic acid sequence

<400> SEQUENCE: 5

atgaacaacg gcacaaataa ttttcagaac ttcatcggga tctcaagttt gcagaaaacg     60
ctgcgcaatg ctctgatccc cacggaaacc acgcaacagt tcatcgtcaa gaacggaata    120
attaaagaag atgagttacg tggcgagaac cgccagattc tgaaagatat catggatgac    180
tactaccgcg gattcatctc tgagactctg agttctattg atgacataga ttggactagc    240
ctgttcgaaa aaatggaaat tcagctgaaa aatggtgata ataaagatac cttaattaag    300
gaacaggcgg agaaacggaa agcaatctat aaaaaatttg cggatgacga tcggtttaag    360
aacatgttta gcgccaaact gattagtgac atattacctg aatttgtcat ccacaacaat    420
aattattcgg catcagagaa agaggaaaaa acccaggtga taaaattgtt ttcgcgcttt    480
gcgactagct ttaaagatta cttcaagaac cgtgcaaatt gcttttcagc ggacgatatt    540
tcatcaagca gctgccatcg catcgtcaac gacaatgcag agatattctt ttcaaatgcg    600
ctggtctacc gccggatcgt aaaaaacctg agcaatgacg atatcaacaa aatttcgggc    660
gatatgaaag attcattaaa agaaatgagt ctggatgaaa tatattctta cgagaagtat    720
```

-continued

```
ggggaattta ttacccagga aggcattagc ttctataatg atatctgtgg gaaagtgaat    780
tcttttatga acctgtattg tcagaaaaat aaagaaaaca aaaatttata caaacttcgt    840
aaacttcaca aacagattct atgcattgcg gacactagct atgaggtccc gtataaattt    900
gaaagtgacg aggaagtgta ccaatcagtt aacggcttcc ttgataacat tagcagcaaa    960
catatagtcg aaagattacg caaaatcggc gataactata acggctacaa cctggataaa   1020
atttatatcg tgtcccgttt ttacgagagc gttagccaaa aaacctaccg cgactgggaa   1080
acaattaata ccgccctcga aattcattac aataatatct tgccgggtaa cggtaaaagt   1140
aaagccgaca aagtaaaaaa agcggttaag aatgatttac agaaatccat caccgaaata   1200
aatgaactag tgtcaaacta taagctgtgc ccggacgaca acatcaaagc ggagacttat   1260
atacatgaga ttagccatat cttgaataac tttgaagcac aggaattgaa atacaatccg   1320
gaaattcacc tagttgaatc cgagctcaaa gcgagtgagc ttaaaaacgt gctggacgtg   1380
atcatgaatg cgtttcattg gtgttcggtt tttatgactg aggaacttgt tgataaagac   1440
aacaattttt atgcggaact ggaggagatt tacgatgaaa tttatccagt aattagtctg   1500
tacaacctgg ttcgtaacta cgttacccag aaaccgtaca gcacgaaaaa gattaaattg   1560
aactttggaa taccgacgtt agcagacggt tggtcaaagt ccaaagagta ttctaataac   1620
gctatcatac tgatgcgcga caatctgtat tatctgggca tctttaatgc gaagaataaa   1680
ccggacaaga agattatcga gggtaatacg tcagaaaata agggtgacta caaaaagatg   1740
atttataatt tgctcccggg tcccaacaaa atgatcccga aagttttctt gagcagcaag   1800
acgggggtgg aaacgtataa accgagcgcc tatatcctag aggggtataa acagaataaa   1860
catctgaagt cttcaaaaga ctttgatatc actttctgtc gtgatctgat cgactacttc   1920
aaaaactgta ttgcaattca tcccgagtgg aaaaacttcg gttttgattt tagcgacacc   1980
agtacttatg aagacatttc cgggttttat cgtgaggtag agttacaagg ttacaagatt   2040
gattggacat acattagcga aaaagacatt gatctgctgc aggaaaaagg tcaactgtat   2100
ctgttccaga tatataacaa agatttttcg aaaaaatcaa ccgggaatga caaccttcac   2160
accatgtacc tgaaaaatct tttctcagaa gaaaatctta aggatatcgt cctgaaactt   2220
aacggcgaag cggaaatctt cttcaggaag agcagcataa agaacccaat cattcataaa   2280
aaaggctcga ttttagtcaa ccgtacctac gaagcagaag aaaaagacca gtttggcaac   2340
attcaaattg tgcgtaaaac cattccggaa aacatttatc aggagctgta caaatacttc   2400
aacgataaaa gcgacaaaga gctgtctgat gaagcagcca aactgaagaa tgtagtggga   2460
caccacgagg cagcgacgaa tatagtcaag gactatcgct acacgtatga taaatacttc   2520
cttcatatgc ctattacgat caatttcaaa gccaataaaa cgagctttat taatgatagg   2580
atcttacagt atatcgctaa agaaaacgac ttacatgtga tcggcattga tcggggcgag   2640
cgtaacctga tctacgtgtc cgtgattgat acttgtggta atatagttga acagaaaagc   2700
tttaacattg taaacggcta cgactatcag ataaaactga aacaacagga gggcgctaga   2760
cagattgcgc ggaaagaatg gaaagaaatt ggtaaaatta aagagatcaa agagggctac   2820
ctgagcttag taatccacga gatctctaaa atggtaatca aatacaatgc aattatagcg   2880
atggaggatt tgtcttatgg ttttaaaaaa gggcgcttta aggtcgaacg gcaagtttac   2940
cagaaatttg aaaccatgct catcaataaa ctcaactatc tggtatttaa agatatttcg   3000
attaccgaga atggcggtct cctgaaaggt tatcagctga catacattcc tgaaaaactt   3060
```

```
aaaaacgtgg gtcatcagtg cggctgcatt ttttatgtgc ctgctgcata cacgagcaaa   3120

attgatccga ccaccggctt tgcgaatatc tttaaattta aagacctgac agtggacgca   3180

aaacgtgaat tcattaaaaa atttgactca attcgttatg acagtgaaaa aaatctgttc   3240

tgctttacat ttgactacaa taactttatt acgcaaaaca cggtcatgag caaatcatcg   3300

tggagtgtgt atacatacgg cgtgcgcatc aaacgtcgct ttgtgaacgg ccgcttctca   3360

aacgaaagtg ataccattga cataaccaaa gatatggaga aaacgttgga aatgacggac   3420

attaactggc gcgatggcca cgatcttcgt caagacatta tagattatga aattgttcag   3480

cacatattcg aaattttcaa attaacagtg caaatgcgta actccttgtc tgaactggag   3540

gaccgtgatt acgatcgtct catttcacct gtactgaacg aaaataacat tttttatgac   3600

agcgcgaaag cgggggatgc acttcctaag gatgccgatg caaatggtgc gtattgtatt   3660

gcattaaaag ggttatatga aattaaacaa attaccgaaa attggaaaga agatggtaaa   3720

ttttcgcgcg ataaactcaa aatcagcaat aaagattggt tcgactttat ccagaataag   3780

cgctatctct aa                                                       3792
```

<210> SEQ ID NO 6
<211> LENGTH: 3792
<212> TYPE: DNA
<213> ORGANISM: Artificial Sequence
<220> FEATURE:
<223> OTHER INFORMATION: Modified MAD7 nucleic acid sequence

<400> SEQUENCE: 6

```
atgaacaacg gcacaaataa ttttcagaac ttcatcggga tctcaagttt gcagaaaacg     60

ctgcgcaatg ctctgatccc cacggaaacc acgcaacagt tcatcgtcaa gaacggaata    120

attaaagaag atgagttacg tggcgagaac cgccagattc tgaaagatat catggatgac    180

tactaccgcg gattcatctc tgagactctg agttctattg atgacataga ttggactagc    240

ctgttcgaaa aaatggaaat tcagctgaaa aatggtgata ataaagatac cttaattaag    300

gaacaggcgg agaaacggaa agcaatctat aaaaaatttg cggatgacga tcggtttaag    360

aacatgttta gcgccaaact gattagtgac atattacctg aatttgtcat ccacaacaat    420

aattattcgg catcagagaa agaggaaaaa acccaggtga taaaattgtt ttcgcgcttt    480

gcgactagct ttaaagatta cttcaagaac cgtgcaaatt gcttttcagc ggacgatatt    540

tcatcaagca gctgccatcg catcgtcaac gacaatgcag agatattctt ttcaaatgcg    600

ctggtctacc gccggatcgt aaaaaacctg agcaatgacg atatcaacaa aatttcgggc    660

gatatgaaag attcattaaa agaaatgagt ctggaagaaa tatattctta cgagaagtat    720

ggggaattta ttacccagga aggcattagc ttctataatg atatctgtgg gaaagtgaat    780

tcttttatga acctgtattg tcagaaaaat aaagaaaaca aaaatttata caaacttcgt    840

aaacttcaca aacagattct atgcattgcg gacactagct atgaggtccc gtataaattt    900

gaaagtgacg aggaagtgta ccaatcagtt aacggcttcc ttgataacat tagcagcaaa    960

catatagtcg aaagattacg caaaatcggc gataactata acggctacaa cctggataaa   1020

atttatatcg tgtccaaatt ttacgagagc gttagccaaa aaacctaccg cgactgggaa   1080

acaattaata ccgccctcga aattcattac aataatatct tgccgggtaa cggtaaaagt   1140

aaagccgaca aagtaaaaaa agcggttaag aatgatttac agaaatccat caccgaaata   1200

aatgaactag tgtcaaacta taagctgtgc agtgacgaca acatcaaagc ggagacttat   1260

atacatgaga ttagccatat cttgaataac tttgaagcac aggaattgaa atacaatccg   1320
```

```
gaaattcacc tagttgaatc cgagctcaaa gcgagtgagc ttaaaaacgt gctggacgtg   1380
atcatgaatg cgtttcattg gtgttcggtt tttatgactg aggaacttgt tgataaagac   1440
aacaattttt atgcggaact ggaggagatt tacgatgaaa tttatccagt aattagtctg   1500
tacaacctgg ttcgtaacta cgttacccag aaaccgtaca gcacgaaaaa gattaaattg   1560
aactttggaa taccgacgtt agcagacggt tggtcaaagt ccaaagagta ttctaataac   1620
gctatcatac tgatgcgcga caatctgtat tatctgggca tctttaatgc gaagaataaa   1680
ccggacaaga agattatcga gggtaatacg tcagaaaata agggtgacta caaaaagatg   1740
atttataatt tgctcccggg tcccaacaaa atgatcccga aagttttctt gagcagcaag   1800
acgggggtgg aaacgtataa accgagcgcc tatatcctag aggggtataa acagaataaa   1860
catctgaagt cttcaaaaga ctttgatatc actttctgtc atgatctgat cgactacttc   1920
aaaaactgta ttgcaattca tcccgagtgg aaaaacttcg gttttgattt tagcgacacc   1980
agtacttatg aagacatttc cgggttttat cgtgaggtag agttacaagg ttacaagatt   2040
gattggacat acattagcga aaaagacatt gatctgctgc aggaaaaagg tcaactgtat   2100
ctgttccaga tatataacaa agatttttcg aaaaaatcaa ccgggaatga caaccttcac   2160
accatgtacc tgaaaaatct tttctcagaa gaaaatctta aggatatcgt cctgaaactt   2220
aacggcgaag cggaaatctt cttcaggaag agcagcataa agaacccaat cattcataaa   2280
aaaggctcga ttttagtcaa ccgtacctac gaagcagaag aaaaagacca gtttggcaac   2340
attcaaattg tgcgtaaaac cattccggaa aacatttatc aggagctgta caaatacttc   2400
aacgataaaa gcgacaaaga gctgtctgat gaagcagcca aactgaagaa tgtagtggga   2460
caccacgagg cagcgacgaa tatagtcaag gactatcgct acacgtatga taaatacttc   2520
cttcatatgc ctattacgat caatttcaaa gccaataaaa cgagctttat taatgatagg   2580
atcttacagt atatcgctaa agaaaaagac ttacatgtga tcggcattga tcggggcgag   2640
cgtaacctga tctacgtgtc cgtgattgat acttgtggta atatagttga acagaaaagc   2700
tttaacattg taaacggcta cgactatcag ataaaactga aacaacagga gggcgctaga   2760
cagattgcgc ggaaagaatg gaaagaaatt ggtaaaatta aagagatcaa agagggctac   2820
ctgagcttag taatccacga gatctctaaa atggtaatca aatacaatgc aattatagcg   2880
atggaggatt tgtcttatgg ttttaaaaaa gggcgcttta aggtcgaacg gcaagtttac   2940
cagaaatttg aaaccatgct catcaataaa ctcaactatc tggtatttaa agatatttcg   3000
attaccgaga atggcggtct cctgaaaggt tatcagctga catacattcc tgataaactt   3060
aaaaacgtgg gtcatcagtg cggctgcatt ttttatgtgc ctgctgcata cacgagcaaa   3120
attgatccga ccaccggctt tgtgaatatc tttaaattta aagacctgac agtggacgca   3180
aaacgtgaat tcattaaaaa atttgactca attcgttatg acagtgaaaa aaatctgttc   3240
tgctttacat ttgactacaa taactttatt acgcaaaaca cggtcatgag caaatcatcg   3300
tggagtgtgt atacatacgg cgtgcgcatc aaacgtcgct ttgtgaacgg ccgcttctca   3360
aacgaaagtg ataccattga cataaccaaa gatatggaga aaacgttgga aatgacggac   3420
attaactggc gcgatggcca cgatcttcgt caagacatta tagattatga aattgttcag   3480
cacatattcg aaattttcaa attaacagtg caaatgcgta actccttgtc tgaactggag   3540
gaccgtgatt acgatcgtct catttcacct gtactgaacg aaaataacat tttttatgac   3600
agcgcgaaag cgggggatgc acttcctaag gatgccgatg caaatggtgc gtattgtatt   3660
```

```
gcattaaaag ggttatatga aattaaacaa attaccgaaa attggaaaga agatggtaaa   3720

ttttcgcgcg ataaactcaa aatcagcaat aaagattggt tcgactttat ccagaataag   3780

cgctatctct aa                                                       3792


<210> SEQ ID NO 7
<211> LENGTH: 4005
<212> TYPE: DNA
<213> ORGANISM: Artificial Sequence
<220> FEATURE:
<223> OTHER INFORMATION: Modified MAD7 nucleic acid sequence

<400> SEQUENCE: 7

atgtcatcgc tcacgaaatt cactaacaaa tactctaaac agctcaccat taagaatgaa     60

ctcatcccag ttggcaaaac actggagaac atcaaagaga atggtctgat agatggcgac    120

gaacagctga atgagaatta tcagaaggcg aaaattattg tggatgattt tctgcgggac    180

ttcattaata aagcactgaa taatacgcag atcgggaact ggcgcgaact ggcggatgcc    240

cttaataaag aggatgaaga taacatcgag aaattgcagg ataaaattcg gggaatcatt    300

gtatccaaat ttgaaacgtt tgatctgttt agcagctatt ctattaagaa agatgaaaag    360

attattgacg acgacaatga tgttgaagaa gaggaactgg atctgggcaa gaagaccagc    420

tcatttaaat acatatttaa aaaaaacctg tttaagttag tgttgccatc ctacctgaaa    480

accacaaacc aggacaagct gaagattatt agctcgtttg ataatttttc aacgtacttc    540

cgcgggttct ttgaaaaccg gaaaaacatt tttaccaaga aaccgatctc cacaagtatt    600

gcgtatcgca ttgttcatga taacttcccg aaattccttg ataacattcg ttgttttaat    660

gtgtggcaga cggaatgccc gcaactaatc gtgaaagcag ataactatct gaaaagcaaa    720

aatgttatag cgaaagataa aagtttggca aactatttta ccgtgggcgc gtatgactat    780

ttcctgtctc agaatggtat agatttttac aacaatatta taggtggact gccagcgttc    840

gccggccatg agaaaatcca aggtctcaat gaattcatca atcaagagtg ccaaaaagac    900

agcgagctga aaagtaagct gaaaaaccgt cacgcgttca aaatggcggt actgttcaaa    960

cagatactca gcgatcgtga aaaaagtttt gtaattgatg agttcgagtc ggatgctcaa   1020

gttattgacg ccgttaaaaa cttttacgcc gaacagtgca aagataacaa tgttattttt   1080

aacttattaa atcttatcaa gaatatcgct ttcttaagtg atgacgaact ggacggcata   1140

ttcattgaag ggaaatacct gtcgagcgtt agtcaaaaac tctatagcga ttggtcaaaa   1200

ttacgtaacg acattgagga ttcggctaac tctaaacaag gcaataaaga gctggccaag   1260

aagatcaaaa ccaacaaagg ggatgtagaa aaagcgatct cgaaatatga gttctcgctg   1320

tcggaactga actcgattgt acatgataac accaagtttt ctgacctcct tagttgtaca   1380

ctgcataagg tggcttctga gaaactggtg aaggtcaatg aaggcgactg gccgaaacat   1440

ctcaagaata atgaagagaa acaaaaaatc aaagagccgc ttgatgctct gctggagatc   1500

tataatacac ttctgatttt taactgcaaa agcttcaata aaaacggcaa cttctatgtc   1560

gactatgatc gttgcatcaa tgaactgagt tcggtcgtgt atctgtataa taaaacacgt   1620

aactattgca ctaaaaaacc ctataacacg gacaagttca aactcaattt taacagtccg   1680

cagctcggtg aaggcttttc caagtcgaaa gaaaatgact gtctgactct tttgtttaaa   1740

aaagacgaca actattatgt aggcattatc cgcaaaggtg caaaaaatcaa ttttgatgat   1800

acacaagcaa tcgccgataa caccgacaat tgcatcttta aatgaatta tttcctactt   1860

aaagacgcaa aaaaatttat cccgaaatgt agcattcagc tgaaagaagt caaggcccat   1920
```

```
tttaagaaat ctgaagatga ttacattttg tctgataaag agaaatttgc tagcccgctg   1980

gtcattaaaa agagcacatt tttgctggca actgcacatg tgaaagggaa aaaaggcaat   2040

atcaagaaat ttcagaaaga atattcgaaa gaaaacccca ctgagtatcg caattcttta   2100

aacgaatgga ttgctttttg taaagagttc ttaaaaactt ataaagcggc taccattttt   2160

gatataacca cattgaaaaa ggcagaggaa tatgctgata ttgtagaatt ctacaaggat   2220

gtcgataatc tgtgctacaa actggagttc tgcccgatta aaacctcgtt tatagaaaac   2280

ctgatagata acggcgacct gtatctgttt cgcatcaata acaaagactt cagcagtaaa   2340

tcgaccggca ccaagaacct tcatacgtta tatttacaag ctatattcga tgaacgtaat   2400

ctgaacaatc cgacaattat gctgaatggg ggagcagaac tgttctatcg taaagaaagt   2460

attgagcaga aaaaccgtat cacacacaaa gccggttcaa ttctcgtgaa taaggtgtgt   2520

aaagacggta caagcctgga tgataagata cgtaatgaaa tttatcaata tgagaataaa   2580

tttattgata ccctgtctga tgaagctaaa aaggtgttac cgaatgtcat taaaaaggaa   2640

gctacccatg acattacaaa agataaacgt ttcactagtg acaaattctt ctttcactgc   2700

cccctgacaa ttaattataa ggaaggcgat accaagcagt tcaataacga agtgctgagt   2760

tttctgcgtg gaaatcctga catcaacatt atcggcattg accgcggaga gcgtaattta   2820

atctatgtaa cggttataaa ccagaaaggc gagattctgg attcggtttc attcaatacc   2880

gtgaccaaca agagttcaaa aatcgagcag acagtcgatt atgaagagaa attggcagtc   2940

cgcgagaaag agaggattga agcaaaacgt tcctgggact ctatctcaaa aattgcgaca   3000

ctaaaggaag gttatctgag cgcaatagtt cacgagatct gtctgttaat gattaaacac   3060

aacgcgatcg ttgtcttaga gaatcttaat gcaggcttta agcgtattcg tggcggttta   3120

tcagaaaaaa gtgtttatca aaaattcgaa aaaatgttga ttaacaaact gaactatttt   3180

gtcagcaaga aggaatccga ctggaataaa ccgtctggtc tgctgaatgg actgcagctt   3240

tcggatcagt ttgaaagctt cgaaaaactg ggtattcagt ctggttttat tttttacgtg   3300

ccggctgcat atacctcaaa gattgatccg accacgggct tcgccaatgt tctgaatctg   3360

tcgaaggtac gcaatgttga tgcgatcaaa agcttttttt ctaacttcaa cgaaattagt   3420

tatagcaaga aagaagccct tttcaaattc tcattcgatc tggattcact gagtaagaaa   3480

ggctttagta gctttgtgaa atttagtaag agtaaatgga acgtctacac ctttggagaa   3540

cgtatcataa agccaaagaa taagcaaggt tatcgggagg acaaaagaat caacttgacc   3600

ttcgagatga agaagttact taacgagtat aaggtttctt ttgatcttga aaataacttg   3660

attccgaatc tcacgagtgc caacctgaag gatacttttt ggaaagagct attctttatc   3720

ttcaagacta cgctgcagct ccgtaacagc gttactaacg gtaaagaaga tgtgctcatc   3780

tctccggtca aaaatgcgaa gggtgaattc ttcgtttcgg gaacgcataa caagactctt   3840

ccgcaagatt gcgatgcgaa cggtgcatac catattgcgt tgaaaggtct gatgatactc   3900

gaacgtaaca accttgtacg tgaggagaaa gatacgaaaa agattatggc gatttcaaac   3960

gtggattggt tcgagtacgt gcagaaacgt agaggcgttc tgtaa                   4005
```

<210> SEQ ID NO 8
<211> LENGTH: 3717
<212> TYPE: DNA
<213> ORGANISM: Artificial Sequence
<220> FEATURE:
<223> OTHER INFORMATION: Modified MAD nuclease nucleic acid sequence

<400> SEQUENCE: 8

```
atgaacaact acgacgaatt caccaaactg tacccgatcc agaaaaccat ccgtttcgaa      60
ctgaaaccgc agggtcgtac catggaacac ctggaaacct tcaacttctt cgaagaagac     120
cgtgaccgtg cggaaaaata caaaatcctg aaagaagcga tcgacgaata ccacaaaaaa     180
ttcatcgacg aacacctgac caacatgtct ctggactgga actctctgaa acagatctct     240
gaaaaatact acaaatctcg tgaagaaaaa gacaaaaaag ttttcctgtc tgaacagaaa     300
cgtatgcgtc aggaaatcgt ttctgaattc aaaaaagacg accgtttcaa agacctgttc     360
tctaaaaaac tgttctctga actgctgaaa gaagaaatct acaaaaaagg taaccaccag     420
gaaatcgacg cgctgaaatc tttcgacaaa ttctctggtt acttcatcgg tctgcacgaa     480
aaccgtaaaa acatgtactc tgacggtgac gaaatcaccg cgatctctaa ccgtatcgtt     540
aacgaaaact tcccgaaatt cctggacaac ctgcagaaat accaggaagc gcgtaaaaaa     600
tacccggaat ggatcatcaa agcggaatct gcgctggttg cgcacaacat caaaatggac     660
gaagttttct ctctggaata cttcaacaaa gttctgaacc aggaaggtat ccagcgttac     720
aacctggcgc tgggtggtta cgttaccaaa tctggtgaaa aaatgatggg tctgaacgac     780
gcgctgaacc tggcgcacca gtctgaaaaa tcttctaaag gtcgtatcca catgaccccg     840
ctgttcaaac agatcctgtc tgaaaaagaa tctttctctt acatcccgga cgttttcacc     900
gaagactctc agctgctgcc gtctatcggt ggtttcttcg cgcagatcga aaacgacaaa     960
gacggtaaca tcttcgaccg tgcgctggaa ctgatctctt cttacgcgga atacgacacc    1020
gaacgtatct acatccgtca ggcggacatc aaccgtgttt ctaacgttat cttcggtgaa    1080
tggggtaccc tgggtggtct gatgcgtgaa tacaaagcgg actctatcaa cgacatcaac    1140
ctggaacgta cctgcaaaaa agttgacaaa tggctggact ctaaagaatt cgcgctgtct    1200
gacgttctgg aagcgatcaa acgtaccggt aacaacgacg cgttcaacga atacatctct    1260
aaaatgcgta ccgcgcgtga aaaaatcgac gcggcgcgta aagaaatgaa attcatctct    1320
gaaaaaatct ctggtgacga agaatctatc cacatcatca aaccctgct ggactctgtt     1380
cagcagttcc tgcacttctt caacctgttc aaagcgcgtc aggacatccc gctggacggt    1440
gcgttctacg cggaattcga cgaagttcac tctaaactgt tcgcgatcgt tccgctgtac    1500
aacaaagttc gtaactacct gaccaaaaac aacctgaaca ccaaaaaaat caaactgaac    1560
ttcaaaaacc cgaccctggc gaacggttgg gaccagaaca aagtttacga ctacgcgtct    1620
ctgatcttcc tgcgtgacgg taactactac ctgggtatca tcaacccgaa acgtaaaaaa    1680
aacatcaaat tcgaacaggg ttctggtaac ggtccgttct accgtaaaat ggtttacaaa    1740
cagatcccgg gtccgaacaa aaacctgccg cgtgttttcc tgacctctac caaaggtaaa    1800
aaagaataca aaccgtctaa agaaatcatc gaaggttacg aagcggacaa acacatccgt    1860
ggtgacaaat tcgacctgga cttctgccac aaactgatcg acttcttcaa agaatctatc    1920
gaaaaacaca aagactggtc taaattcaac ttctacttct ctccgaccga atcttacggt    1980
gacatctctg aattctacct ggacgttgaa aaacagggtt accgtatgca cttcgaaaac    2040
atctctgcgg aaaccatcga cgaatacgtt gaaaaaggtg acctgttcct gttccagatc    2100
tacaacaaag acttcgttaa agcggcgacc ggtaaaaaag acatgcacac catctactgg    2160
aacgcggcgt tctctccgga aaacctgcag gacgttgttg ttaaactgaa cggtgaagcg    2220
gaactgttct accgtgacaa atctgacatc aaagaaatcg ttcaccgtga aggtgaaatc    2280
ctggttaacc gtacctacaa cggtcgtacc ccggttccgg acaaaatcca caaaaaactg    2340
```

```
accgactacc acaacggtcg taccaaagac ctgggtgaag cgaaagaata cctggacaaa   2400

gttcgttact tcaaagcgca ctacgacatc accaaagacc gtcgttacct gaacgacaaa   2460

atctacttcc acgttccgct gaccctgaac ttcaaagcga acggtaaaaa aaacctgaac   2520

aaaatggtta tcgaaaaatt cctgtctgac gaaaaagcgc acatcatcgg tatcgaccgt   2580

ggtgaacgta acctgctgta ctactctatc atcgaccgtt ctggtaaaat catcgaccag   2640

cagtctctga acgttatcga cggtttcgac taccgtgaaa aactgaacca gcgtgaaatc   2700

gaaatgaaag acgcgcgtca gtcttggaac gcgatcggta aaatcaaaga cctgaaagaa   2760

ggttacctgt ctaaagcggt tcacgaaatc accaaaatgg cgatccagta caacgcgatc   2820

gttgttatgg aagaactgaa ctacggtttc aaacgtggtc gtttcaaagt tgaaaaacag   2880

atctaccaga aattcgaaaa catgctgatc gacaaaatga actacctggt tttcaaagac   2940

gcgccggacg aatctccggg tggtgttctg aacgcgtacc agctgaccaa cccgctggaa   3000

tctttcgcga aactgggtaa acagaccggt atcctgttct acgttccggc ggcgtacacc   3060

tctaaaatcg acccgaccac cggtttcgtt aacctgttca acacctcttc taaaaccaac   3120

gcgcaggaac gtaaagaatt cctgcagaaa ttcgaatcta tctcttactc tgcgaaagac   3180

ggtggtatct tcgcgttcgc gttcgactac cgtaaattcg gtacctctaa aaccgaccac   3240

aaaaacgttt ggaccgcgta caccaacggt gaacgtatgc gttacatcaa agaaaaaaaa   3300

cgtaacgaac tgttcgaccc gtctaaagaa atcaaagaag cgctgacctc ttctggtatc   3360

aaatacgacg gtggtcagaa catcctgccg gacatcctgc gttctaacaa caacggtctg   3420

atctacacca tgtactcttc tttcatcgcg gcgatccaga tgcgtgttta cgacggtaaa   3480

gaagactaca tcatctctcc gatcaaaaac tctaaaggtg aattcttccg taccgacccg   3540

aaacgtcgtg aactgccgat cgacgcggac gcgaacggtg cgtacaacat cgcgctgcgt   3600

ggtgaactga ccatgcgtgc gatcgcggaa aaattcgacc cggactctga aaaaatggcg   3660

aaactggaac tgaaacacaa agactggttc gaattcatgc agacccgtgg tgactaa      3717
```

<210> SEQ ID NO 9
<211> LENGTH: 3897
<212> TYPE: DNA
<213> ORGANISM: Artificial Sequence
<220> FEATURE:
<223> OTHER INFORMATION: Modified MAD nuclease nucleic acid sequence

<400> SEQUENCE: 9

```
atgactaaaa catttgattc agagtttttt aatttgtact cgctgcaaaa aacggtacgc     60

tttgagttaa aacccgtggg agaaaccgcg tcatttgtgg aagactttaa aaacgagggc    120

ttgaaacgtg ttgtgagcga agatgaaagg cgagccgtcg attaccagaa agttaaggaa    180

ataattgacg attaccatcg ggatttcatt gaagaaagtt taaattattt tccggaacag    240

gtgagtaaag atgctcttga gcaggcgttt catctttatc agaaactgaa ggcagcaaaa    300

gttgaggaaa gggaaaaagc gctgaaagaa tgggaagcgc tgcagaaaaa gctacgtgaa    360

aaagtggtga aatgcttctc ggactcgaat aaagcccgct tctcaaggat tgataaaaag    420

gaactgatta aggaagacct gataaattgg ttggtcgccc agaatcgcga ggatgatatc    480

cctacggtcg aaacgtttaa caacttcacc acatatttta ccggcttcca tgagaatcgt    540

aaaaatattt actccaaaga tgatcacgcc accgctatta gctttcgcct tattcatgaa    600

aatcttccaa agtttttga caacgtgatt agcttcaata agttgaaaga gggtttccct    660
```

-continued

```
gaattaaaat ttgataaagt gaaagaggat ttagaagtag attatgatct gaagcatgcg    720
tttgaaatag aatatttcgt taacttcgtg acccaagcgg gcatagatca gtataattat    780
ctgttaggag ggaaaaccct ggaggacggg acgaaaaaac aagggatgaa tgagcaaatt    840
aatctgttca aacaacagca aacgcgagat aaagcgcgtc agattcccaa actgatcccc    900
ctgttcaaac agattcttag cgaaaggact gaaagccagt cctttattcc taaacaattt    960
gaaagtgatc aggagttgtt cgattcactg cagaagttac ataataactg ccaggataaa   1020
ttcaccgtgc tgcaacaagc cattctcggt ctggcagagg cggatcttaa gaaggtcttc   1080
atcaaaacct ctgatttaaa tgccttatct aacaccattt tcgggaatta cagcgtcttt   1140
tccgatgcac tgaacctgta taaagaaagc ctgaaaacga aaaaagcgca ggaggctttt   1200
gagaaactac cggcccattc tattcacgac ctcattcaat acttggaaca gttcaattcc   1260
agcctggacg cggaaaaaca acagagcacc gacaccgtcc tgaactactt catcaagacc   1320
gatgaattat attctcgctt cattaaatcc actagcgagg ctttcactca ggtgcagcct   1380
ttgttcgaac tggaagccct gtcatctaag cgccgcccac cggaatcgga agatgaaggg   1440
gcaaaagggc aggaaggctt cgagcagatc aagcgtatta aagcttacct ggatacgctt   1500
atggaagcgg tacactttgc aaagccgttg tatcttgtta agggtcgtaa aatgatcgaa   1560
gggctcgata aagaccagtc cttttatgaa gcgtttgaaa tggcgtacca agaacttgaa   1620
tcgttaatca ttcctatcta taacaaagcg cggagctatc tgtcgcggaa acctttcaag   1680
gccgataaat tcaagattaa ttttgacaac aacacgctac tgagcggatg ggatgcgaac   1740
aaggaaactg ctaacgcgtc cattctgttt aagaaagacg ggttatatta ccttggaatt   1800
atgccgaaag gtaagacctt tctctttgac tactttgtat cgagcgagga ttcagagaaa   1860
ctgaaacagc gtcgccagaa gaccgccgaa gaagctctgg cgcaggatgg tgaaagttac   1920
ttcgaaaaaa ttcgttataa actgttacca ggggcttcaa agatgttacc gaaagtcttt   1980
tttagcaaca aaaatattgg cttttacaac ccgtcggatg acattttacg cattcgcaac   2040
acagcctctc acaccaaaaa cgggacccct cagaaaggcc actcaaaagt tgagtttaac   2100
ctgaatgatt gtcataagat gattgatttc ttcaaatcat caattcagaa acacccggaa   2160
tgggggtctt ttggctttac gttttctgat accagtgatt ttgaagacat gagtgccttc   2220
taccgggaag tagaaaacca gggttacgta attagctttg acaaaatcaa agagacctat   2280
atacagagcc aggtggaaca gggtaatctc tacttattcc agatttataa caaggatttc   2340
tcgccctaca gcaaaggcaa accaaacctg catactctgt actggaaagc cctgtttgaa   2400
gaagcgaacc tgaataacgt agtggcgaag ttgaacggtg aagcggaaat cttcttccgt   2460
cgtcactcca ttaaggcctc tgataaagtt gtccatccgg caaatcaggc cattgataat   2520
aagaatccac acacggaaaa aacgcagtca acctttgaat atgacctcgt taaagacaaa   2580
cgctacacgc aagataagtt ctttttccac gtcccaatca gcctcaactt taaagcacaa   2640
ggggtttcaa agtttaatga taaagtcaat gggttcctca agggcaaccc ggatgtcaac   2700
attataggta tagacagggg cgaacgccat ctgctttact ttaccgtagt gaatcagaaa   2760
ggtgaaatac tggttcagga atcattaaat accttgatgt cggacaaagg gcacgttaat   2820
gattaccagc agaaactgga taaaaaagaa caggaacgtg atgctgcgcg taaatcgtgg   2880
accacggttg agaacattaa agagctgaaa gaggggtatc taagccatgt ggtacacaaa   2940
ctggcgcacc tcatcattaa atataacgca atagtctgcc tagaagactt gaattttggc   3000
tttaaacgcg gccgcttcaa agtggaaaaa caagtttatc aaaaatttga aaaggcgctt   3060
```

atagataaac tgaattatct ggtttttaaa gaaaaggaac ttggtgaggt agggcactac 3120
ttgacagctt atcaactgac ggccccgttc gaatcattca aaaaactggg caaacagtct 3180
ggcattctgt tttacgtgcc ggcagattat acttcaaaaa tcgatccaac aactggcttt 3240
gtgaacttcc tggacctgag atatcagtct gtagaaaaag ctaaacaact tcttagcgat 3300
tttaatgcca ttcgttttaa cagcgttcag aattactttg aattcgaaat tgactataaa 3360
aaacttactc cgaaacgtaa agtcggaacc caaagtaaat gggtaatttg tacgtatggc 3420
gatgtcaggt atcagaaccg tcggaatcaa aaaggtcatt gggagaccga agaagtgaac 3480
gtgaccgaaa agctgaaggc tctgttcgcc agcgattcaa aaactacaac tgtgatcgat 3540
tacgcaaatg atgataacct gatagatgtg attttagagc aggataaagc cagctttttt 3600
aaagaactgt tgtggctcct gaaacttacg atgaccttac gacattccaa gatcaaatcg 3660
gaagatgatt ttattctgtc accggtcaag aatgagcagg gtgaattcta tgatagtagg 3720
aaagccggcg aagtgtggcc gaaagacgcc gacgccaatg gcgcctatca tatcgcgctc 3780
aaagggcttt ggaatttgca gcagattaac cagtgggaaa aaggtaaaac cctgaatctg 3840
gctatcaaaa accaggattg gtttagcttt atccaagaga aaccgtatca ggaatga 3897

<210> SEQ ID NO 10
<211> LENGTH: 3708
<212> TYPE: DNA
<213> ORGANISM: Artificial Sequence
<220> FEATURE:
<223> OTHER INFORMATION: Modified MAD nuclease nucleic acid sequence

<400> SEQUENCE: 10
atgcatacag gcggtcttct tagtatggac gcgaaagagt tcacaggtca gtatccgttg 60
tcgaaaacat tacgattcga acttcggccc atcggccgca cgtgggataa cctggaggcc 120
tcaggctact tagcggaaga ccgccatcgt gccgaatgtt atcctcgtgc gaaagagtta 180
ttggatgaca accatcgtgc cttcctgaat cgtgtgttgc cacaaatcga tatggattgg 240
cacccgattg cggaggcctt ttgtaaggta cataaaaacc ctggtaataa agaacttgcc 300
caggattaca accttcagtt gtcaaagcgc cgtaaggaga tcagcgcata tcttcaggat 360
gcagatggct ataaaggcct gttcgcgaag cccgccttag acgaagctat gaaaattgcg 420
aaagaaaacg ggaacgaaag tgatattgag gttctcgaag cgtttaacgg ttttagcgta 480
tacttcaccg gttatcatga gtcacgcgag aacatttata gcgatgagga tatggtgagc 540
gtagcctacc gaattactga ggataatttc ccgcgctttg tctcaaacgc tttgatcttt 600
gataaattaa acgaaagcca tccggatatt atctctgaag tatcgggcaa tcttggagtt 660
gatgacattg gtaagtactt tgacgtgtcg aactataaca attttctttc ccaggccggt 720
atagatgact acaatcacat tattggcggc catacaaccg aagacggact gatacaagcg 780
tttaatgtcg tattgaactt acgtcaccaa aaagaccctg gctttgaaaa aattcagttc 840
aaacagctct acaaacaaat cctgagcgtg cgtaccagca aaagctacat cccgaaacag 900
tttgacaact ctaaggagat ggttgactgc atttgcgatt atgtcagcaa aatagagaaa 960
tccgaaacag tagaacgggc cctgaaacta gtccgtaata tcagttcttt cgacttgcgc 1020
gggatctttg tcaataaaaa gaacttgcgc atactgagca acaaactgat aggagattgg 1080
gacgcgatcg aaaccgcatt gatgcatagt tcttcatcag aaaacgataa gaaaagcgta 1140
tatgatagcg cggaggcttt tacgttggat gacatctttt caagcgtgaa aaaattttct 1200

```
gatgcctctg ccgaagatat tggcaacagg gcggaagaca tctgtagagt gataagtgag   1260
acggcccctt ttatcaacga tctgcgagcg gtggacctgg atagcctgaa cgacgatggt   1320
tatgaagcgg ccgtctcaaa aattcgggag tcgctggagc cttatatgga tcttttccat   1380
gaactggaaa ttttctcggt tggcgatgag ttcccaaaat gcgcagcatt ttacagcgaa   1440
ctggaggaag tcagcgaaca gctgatcgaa attattccgt tattcaacaa ggcgcgttcg   1500
ttctgcaccc ggaaacgcta tagcaccgat aagattaaag tgaacttaaa attcccgacc   1560
ttggcggacg ggtgggacct gaacaaagag agagacaaca aagccgcgat tctgcggaaa   1620
gacggtaagt attatctggc aattctggat atgaagaaag atctgtcaag cattaggacc   1680
agcgacgaag atgaatccag cttcgaaaag atggagtata aactgttacc gagtccagta   1740
aaaatgctgc caaagatatt cgtaaaatcg aaagccgcta aggaaaaata tggcctgaca   1800
gatcgtatgc ttgaatgcta cgataaaggt atgcataagt cgggtagtgc gtttgatctt   1860
ggcttttgcc atgaactcat tgattattac aagcgttgta tcgcggagta cccaggctgg   1920
gatgtgttcg atttcaagtt tcgcgaaact tccgattatg ggtccatgaa agagttcaat   1980
gaagatgtgg ccggagccgg ttactatatg agtctgagaa aaattccgtg cagcgaagtg   2040
taccgtctgt tagacgagaa atcgatttat ctatttcaaa tttataacaa agattactct   2100
gaaaatgcac atggtaataa gaacatgcat accatgtact gggagggtct cttttccccg   2160
caaaacctgg agtcgcccgt tttcaagttg tcgggtgggg cagaactttt ctttcgaaaa   2220
tcctcaatcc ctaacgatgc caaaacagta cacccgaaag gctcagtgct ggttccacgt   2280
aatgatgtta acggtcggcg tattccagat tcaatctacc gcgaactgac acgctatttt   2340
aaccgtggcg attgccgaat cagtgacgaa gccaaaagtt atcttgacaa ggttaagact   2400
aaaaaagcgg accatgacat tgtgaaagat cgccgcttta ccgtggataa aatgatgttc   2460
cacgtcccga ttgcgatgaa ctttaaggcg atcagtaaac cgaacttaaa caaaaaagtc   2520
attgatggca tcattgatga tcaggatctg aaaatcattg gtattgatcg tggcgagcgg   2580
aacttaattt acgtcacgat ggttgacaga aaagggaata tcttatatca ggattctctt   2640
aacatcctca atggctacga ctatcgtaaa gctctggatg tgcgcgaata tgacaacaag   2700
gaagcgcgtc gtaactggac taaagtggag ggcattcgca aaatgaagga aggctatctg   2760
tcattagcgg tctcgaaatt agcggatatg attatcgaaa ataacgccat catcgttatg   2820
gaggacctga accacggatt caaagcgggc cgctcaaaga ttgaaaaaca agtttatcag   2880
aaatttgaga gtatgctgat taacaaactg ggctatatgg tgttaaaaga caagtcaatt   2940
gaccaatcag gtggcgcgct gcatggatac cagctggcga accatgttac caccttagca   3000
tcagttggaa agcagtgtgg ggttatcttt tatataccgg cagcgttcac tagtaaaata   3060
gatccgacca ctggtttcgc cgatctcttt gccctgagta acgttaaaaa cgtagcgagc   3120
atgcgtgaat tcttttccaa aatgaaatct gtcatttatg ataaagctga aggcaaattc   3180
gcattcacct ttgattactt ggattacaac gtgaagagcg aatgtggtcg tacgctgtgg   3240
accgtttaca ccgttggtga gcgcttcacc tattcccgtg tgaaccgcga atatgtacgt   3300
aaagtcccca ccgatattat ctatgatgcc ctccagaaag caggcattag cgtcgaagga   3360
gacttaaggg acagaattgc cgaaagcgat ggcgatacgc tgaagtctat tttttacgca   3420
ttcaaatacg cgctagatat gcgcgttgag aatcgcgagg aagactacat tcaatcacct   3480
gtgaaaaatg cctctgggga atttttttgt tcaaaaaatg ctggtaaaag cctcccacaa   3540
gatagcgatg caaacggtgc atataacatt gccctgaaag gtattcttca attacgcatg   3600
```

ctgtctgagc agtacgaccc caacgcggaa tctattagac ttccgctgat aaccaataaa 3660
gcctggctga cattcatgca gtctggcatg aagacctgga aaaattag 3708

<210> SEQ ID NO 11
<211> LENGTH: 3783
<212> TYPE: DNA
<213> ORGANISM: Artificial Sequence
<220> FEATURE:
<223> OTHER INFORMATION: Modified MAD nuclease nucleic acid sequence

<400> SEQUENCE: 11
atggatagtt taaaagattt tacgaatcta tatcccgtaa gcaaaactct tcgttttgaa 60
ctgaaacctg ttggaaaaac gttggagaat atcgagaaag cgggcatcct gaaagaagac 120
gagcaccgtg ccgaaagcta caggcgtgtc aaaaagatta tcgatactta tcacaaagtg 180
ttcattgata gcagtctgga gaacatggca aaaatgggca tagaaaatga aatcaaagca 240
atgctgcaga gcttttgcga gctctacaag aaagatcacc gaacggaagg tgaagataaa 300
gcactggaca aaattcgcgc cgttcttcgc ggtctgattg ttggcgcgtt caccggcgtg 360
tgcggccgcc gtgaaaacac cgtgcagaac gaaaagtacg agtcgctgtt caaagaaaaa 420
ctgataaaag aaattttgcc tgactttgtg ctttcgaccg aagcggaatc cctgccattt 480
tctgtcgaag aagcgacccg cagcctgaaa gaatttgact cattcacaag ttactttgca 540
ggcttctacg aaaaccgtaa aaacatctac agcacgaagc cacagagcac ggctattgct 600
tatcgcctga ttcatgagaa cctgccgaag ttcatcgata acatccttgt ttttcaaaaa 660
attaaagagc cgattgcgaa agagttagaa catattcgag ctgacttttc tgcgggtggg 720
tacattaaaa aagatgagcg gctggaagac atcttcagtc taaactatta tatccacgtt 780
ctgtcgcagg caggcattga gaaatataat gcgctgattg gtaagattgt cacagaaggc 840
gatggtgaga tgaaaggtct taatgaacat atcaatctgt ataaccagca gcgtggtcgc 900
gaagaccgtc ttccactgtt ccgccccactg tataaacaga tcctgtctga ccgggaacag 960
ctgtcctacc tgccggaaag ctttgaaaag gatgaagagc tacttcgcgc attaaaggag 1020
ttttacgacc atattgcgga agacattttg ggtagaacgc agcaactgat gacgtcaatt 1080
tctgaatacg atctgagtag aatctacgtt aggaatgata gccagctgac cgatattagc 1140
aaaaaaatgc tgggcgactg gaacgctatc tatatggcac gtgaacgtgc atatgatcat 1200
gaacaagcac cgaaacgtat aaccgcgaaa tatgagcgtg atcgcattaa ggcgctaaag 1260
ggagaagaaa gcatctcact cgcaaacctg aactcctgta tcgctttctt agataacgtg 1320
cgcgattgtc gcgtcgacac gtatctgtca acccttgggc agaaagaggg tccacatggt 1380
ctgtctaacc tggtggaaaa tgtctttgcg agttaccatg aagcggaaca actgctgtct 1440
tttccatacc ccgaagaaaa caatctaata caggataaag ataacgtggt gttaatcaaa 1500
aacctgctgg acaacatcag cgatctgcaa cgtttcctga aacctttgtg gggtatgggt 1560
gacgagccag acaaagacga acgtttttat ggtgagtata attatatacg tggcgccctt 1620
gaccaagtta ttccgctgta taacaaagta cggaactatc tgacccgtaa gccatattct 1680
acccgtaaag tgaaactgaa ctttggcaac tcgcaactgc tgtcgggttg ggatcgtaac 1740
aaagaaaaag ataatagttg tgttatcctg cgtaagggac aaaattttta cctcgcgatt 1800
atgaacaaca gacacaagcg ttcatttgaa aataaggttc tgccggagta taaagagggc 1860
gaaccgtact tcgagaaaat ggattataag ttcttaccag accctaataa gatgttaccg 1920

```
aaagtctttc tttcgaaaaa aggcatagaa atctataagc cgtccccgaa attactcgaa   1980
cagtatgggc acgggaccca caagaaaggg gatactttta gcatggacga tctgcacgaa   2040
ctgatcgatt tttttaaaca ctccatcgaa gcccatgaag actggaaaca gtttgggttc   2100
aagttctctg atacagccac atacgagaat gtgtctagtt tttatcggga agtggaggat   2160
cagggctaca aacttagttt tcgtaaagtt tcagagagtt atgtttatag tttaattgat   2220
cagggaaaac tttacctgtt ccagatctac aacaaagatt tctcgccatg tagtaagggt   2280
accccgaatc tgcatacact ctattggaga atgttattcg atgagcgtaa cttagcggat   2340
gtcatttata aattggacgg gaaagcagag atctttttc gtgaaaaatc actgaagaat    2400
gaccacccga ctcatccggc cgggaaaccg atcaaaaaaa aatcccgcca gaaaaaagga   2460
gaagagtctc tgtttgaata tgatctggtg aaagaccgtc attacactat ggataaattt   2520
caatttcatg ttccaattac aatgaacttc aaatgttcgg cgggttccaa agtaaatgat   2580
atggtaaacg cccatattcg cgaagcgaaa gatatgcatg ttattggcat cgatagaggc   2640
gaaagaaacc tgctttatat ttgcgtaatt gacagccgtg gtaccattct ggaccagatc   2700
tctttaaaca ccatcaatga catcgattat cacgacctgt tggagtctcg ggacaaggac   2760
cgccagcagg agcgccgtaa ttggcagaca attgaaggca taaaagaatt aaaacagggt   2820
tacctttccc aggccgtaca ccgcatagcg gaactgatgg tggcctacaa agccgtagtt   2880
gccctggaag acttgaatat ggggtttaaa cgtggccgtc aaaaagtcga gagcagcgtg   2940
tatcagcaat ttgaaaaaca gttgattgac aagttgaatt atttggttga taaaaagaaa   3000
cgtccagaag atattggtgg cttactgcgt gcataccagt ttacggcacc ttttaagtcc   3060
ttcaaagaaa tgggtaaaca gaacgggttt ctgttttaca tcccggcctg gaatacatcc   3120
aacatcgatc ctaccaccgg gtttgtcaac ctgtttcatg cacaatatga aaacgtggat   3180
aaagcgaaga gtttttttcca aaaattcgat agtatttcgt ataacccaaa aaaagattgg  3240
tttgagtttg cgttcgatta taaaaatttt actaaaaagg ctgagggatc ccgcagtatg   3300
tggatcctct gcacccatgg cagtcgtatt aaaaattttc gtaattcgca aaagaatggc   3360
cagtgggact cggaagagtt tgccctgacc gaagcgttca aatcgctgtt tgtacgctac   3420
gaaattgact acacagcaga tctgaaaaca gccatcgtcg atgaaaaaca gaaagatttt   3480
tttgtagatc tcctaaaact gttcaaactg actgttcaga tgcgcaattc ctggaaagag   3540
aaagacctgg attatctgat tagcccggta gccggtgctg atggacgatt tttcgatact   3600
cgtgaaggta acaaaagtct cccgaaagat gctgatgcca atggtgcata caatattgca   3660
ttaaaggggc tatgggcctt gcgacagatc cgccagacca gcgaaggcgg caagctgaaa   3720
ttggccatat cgaataagga atggttacaa tttgttcagg aacgtagcta tgaaaaagat   3780
tga                                                                 3783
```

<210> SEQ ID NO 12
<211> LENGTH: 3923
<212> TYPE: DNA
<213> ORGANISM: Artificial Sequence
<220> FEATURE:
<223> OTHER INFORMATION: Modified MAD nuclease nucleic acid sequence

<400> SEQUENCE: 12

```
tgactcagtt tgagggtttt accaatctgt accaagtgtc aaaaaccctg cgttttgagt     60
taatacctca gggtaaaaca ctcaagcaca ttcaggagca aggtttcatc gaagaggaca    120
aagcgcgcaa tgaccattat aaagaactga aacccatcat tgaccgtatt tataaaacct    180
```

```
atgcagatca gtgcctgcag ctggtgcaac ttgattggga gaaccttagc gccgccatcg    240
acagttatcg taaagagaaa acagaagaaa cgcgtaacgc gttaatcgaa gaacaagcga    300
catatcgtaa cgctatccac gattacttta ttggtcgaac tgataatctg actgacgcta    360
tcaataaacg gcatgcggaa atctacaaag gtctattcaa agcggaacta tttaacggta    420
aggtcctgaa acaactgggg accgtaacga ccacagagca tgagaacgcc ctcctgcgct    480
ctttcgataa atttacgacc tatttttctg gtttttacga aaatcgtaag aacgtcttct    540
cagcggaaga cattagcacc gcgatcccgc atcggattgt tcaggataat tttccgaaat    600
ttaaggaaaa ctgccacatt tttacacgtt tgatcacagc cgtcccgagc ctgcgtgaac    660
acttcgaaaa cgttaaaaag gcgatcggca ttttcgtgtc aacgagcatc gaagaagtct    720
tcagcttccc tttttataac cagcttctga cacagacaca gattgacttg tacaaccaat    780
tgttaggagg catttccagg gaagctggca cagaaaaaat taaagggctg aatgaagtcc    840
ttaatttagc gattcagaaa aatgatgaga cggctcatat tattgcgtct ctgccgcacc    900
gatttatccc attattcaag caaattcttt ccgatcgcaa caccttatca ttcattttgg    960
aggaatttaa aagcgacgaa gaagtcatcc agtctttctg caaatacaaa acactgctgc   1020
gcaacgaaaa cgtgttggag accgccgaag ctctgttcaa cgagctcaac tctattgatc   1080
tgacccatat ctttatcagc cataagaaac tggaaacgat ttcatcagcc ctgtgcgatc   1140
actgggatac actgcgtaat gctctttatg agcgtagaat ctcagagctg acgggcaaga   1200
ttacgaaaag tgcaaaagaa aaagtgcagc gctctctgaa gcacgaagat attaacctgc   1260
aggaaatcat cagtgctgca ggcaaggaac tctctgaagc gtttaaacag aagaccagcg   1320
aaattcttag tcatgctcac gctgcattag accagccgct gccgacgaca ctcaagaagc   1380
aagaagaaaa agaaatcctg aagagtcagc tggattctct tctgggattg tatcacttgc   1440
tcgattggtt tgcagttgat gagtccaatg aggtagatcc tgaatttagt gcgcgtctga   1500
ccggcattaa acttgaaatg gaaccgagcc tgagtttcta caataaagcg cgtaattacg   1560
cgaccaaaaa accttatagc gtggagaaat ttaaactgaa tttccagatg ccgaccctag   1620
cgtccgggtg ggacgtaaat aaagaaaaaa acaacggcgc cattctcttc gtgaaaaacg   1680
gtttatacta tcttggaatt atgccgaaac agaaaggacg ttacaaggca ctgagcttcg   1740
aaccaacaga gaagacgtcc gaggggtttg ataagatgta ttacgattac tttccagatg   1800
cagccaaaat gatacctaaa tgctcaacac aattaaaagc ggttacagcg cattttcaaa   1860
cacataccac cccaattctt ctgtcgaata atttcattga gccccttgaa attacaaaag   1920
aaatttatga cttaaataat ccggaaaaag aaccgaaaaa gtttcaaacc gcctatgcga   1980
aaaaaaccgg cgaccagaaa ggataccgtg aagcgctgtg caaatggatc gactttaccc   2040
gcgatttcct tagtaaatat acgaaaacca cgtcaatcga tttgagctca cttcgtcctt   2100
caagtcagta taaagattta ggcgaatact acgcagaatt aaatcccctg ttatatcaca   2160
tctcttttca acgtatcgcg gaaaaagaaa tcatggacgc tgttgaaacg ggaaaactgt   2220
atctgtttca gatatacaat aaggattttg cgaaaggcca tcacggtaaa ccgaaccttc   2280
atacacttta ctggacagga ttattcagcc ctgagaattt ggcgaaaact tcgattaaat   2340
taaacggcca agcagaatta ttttatcggc cgaagagccg catgaagagg atggcccatc   2400
gcctgggaga aaaaatgctt aacaaaaaat tgaaagacca gaagacaccc attccggaca   2460
ccctgtacca ggagctgtat gactatgtaa atcatcgctt gagccatgat ctgtctgacg   2520
```

```
aagcgcgtgc actgctccct aacgtcatca ccaaggaagt ttcacacgag atcatcaaag   2580
accgccgttt taccagcgat aaattctttt ttcacgtgcc gatcacatta aactaccagg   2640
cagctaactc tccgtctaaa ttcaaccaac gcgttaacgc gtatcttaaa gaacatccag   2700
agaccccgat tattggcatc gaccgtgggg agcgtaacct gatttatatt accgtgatag   2760
acagcacggg aaagatttta gagcagcgaa gccttaacac cattcagcag ttcgactatc   2820
aaaaaaaatt ggacaaccgt gaaaaggagc gtgttgcggc ccgtcaagct tggagtgtcg   2880
ttggaaccat taaagacctg aaacagggct atttatccca ggtaattcat gaaatagttg   2940
atttaatgat tcactatcag gcagtggttg tgctggagaa cctgaacttt ggctttaaat   3000
cgaagcgcac tggcatagct gaaaaggcgg tgtatcagca gttcgagaag atgctgatcg   3060
ataagctgaa ttgtctcgtc ctgaaagact acccagcaga aaaggtcggc ggtgtcctga   3120
acccttatca actgaccgac cagttcacct catttgcgaa gatgggcacc caatccggat   3180
ttctcttcta tgtgccggcc ccatatacct cgaagattga cccgttaaca ggctttgtgg   3240
atccgttcgt gtggaaaact atcaaaaacc acgaaagccg gaaacacttc ctggagggat   3300
tcgattttct gcactacgac gtaaaaaccg ggatttcat tctgcatttc aaaatgaatc   3360
gtaacctgtc attccagcgc gggcttcctg gctttatgcc ggcatgggat attgtgtttg   3420
aaaaaaacga aactcagttc gatgctaaag gcactccgtt catagctgga aagagaatcg   3480
tcccagtcat agaaaaccat cgcttcaccg gtcgctatcg ggatttgtat ccggccaacg   3540
agctcattgc actgctggaa gaaaaaggca tcgtgtttag agatgggagt aacattcttc   3600
cgaaactcct ggaaaacgat gactcacacg ccattgacac tatggtggcc ctgattcgct   3660
ccgttttaca gatgcgcaat tccaacgcag cgacgggtga agattatatc aatagccctg   3720
tccgagactt gaacggcgtt tgctttgata gcaggttcca aaatccagaa tggccgatgg   3780
atgcggacgc caatggagcg tatcacatcg cgctgaaggg acaattactg ctgaaccacc   3840
tgaaagagtc aaaagactta aaattgcaga acggtatcag caatcaagat tggctggctt   3900
acattcaaga attacggaat taa                                           3923
```

<210> SEQ ID NO 13
<211> LENGTH: 4212
<212> TYPE: DNA
<213> ORGANISM: Artificial Sequence
<220> FEATURE:
<223> OTHER INFORMATION: Modified MAD nuclease nucleic acid sequence

<400> SEQUENCE: 13

```
atgctatttt ttatgtccac agatattacc aacaaaccga gagagaaagg cgtctttgat     60
aatttcacaa acttatacga gttcagtaag acgctaacct tcggcctcat tccacttaaa    120
tgggatgaca acaagaaaat gatcgtcgaa gacgaagatt tctcggtcct gcgcaaatat    180
ggtgttattg aggaagataa acgcatcgcg gagagtatta agattgccaa gttctacctg    240
aacatcctgc atcgtgaact gattggcaaa gtcctgggta gcctgaaatt tgaaaagaag    300
aacctggaga attacgaccg tttgctgggc gaaatagaga agaataataa gaatgagaat    360
atatcggaag acaagaagaa ggagataagg aagaacttca agaaggagtt gtctatcgcg    420
caggatatcc tgttaaagaa ggtgggtgaa gtgttcgaga gcaacggcag cggcattctg    480
agctccaaga attgtcttga tgagttgacc aaacgattta ctaggcaaga agtagataaa    540
ctgagaagag agaacaaaga tattggcgtt gaatacccag acgtagcata cagggagaag    600
gatgggaaag aggaaactaa atctttcttc gcgatggatg tgggttactt ggacgatttc    660
```

```
cataagaatc ggaaacagct atactctgtg aaaggaaaga agaatagcct gggcagacga    720
attctggaca acttcgagat cttctgcaag aataagaagt tgtacgagaa atacaagaat    780
ttggacatcg atttcagcga aatcgaacgg aacttcaatc tcacgctgga gaaagtgttc    840
gactttgaca attacaacga acgcctgact caagagggtt tagatgagta tgctaagatc    900
ctcggaggcg agagcaacaa acaggaacgc acggccaaca ttcacggcct aaaccaaatc    960
attaacttat acatccagaa gaaacagagt gaacagaaag ccgaacagaa ggaaactgga   1020
aagaagaaga tcaagtttaa taagaaagat tatccgacct tcacgtgctt acagaagcag   1080
atcctatcac aggtattccg caaggagatc atcattgaat cggaccgcga tttaattcgt   1140
gaactgaagt tctttgttga agagtctaaa gagaaggttg ataaagctag aggaattatc   1200
gaatttctgc tgaatcacga agagaatgat atcgatctgg ccatggtgta tctaccaaag   1260
tctaagatca acagctttgt gtataaagta ttcaaagagc ctcaggattt cttatctgtg   1320
tttcaggatg gcgcttccaa tctagacttc gtttcgttcg acaagatcaa gacccacctg   1380
gagaacaaca aacttactta caagatattc ttcaagaccc tgattaaaga gaaccatgat   1440
ttcgaatcgt tcttgatctt attacagcaa gaaatcgatc tgcttattga cggcggcgaa   1500
actgttactc ttggtgggaa gaaggagtcg attactagtc tggacgagaa gaagaataga   1560
ctgaaggaga agcttggctg gttcgaaggc aaagtccgcg agaatgagaa gatgaaagat   1620
gaagaggagg gcgagttctg cagcacggtt cttgcttatt cacaggcggt cctgaacata   1680
accaagcgtg ccgaaatatt ctggttgaat gagaagcaag acgcgaaagt tggcgaagat   1740
aacaaagata tgatattcta caagaaattt gacgagtttg ccgacgatgg cttcgcaccg   1800
ttcttctact ttgataaatt cggcaactac ctgaaacgcc gctccagaaa tacgaccaaa   1860
gaaatcaagt tacacttcgg caatgatgac ctgcttgaag gctgggatat gaacaaagaa   1920
cccgagtact ggtcattcat tctgagggat cgcaaccagt attatttagg tattgggaag   1980
aaagatggtg agatcttcca caagaagctt ggtaattctg tggaagcggt taaggaggca   2040
tatgagcttg agaatgaagc cgacttctac gaaaagatag actataaaca gttgaatatt   2100
gaccgattcg aaggtattgc ttttccgaag aagactaaga cagaggaagc gttcagacaa   2160
gtctgcaaga agagagcgga cgagttctta ggaggagata catacgagtt taagattctg   2220
ctggcgataa agaaagaata tgatgacttc aaagctcgcc gccagaaaga gaaggattgg   2280
gactctaaat ttagcaaaga gaagatgagc aaattaattg aatattacat tacttgcctt   2340
ggcaagcgcg atgattggaa gagatttaac cttaactttc gacagccgaa agaatatgaa   2400
gaccgctccg acttcgtgcg gcacattcaa cgtcaggcat attggattga ccctcgtaaa   2460
gtaagtaaag attacgtgga caagaaagtc gccgaaggtg aaatgttcct cttcaaagtg   2520
cataataaag acttctatga cttcgaaaga aagagcgaag acaagaagaa tcacactgca   2580
aatttgttta cacagtatct gctggagctc ttctcttgcg agaatattaa gaacatcaaa   2640
tcgaaagact tgatcgaatc tatcttcgaa ctggatggta aggcggagat ccgtttcagg   2700
cccaagaccg atgacgtgaa attaaagata taccagaaga agggtaagga tgttacgtac   2760
gctgacaaac gtgatggcaa caaggagaag gaggtgattc agcacaggcg gttcgcgaaa   2820
gacgcattaa ccctccacct caagattagg ttaaactttg ggaagcacgt gaatctgttc   2880
gacttcaaca aactggttaa tacagaactg tttgccaaag tgccagtaaa gatccttggc   2940
atggatcgcg gtgagaataa cctgatctac tattgtttcc tggacgaaca tggtgagatt   3000
```

```
gagaatggga agtgcggaag tctgaaccgc gtcggagagc aaattattac gctggaagat   3060

gacaagaaag ttaaggagcc ggtcgattac ttccagcttc tggtagatcg tgaaggtcag   3120

cgagattggg aacaaaagaa ttggcagaag atgacccgta tcaaagactt aaagaaagcg   3180

tatttgggta atgttgtcag ctggatctct aaagaaatgc tgagcggtat taaagaaggc   3240

gtggttacca tcggtgtact ggaggattta aactcgaact tcaagcggac gcgtttcttt   3300

cgagaacggc aggtctatca gggctttgag aaggcactag ttaataaatt gggttactta   3360

gtggataaga aatacgataa ctaccgtaat gtgtatcagt ttgctccaat cgttgatagc   3420

gttgaggaaa tggagaagaa caaacagatc ggcacccttg tgtatgtccc agcctcttac   3480

acctcaaaga tttgccctca tcctaaatgc ggttggcgcg agcgtctcta tatgaagaac   3540

tcagccagta aagagaagat cgtaggcctg ttaaagagcg acgggataaa gatctcctat   3600

gatcaaaaga atgaccgctt ctactttgaa tatcaatggg aacaggaaca taagagtgat   3660

ggaaagaaaa agaaatactc aggcgtagac aaagtcttct ctaatgtgag tcggatgcgc   3720

tgggatgtgg aacagaagaa atctattgac tttgtagatg gcaccgacgg cagcattacc   3780

aacaaactaa agagcctgtt gaaaggcaaa ggtattgagt tagacaacat caatcaacag   3840

attgttaatc agcagaaaga actgggagtg gagttctttc agagcatcat tttctacttc   3900

aatctgatta tgcagatccg taactacgac aaagagaagt caggctccga agcggactat   3960

atccagtgcc caagttgttt attcgattca cgcaaaccgg aaatgaacgg caaactgtca   4020

gcgatcacga acggagacgc aaacggcgcc tacaatattg cccgtaaagg cttcatgcag   4080

ctgtgtagga ttagagagaa tcctcaggaa cctatgaaac tgattaccaa ccgggagtgg   4140

gatgaagcag tgcgcgaatg ggacatctac tcagctgctc aaaagatccc ggttctttct   4200

gaggagaatt aa                                                        4212
```

<210> SEQ ID NO 14
<211> LENGTH: 3741
<212> TYPE: DNA
<213> ORGANISM: Artificial Sequence
<220> FEATURE:
<223> OTHER INFORMATION: Modified MAD nuclease nucleic acid sequence

<400> SEQUENCE: 14

```
atgttgaaga acgtaggcat cgatcgctta gatgtagaga aaggacgtaa gaatatgtct     60

aaactggaga aattcaccaa ttgttattca ctgagcaaga cactgcgatt taaagcgatc    120

ccggtcggca agacccagga gaacatcgat aataaacgcc tgctggtgga agatgagaag    180

cgagctgagg attataaggg tgtaaagaaa ctgctggatc gctactatct cagtttcatt    240

aatgacgtgc tgcacagtat caagctgaag aacttgaaca actatatcag cttatttcga    300

aagaagaccc gtaccgagaa agagaataag gaattggaga atctggagat taatctacgt    360

aaagagatcg ctaaggcgtt caaagggaat gagggatata aatcgctgtt caagaaagat    420

attattgaaa caatcctgcc ggaattcctt gacgataaag acgagatcgc gctcgttaac    480

tcgttcaacg gctttaccac tgcattcacc ggtttctttg ataatcggga gaatatgttc    540

tcagaggaag ccaagagtac ctctattgcg ttcaggtgca ttaatgagaa tctgaccagg    600

tatatttcta atatggatat ctttgagaaa gtggatgcca tatttgacaa gcacgaagtg    660

caggaaatca aagagaagat actgaattca gattacgatg tggaagattt ctttgaaggc    720

gagttcttca actttgttct aacacaggaa ggaatcgatg tatacaacgc gatcatcggc    780

ggtttcgtca cggagtcagg agaaaagatt aagggtttga atgaatacat taatttgtac    840
```

```
aatcaaaaga ccaaacagaa actgccgaaa tttaaaccac tgtacaaaca ggtgctgtcc    900
gaccgcgaat cattaagttt ctatggcgaa gggtacacct ctgacgaaga agtcctagaa    960
gtatttcgta acacgctcaa caagaattct gaaatattct cgtctatcaa gaagctggag   1020
aaattattca agaactttga tgagtattcc agcgccggaa tcttcgtcaa gaacggccca   1080
gccatctcta caattagcaa agatatattt ggtgaatgga atgtcatccg cgataagtgg   1140
aatgccgagt acgatgatat ccacctcaag aagaaggcag ttgttactga gaaatacgaa   1200
gacgatcgcc gcaagtcctt caagaagatc ggtagcttct cgctggaaca gctgcaggaa   1260
tatgcagacg cggatttatc tgtagttgag aagcttaaag agattattat tcagaaggtc   1320
gatgaaatct ataaagtgta tggtagtagt gagaagctgt ttgatgccga cttcgtcctc   1380
gagaagtcac taaagaagaa cgatgcggtg gtggctatta tgaaagatct gctggattcc   1440
gtgaaatctt tcgagaacta tattaaggcg ttctttggcg aaggcaaaga gaccaatcgt   1500
gacgaaagtt tctatggcga tttcgtactc gcctatgata ttcttcttaa ggttgatcac   1560
atttacgatg cgattcgcaa ctacgtaact cagaaaccgt attctaaaga taagttcaaa   1620
ctgtacttcc agaatccgca gtttatgggc ggctgggata aagacaaaga aaccgattac   1680
cgcgccacca tattgcgtta cggttccaaa tattatctgg cgattatgga caagaaatat   1740
gccaagtgcc tgcagaagat tgacaaggat gatgtaaacg gtaactacga aaagattaac   1800
tacaaactcc taccgggacc gaataagatg cttcccaaag tgttcttttc taagaagtgg   1860
atggcatatt ataacccaag tgaagatatt caaaagatct acaagaatgg cacgttcaag   1920
aaaggcgaca tgtttaattt gaatgattgt cacaaactga tagatttctt taaagactca   1980
atcagtcgct atcccaagtg gagtaacgca tacgatttca acttcagcga aaccgagaag   2040
tataaggata ttgcgggttt ctatcgcgag gtcgaagaac aaggctacaa agtttcattc   2100
gaatctgcgt caaagaagga ggtcgataaa ttggtggagg aagggaaact atatatgttt   2160
cagatctata ataaggactt ctctgacaag agccatggta ctccgaattt acacaccatg   2220
tacttcaaac tgctgttcga cgagaataac catggccaga ttcgactgag tggcggtgct   2280
gaattgttca tgcgtcgagc ttctctaaag aaagaagagc tggttgttca tcctgcgaat   2340
agtccgattg ccaacaagaa cccagataac ccgaaaaaga ctacaacttt atcttatgat   2400
gtgtacaagg acaaacgttt cagcgaagat cagtacgaac tgcatattcc aattgccatt   2460
aacaaatgtc ctaagaacat attcaagata aataccgagg tccgtgtact gctgaaacac   2520
gatgacaatc cgtatgtcat tggtattgac cgcggcgaac ggaacctgtt gtatattgtg   2580
gtagtggatg gtaaaggaaa tatcgtcgaa cagtattctc tgaatgaaat cataaataac   2640
ttcaacggca tccgcatcaa gaccgattac cattcactgc tggacaagaa ggagaaagaa   2700
agatttgagg cccgtcagaa ctggaccagc attgagaaca ttaaggaatt gaaagcaggt   2760
tatatctctc aagtggtcca taagatttgc gagttggtgg agaaatacga tgcggtgata   2820
gcgttagaag acctgaatag cggatttaag aactcaagag ttaaagtcga gaaacaagta   2880
tatcagaagt ttgagaaaat gcttatcgac aaattaaact acatggttga taagaaaagc   2940
aatccttgcg ccactggcgg tgcgcttaaa ggataccaga ttaccaataa attcgagtcg   3000
tttaagagta tgagcacgca gaacggcttc attttctaca tcccggcatg gttgacatcg   3060
aagattgatc catcaacggg attcgtgaat cttcttaaga ccaaatacac ttctatagct   3120
gattcgaaga aattcatctc ttcgttcgat cgtatcatgt acgtgcccga agaagatctg   3180
```

```
tttgaatttg ccctggatta taagaacttc tctcgcaccg atgccgatta catcaagaaa   3240

tggaaactgt acagttatgg taaccgcatc cgcatcttca gaaatcccaa gaagaacaat   3300

gtctttgatt gggaagaagt gtgtctgacc agtgcataca aagagttatt taataaatac   3360

ggcatcaact atcagcaggg cgatatccgt gctttactgt gcgaacagtc tgacaaagcc   3420

ttctacagtt ccttcatggc gttaatgagc ttaatgcttc agatgcggaa ttcgatcacg   3480

ggacgcaccg acgtggactt cctgatcagc ccagtaaaga atagtgacgg gatcttctac   3540

gatagccgga actacgaagc acaagagaac gcaatcttac cgaagaacgc cgatgcgaac   3600

ggtgcttata atattgcccg gaaagtcctt tgggccattg gccagttcaa gaaagcggag   3660

gacgagaaac ttgacaaagt taagattgcg attagcaata aagaatggct ggaatatgcg   3720

cagacgagtg tgaagcacta a                                             3741
```

<210> SEQ ID NO 15
<211> LENGTH: 3918
<212> TYPE: DNA
<213> ORGANISM: Artificial Sequence
<220> FEATURE:
<223> OTHER INFORMATION: Modified MAD nuclease nucleic acid sequence

<400> SEQUENCE: 15

```
atgaataaag cggccgataa ttacacgggc ggcaactatg atgagtttat cgccctttct     60

aaagttcaga agactctacg caatgagctg aaaccaactc cctttactgc cgagcacatc    120

aagcagcgtg gcattataag cgaagatgaa tatcgtgccc agcaatcatt ggagctcaag    180

aagatcgcgg atgaatatta ccgtaattat atcacacata agttaaacga tattaataat    240

ctggatttct acaacttgtt cgacgctatc gaagagaaat acaagaagaa tgacaaggat    300

aatagggaca aactggacct ggtggagaag agcaaacgtg gtgaaatcgc caagatgctg    360

agcgctgacg ataactttaa atccatgttt gaagcgaaac tgattactaa actgcttcct    420

gattatgtgg agcggaacta taccggcgaa gataaagaga aggctctgga aacactggcg    480

ctatttaaag ggttcacgac atacttcaaa ggatacttca agactaggaa gaacatgttc    540

tcgggcgagg gtggagcaag ttctatctgc catcgtatag tgaacgtgaa cgcctccatc    600

ttctacgata acctgaagac attcatgcgc atccaagaga aagcgggcga tgaaatcgca    660

ttaatcgaag aggaactgac ggagaagttg gatggctggc gtctggaaca tattttctcg    720

cgtgactatt acaatgaagt ccttgcgcag aaaggaattg actactataa ccagatctgc    780

ggcgacatta ataaacacat gaacctgtat tgccagcaga acaaatttaa agcgaatata    840

ttcaagatga tgaaattaca gaagcaaatt atgggtatca gcgagaaggt cttcgagatt    900

ccgccaatgt accagaacga tgaagaggtg tatgcttcgt ttaatgaatt tatttcccgc    960

cttgaggaag tcaaactgac cgatcgcctg cgtaatattc ttcagaacat caacatctac   1020

aacactgcta agatctatat caacgcgcgc tattacacca acgtcagtac ctatgtgtat   1080

ggcggttggg gggtgattga aagcgcaatc gaacgctatc tgtgtaacac tattgcaggt   1140

aaaggccaat cgaaggtgaa gaaaatcgag aatgcaaaga aggataacaa attcatgagc   1200

gtcaaggagt tggattcaat tgtggccgaa tatgagccgg attactttaa tgctccttat   1260

attgacgacg atgataacgc agtgaaagtc ttcggtggtc agggtgtgtt aggatacttt   1320

aataagatga gtgagctgct tgctgacgtt agtttgtata ccatcgacta taactcagat   1380

gacagcctga tagagaacaa agaaagcgct ctccgcatta agaaacaatt ggatgacatc   1440

atgagtttat atcattggct acagacgttc attatcgatg aggttgttga gaaagacaat   1500
```

```
gccttctacg ccgaactgga ggatatttgc tgcgaactag agaacgtggt caccttgtat   1560
gataggattc gaaactacgt gacccgtaaa ccgtactcga cccagaaatt taagcttaac   1620
ttcgctagtc cgaccctggc atccggctgg agccgctcta aggaattcga taacaatgct   1680
atcattctgc tgcgtaataa taaatattac atcgcgatat tcaatgttaa caataaacca   1740
gataaacaga tcatcaaggg cagcgaagaa caacgcttgt caacagatta taagaagatg   1800
gtttacaacc tactgcccgg tccaaataag atgttgccga aggtgtttat caaatccgac   1860
acgggcaaac gtgattataa cccgtcgtca tacatcctag aaggttacga aaagaaccgc   1920
cacattaaga gtagcggcaa cttcgatatt aactactgcc acgaccttat tgattattat   1980
aaagcttgca ttaacaaaca tcccgagtgg aagaattatg gatttaagtt taaggaaact   2040
aaccagtaca atgatatagg tcagttctat aaagatgttg agaagcaggg ctattccatc   2100
agctgggcgt atatcagcga agaggatata aacaagctgg atgaggaagg gaagatctac   2160
ctgtttgaaa tctacaataa agatttgtca gctcattcaa caggtcgtga taacctgcat   2220
accatgtacc tcaagaatat attttctgaa gacaacctaa agaacatctg tattgaactt   2280
aacggcgaag ccgagttatt ctatcgtaag agttcaatga aatcgaacat aactcacaag   2340
aaagatacca tcctggttaa taagacctat atcaacgaaa ctggcgttcg cgtgtctctt   2400
tctgatgaag actatatgaa agtatataac tattacaaca ataactacgt tatcgacacc   2460
gagaatgata agaacctgat tgacatcatt gagaagatag ggcacaggaa gtcaaagata   2520
gacatagtga aagataaacg ctacacagaa gataaatact tcctttattt accgattacg   2580
attaattatg gcattgagga tgagaatgtc aacagtaaga tcatcgaata tatcgccaaa   2640
caggacaaca tgaacgttat cggtatagat cgtggagaac gcaacttaat ttatatatct   2700
gtgattgaca ataaaggtaa catcatcgaa cagaagtctt tcaatttggt gaacaactac   2760
gactacaaga ataaacttaa gaacatggag aaaacccgcg ataatgctag aaagaactgg   2820
caggaaattg gaaagatcaa agatgttaag agcggctatc ttagtggcgt catatccaag   2880
atcgctcgta tggtaattga ttataacgcc atcattgtta tggaagatct gaataaaggc   2940
tttaagaggg gacggtttaa agtagaacgc caggtatacc agaagttcga gaatatgctg   3000
atcagtaagc tgaactacct ggtatttaaa gaacgtaagg ctgatgagaa tggtggtatc   3060
ctccgtggtt atcaattaac ttacattcct aagagtatta agaacgtcgg taaacaatgc   3120
ggttgcatct tctatgttcc tgctgcatat acttctaaga tcgacccggc aacagggttt   3180
atcaatatct tcgattttaa gaaatattca ggttcaggta tcaacgcgaa ggtgaaagat   3240
aagaaggaat tcctcatgtc aatgaattct atccgctata ttaatgaagg cagcgaagaa   3300
tatgagaaga taggccatag agaactgttt gcctttagct ttgattataa caactttaag   3360
acttataacg tttctagtcc ggttaacgag tggaccgcct acacctacgg cgaacggatc   3420
aagaaactgt acaaggatgg tagatggctg cgtagcgaag tgctgaacct gactgagaat   3480
cttatcaaac tgatggaaca gtataacatc gaatataagg atggccatga tattcgtgaa   3540
gacattagtc atatggatga aacacgcaac gcagacttca tttgcagcct attcgaagag   3600
ctgaaatata ctgttcagtt gcgtaatagt aaatccgagg ctgaagacga gaattatgac   3660
cgactggtta gtcccatact gaatagctcg aacggcttct atgattcgag cgactatatg   3720
gagaatgaga ataacacgac gcatacgatg ccaaaggacg cagatgccaa cggtgcctat   3780
tgtattgcgt tgaaagggct ctatgagatt aataagatta agcagaattg gagcgacgac   3840
```

aagaagttca aagagaacga gctgtacatt aacgttacgg aatggttaga ttacattcag 3900
aatcgtcgct tcgaataa 3918

<210> SEQ ID NO 16
<211> LENGTH: 3819
<212> TYPE: DNA
<213> ORGANISM: Artificial Sequence
<220> FEATURE:
<223> OTHER INFORMATION: Modified MAD nuclease nucleic acid sequence

<400> SEQUENCE: 16
atggaagata aacagtttct cgaacgttac aaggaattta ttggtctcaa ttccctgagt 60
aagaccctgc gcaactcgct gatcccagtc ggcagcacac ttaagcacat tcaagaatat 120
ggtattctgg aggaagatag cttacgcgct cagaaacgcg aagagctgaa aggtattatg 180
gatgattact atcggaacta tattgaaatg caccttcgtg atgtccatga cattgattgg 240
aacgagctgt ttgaagcgtt aacggaagta aagaagaacc agacagacga cgcaaagaaa 300
tgcctagaga agatacagga gaagaagagg aaggagatct accagtattt gagcgatgac 360
gcggtattct ccgaaatgtt caaagagaag atgatttcag gtattctacc agactttatt 420
cgttgtaacg aagagtatag cgaagaagag aaagaagaga aactaaagac agttgccctg 480
tttcaccggt tcacgagttc cttcaacgat ttcttcctga accgtaagaa cgtcttcacg 540
aaagaggcca ttgctacagc tattggttat cgcgtagtgc atgagaatgc tgaaatcttt 600
cttgagaaca tggttgcctt tcagaacatt cagaagtctg ctgagagtca aattagcatc 660
attgaacgaa agaacgaaca ctacttcatg gaatggaaac tgtcccatat cttcacagcg 720
gattactata tgatgcttat gacgcagaag gcgatcgagc actataacga gatgtgtggc 780
gtcgtaaatc agcacatgaa agaatactgt cagaaggaaa agaagaattg gaatctttac 840
cgtatgaaac gcttgcacaa acagattctg tcaaacgcga gcacctcttt taagattccc 900
gagaagtacg agaatgatgc ggaggtgtac gaaagcgtga actccttctt acagaatgtg 960
atggaaaaga ccgttatgga acgtatcgct gtactgaaga acaacaccga caactttgac 1020
ctttccaaga tctacataac cgcgccctac tacgagaaaa tttctaacta tctgtgtggt 1080
tcgtggaaca ccatcgccga ctgtctgact cactattacg aacaacagat cgcgggcaaa 1140
ggcgctcgca aagaccagaa agtgaaagct gcggtgaagg cggataagtg gaagtcgctg 1200
tcggaaatcg agcagttact taaagaatac gcccgggctg aagaggtcaa acgtaaacct 1260
gaagagtaca tcgcagaaat agagaacatt gtctctttga aggaagtcca cttgctggaa 1320
tatcatccgg aagttaacct gatcgagaac gagaagtatg ctacagaaat caaagatgta 1380
ctggacaact atatggaatt atttcattgg atgaaatggt tctatatcga agaagctgtg 1440
gagaaagaag ttaatttcta cggtgaattg gatgatctct atgaagaaat tcgtgatatt 1500
gtcccgttat ataacaaagt gcgcaattat gtgacccaga aaccgtatag tgataccaag 1560
attaaactaa actttggtac gccgacccta gccaatgggt ggtccaagtc gaaagaatac 1620
gattataacg cgattctgct tcagaaagac ggcaagtact atatgggtat cttcaatccg 1680
gtgcagaaac cggagaaaga aatcattgaa ggacattcgc atcctttgga aggcaatgaa 1740
tacaagaaaa tggtttatta ttacttaccg tccgcgaaca agatgctgcc caaggttctt 1800
ctttctaaga aagggatgga aatataccag ccgagcgagt acatcattaa tggttataaa 1860
gagcgtcgcc atatcaaatc ggaggagaaa tttgatttac agttctgtca tgacttgatt 1920
gattatttca aatcaggcat tgaacgcaac ccggattgga aagtgtttgg ctttcacttc 1980

```
tcggacaccg acacgtatca agacatatct ggcttctata gggaagtgga ggatcagggc   2040
tacaagatcg attggactta tatcaaagaa gccgatatag atcgtttaaa cgaagaaggc   2100
aaattatatc tcttccagat ctataacaaa gacttcagtg agaaatcgac aggacgcgag   2160
aaccttcaca caatgtatct taagaatcta ttttccgaag agaacatacg cgaacaagtt   2220
cttaagttaa acggtgaagc ggagatattc tttcggaaga gcagtgtgaa gaaaccaata   2280
atccacaaga aaggtacgat gttagtgaac aggacgtaca tggaagagat gcatggcgag   2340
agtgtaaaga agaatatacc ggagaaagag taccaagaaa tttataacta catgaaccat   2400
cggtggaaag gtgagcttag cgctgaagcg aaagagtatc tgaagaaagc agtttgtcac   2460
gaaacgaaga aagatattgt taaagattat cgttatagcg tcgataagtt cttcattcac   2520
cttccgatca cgattaacta tcgtgcaagt ggcaaagaag cgttgaattc agtagctcag   2580
cgctatatcg cgcaccagaa tgatatgcat gtgattggta ttgaccgtgg agagagaaat   2640
cttatttatg ttagcgttat caacatgcag ggagaaatca ttgagcagaa atctttcaac   2700
gttgtgaata aatataatta caaagagaag ctgaaagaac gcgaacagaa tcgtgacgag   2760
gctcggaaga attggaaaga gattggccag attaaagatc tcaaggaagg ttatctaagc   2820
ggcgtaatcc atgaaattgc caagatgatg attaaatacc atgcaatcgt ggcgatggaa   2880
gaccttaatt acgggttcaa gagggggaga ttcaaagttg aacgacaggt atatcagaag   2940
ttcgagaaca tgctgattca gaaattgaat tatctggtat ttaaggatcg tagcgccgat   3000
gaggatggcg gtgttctgcg tggataccag ctggcctaca ttcctgatag tgtaaagaaa   3060
ttaggacgcc aatgcggaat gattttctat gtgccggcag cattcacgag caagattgat   3120
ccagctacgg gcttcgtcga tatcttcaac cacaaggcat acacgacaga ccaagcgaag   3180
cgtgagttta tattaagctt tgatgaaata tgttatgatg tggaacgtca actgttccgc   3240
tttacattcg actacgccaa ctttgcgaca cacaacgtga cattagcacg taataattgg   3300
actatctata ccaacggtac gcgtacccag aaggaatttg tgaaccgtcg tgtccgcgac   3360
aagaaagaag tatttgaccc taccgagaag atgttaaagt tgttagaact ggagggtgtt   3420
gagtaccaga gtggcgcgaa tcttcttcca aagttggaga agatcagtga tcctcacctg   3480
tttcatgagc tgcagcgcat tgtacgcttc acggtacagc tgcgcaattc gaagaacgaa   3540
gagaatgatg tggattacga ccatgttata tctcccgtac tgaatgaaga gggcaaattc   3600
tttgactcaa gtaagtacga gaacaaagaa gaaaagaagg agtcattact gcctgtagat   3660
gcggacgcta acggcgccta ttgcatagct ttgaaaggcc tttacattat gcaggcaata   3720
cagaagaatt ggtcggaaga gaaagccctg agtcccgatg tcttacgcct gaataataac   3780
gactggttcg attacattca gaacaaacgc tatcggtaa                          3819
```

<210> SEQ ID NO 17
<211> LENGTH: 3864
<212> TYPE: DNA
<213> ORGANISM: Artificial Sequence
<220> FEATURE:
<223> OTHER INFORMATION: Modified MAD nuclease nucleic acid sequence

<400> SEQUENCE: 17

```
atgaataata acactaataa ttctttcgaa ccgttcatcg gcggaaattc agttagtaag     60
accttgagaa atgagttacg ggttggaagc gagtatacag gtaaacacat taaagaatgc    120
gcgatcattg cggaggatgc cgtcaaagct gagaatcagt atatcgttaa agaaatgatg    180
```

```
gatgacttct atcgggactt catcaaccgc aaactggatg cgttacaagg tatcaactgg    240

gagcaattgt ttgacattat gaagaaagcg aaactggata agagcaacaa agtgtctaaa    300

gaattagata agattcagga atcaacgcgc aaagagattg tcaagatatt tagtagtgat    360

cccatttata aggacatgct aaaggcagat atgattagta agattctgcc tgaatacatc    420

gttgataaat acggcgatgc tgcaagccgc attgaagctg tgaaggtctt ttacggattc    480

tcaggctact tcatcgattt ctgggcttct cgtaagaacg tgtttagcga taagaatatt    540

gcttctgcga taccgcaccg tattgtcaat gttaatgctc gtatccatct cgacaacatc    600

acggcgttta atcgtattgc ggagattgcg ggagatgagg tagccggaat tgccgaggac    660

gcgtgcgcat atttgcagaa tatgagcctg gaagacgtgt ttactggtgc atgttatggt    720

gaattcattt gccagaagga tattgatcgc tataataata tttgcggcgt gattaatcaa    780

catatgaacc agtattgtca gaataaaaag atcagtcgtt ccaaattcaa gatggagcgt    840

cttcacaaac agattctgtg tcgcagtgaa tcaggtttcg aaatcccgat tggattccaa    900

accgacggcg aagttattga tgcaattaat agcttctcaa ctattcttga agagaaggac    960

attctggatc gcctgcggac tttgagccaa gaagtaactg ggtacgacat ggagcgcatt   1020

tatgtgtcgt ctaaagcctt cgaatcggtg agcaagtaca ttgatcacaa gtgggatgtt   1080

atcgcaagca gcatgtacaa ttacttctca ggtgcggttc gcggcaaaga cgataagaaa   1140

gatgcgaaga tccagactga aattaaaaag atcaagagct gttctctgtt agatttaaag   1200

aaattagtgg acatgtatta caagatggat gggatgtgtc tggaacacga agccacagag   1260

tacgtggcgg gtattacgga gatcctggtg gacttcaact acaagacctt cgatatggac   1320

gatagtgtaa agatgatcca gaatgaacat atgataaatg agatcaaaga atatctcgac   1380

acgtacatgt caatttatca ttgggcgaaa gactttatga tcgacgagct agtcgaccgc   1440

gatatggagt tctactccga attagatgag atttactacg acctttcaga tattgtcccg   1500

ctgtacaaca aggtacgcaa ttatgttact cagaaaccgt acagccaaga caagatcaaa   1560

ctgaactttg gctctccgac cctggctaac ggatggagca aatccaaaga atttgacaac   1620

aatgttgtgg tgctgctgcg tgatgaaaag atctacttag cgatactaaa tgtcggtaac   1680

aagccttcca aagacatcat ggcaggcgag gaccgccgtc gcagtgatac ggattacaag   1740

aagatgaatt actatttact gcccggtgcg tcaaagaccc tcccacacgt gttcatctcg   1800

tctaacgcgt ggaagaaaag ccatggcatc ccggatgaga ttatgtacgg atataaccag   1860

aataagcacc tgaaatcttc tccgaacttt gatctggaat tctgccgaaa gcttattgat   1920

tattacaagg aatgcataga tagctatcct aactaccaga tcttcaactt taaattcgct   1980

gccaccgaga cctataatga tatttcagag ttctataaag atgttgaacg ccagggttat   2040

aagatcgaat ggagttatat atcagaggat gacattaatc agatggaccg cgatggtcag   2100

atctacctct tccagattta taacaaagac ttcgcgccga actcgaaggg tatgcagaac   2160

ctccacactc tgtatttgaa gaatatattc agtgaggaga atctgagcga cgtcgttatt   2220

aagctcaacg gcgaagccga gcttttcttt cgtaaatcat caatccaaca caaacgtggg   2280

cataagaaag gttccgttct cgttaataag acctacaaga ccacagagaa gacagagaac   2340

ggtcagggcg aaatcgaagt aattgagagc gtcccggatc agtgctatct tgaactcgtg   2400

aaatactggt ctgagggtgg cgtgggtcag ctgagcgagg aagcctctaa atacaaggac   2460

aaagtgtctc actatgcagc gaccatggat attgttaaag atcgccgtta tactgaagac   2520

aaattcttta ttcacatgcc gatcaccatt aatttcaaag ccgataaccg caacaacgta   2580
```

aacgagaagg tgctgaaatt tattgcggag aacgacgacc tccacgtaat tgggattgac 2640
cgtggtgaac gtaatttgtt gtatgtaagc gtcattgact cccgcggacg tattgtagaa 2700
cagaagtcct ttaacatcgt tgagaactac gagagcagca agaacgtcat tcgaaggcat 2760
gattataagg gcaaacttgt caataaagaa cactaccgaa acgaggccag gaagtcctgg 2820
aaagaaatag gcaagataaa ggagatcaaa gaaggctatc tgtcacaggt tatccatgaa 2880
atctcgaaac ttgtgctgaa gtacaacgca atcatcgtca tggaagacct aaactatggg 2940
tttaaacgtg gcaggtttaa agtggaacgt caggtgtatc agaaatttga aaccatgctg 3000
attaataaac tggcgtacct tgtagataaa tcacgcgccg tagatgaacc gggcggacta 3060
ctgaaaggtt atcagctgac ctatgttccg gataacctgg gtgaactggg aagccaatgc 3120
ggcattattt tctatgttcc agcagcttac acctccaaga ttgatccagt gaccgggttc 3180
gtcgatgtat ttgactttaa agcatatagt aatgccgaag cccgattaga cttcattaac 3240
aaattagact gcatccgtta tgatgcctca cgcaataaat ttgagatcgc cttcgattat 3300
ggtaatttcc gcacccatca tactacatta gcaaagacgt cttggacaat ctttattcat 3360
ggcgatcgca tcaagaagga acgtgggtcc tatggctgga aggacgaaat aattgacatt 3420
gaagcccgaa tccgtaaact atttgaagac accgacatcg agtatgccga tggccacaac 3480
ttaattggcg atattaatga actggaatca cccattcaga aaaaattcgt tggagaatta 3540
ttcgacataa tccgcttcac ggtccagcta cgcaactcga agagcgagaa atatgatgga 3600
accgagaagg aatatgataa gattatctcg ccggtgatgg atgaagaggg tgtgtttttc 3660
accaccgatt cctatatccg cgcggacggc acagaactac ctaaagatgc agatgcaaat 3720
ggcgcatatt gtatagccct gaaaggtctg tatgacgtct tagccgtgaa gaaatactgg 3780
aaggaaggcg agaaattcga tcggaagctg ctcgcgatca caaattataa ttggtttgac 3840
ttcatacaga accgtcggtt ctaa 3864

<210> SEQ ID NO 18
<211> LENGTH: 3693
<212> TYPE: DNA
<213> ORGANISM: Artificial Sequence
<220> FEATURE:
<223> OTHER INFORMATION: Modified MAD nuclease nucleic acid sequence

<400> SEQUENCE: 18
atgcatgaga acaatgggaa gattgctgac aactttattg gtatctaccc ggtatctaag 60
acattgcgct tcgaactgaa acccgttggt aagacacagg aatacatcga gaaacacggc 120
attctggacg aagatctgaa acgtgcaggc gactacaaga gcgtaaaaaa gataattgac 180
gcgtatcata aatacttcat agatgaggcg ctgaatggca ttcaactgga cggattaaag 240
aactactatg aattatacga aaagaaaaga gataacaatg aggagaaaga attccagaaa 300
atccagatgt cgctgcggaa acaaatagtt aaacgtttct cagaacatcc gcagtataag 360
tatttattca agaaagaact gatcaagaac gtcctcccag aatttactaa ggataatgcg 420
gaagagcaaa cgctggtgaa gagcttccag gaattcacaa cttacttcga aggcttccac 480
cagaatcgta agaacatgta ttcggatgaa gagaagtcga ccgcgattgc gtatcgtgtc 540
gtgcaccaga acctccctaa atatatcgac aacatgcgca tcttctcaat gattctgaac 600
acagacatta gaagcgactt aaccgaatta ttcaataacc taaagactaa gatggatatt 660
acgatcgttg aagaatactt cgcgattgat gggttcaata aagtggtaaa tcagaaggga 720

```
atagacgttt acaatacaat tctaggcgcc ttctcaactg atgacaatac gaagattaaa    780
ggcctgaacg agtatatcaa cctgtacaat cagaagaaca aagcgaagct gccgaagctg    840
aaaccgttgt ttaaacagat tctcagcgat cgtgataaga taagcttcat tccggaacag    900
tttgatagtg ataccgaagt gctagaagcg gtagatatgt tctacaatag attactgcag    960
ttcgtgatcg agaacgaagg tcagatcacg attagtaagc tcttgaccaa cttctctgcc   1020
tacgatctta acaagatcta cgtcaagaac gatactacta ttagcgctat cagcaatgac   1080
ttattcgatg actggagcta cattagcaaa gccgtacgtg agaactacga tagcgagaac   1140
gttgacaaga acaagcgcgc ggcagcgtat gaggagaaga aagagaaagc tctgagcaag   1200
atcaagatgt attcaattga agaactgaat ttctttgtca agaagtatag ttgtaacgaa   1260
tgtcacatag aaggctattt cgaacgcagg atcttggaaa tcctcgataa gatgcgctac   1320
gcgtacgaat cctgcaagat cttgcatgat aaaggcctga ttaacaacat tagtctgtgc   1380
caggaccgtc aagccatttc ggagcttaag gacttcctcg atagtatcaa agaggtccaa   1440
tggttactga aacctctgat gattggccag gaacaggcag ataaggaaga agccttctat   1500
acggaactct tacggatctg ggaagaatta gaaccgatta cgctgctgta taataaagta   1560
cgtaattacg taacaaagaa accgtacacc ctcgagaagg tcaagttaaa cttctataag   1620
agcactctgc ttgacggttg ggataagaat aaagagaaag acaacctggg cattattctg   1680
ctgaaagatg ggcagtatta tttgggaatt atgaatcgtc gtaacaacaa gattgccgat   1740
gatgcgccat tagctaagac agataatgta tataggaaga tggaatataa attacttacg   1800
aaagtgtctg caaacctgcc tcgcatattt cttaaagata aatataatcc gtcggaggaa   1860
atgctggaga agtacgagaa agggacccat ctcaagggtg agaatttctg catagatgat   1920
tgtcgcgaac tgatcgactt cttcaagaaa gggattaaac agtatgaaga ttggggccag   1980
tttgacttca aatttagcga tacagaaagc tatgatgata tttcagcctt ctataaagaa   2040
gtggagcatc aaggctacaa gatcaccttt agagacatag atgaaacgta catcgatagt   2100
ctggtcaacg aaggcaaact ttatttattt caaatctaca acaaggattt ctcaccgtac   2160
tctaaaggaa cgaagaacct ccatacctta tactgggaaa tgctctttag tcaacagaat   2220
ctgcagaata tcgtgtacaa actgaatgga aacgcggaaa tattctaccg taaagcaagc   2280
attaatcaga aagacgttgt cgtacacaag gcggacctcc caataaagaa taaagaccct   2340
cagaacagca agaaggagag tatgtttgat tatgatatca ttaaggacaa gcgattcacg   2400
tgcgataaat atcaatttca tgttcctatt accatgaact tcaaagccct tggtgagaat   2460
cactttaatc gcaaggtgaa ccgcttaatc cacgatgccg agaatatgca cattattggg   2520
attgatcgtg gagaacgtaa tcttatctat ctgtgtatga ttgatatgaa aggtaacatt   2580
gtaaagcaga ttagtcttaa cgagatcatc agctacgata agaataaatt agaacacaag   2640
cgtaactatc accagctgct caagacacgg gaagacgaga ataaatctgc ccgccagtca   2700
tggcagacca ttcataccat taaagaatta aaggagggct acttatcgca ggttattcat   2760
gtcatcacgg atctaatggt agaatataat gctattgttg ttctggaaga tcttaacttc   2820
ggcttcaaac agggtcgcca gaagtttgaa cgccaggtgt accagaagtt tgagaagatg   2880
ctgattgata aactgaatta ccttgtggac aagagcaaag ggatggatga agacggaggt   2940
cttctacacg cttatcagct cacggatgaa tttaagagct ttaagcagtt aggcaaacaa   3000
agcggcttcc tttactatat tcccgcatgg aatacttcta aattagatcc cactactggt   3060
ttcgtaaatt tattctatac gaaatacgaa tcggtggaga agagtaagga atttatcaat   3120
```

```
aacttcacca gcattctcta taaccaggag cgggaatact tcgaatttct ctttgattac   3180
tcggccttca caagcaaagc tgaaggaagc cgtctgaaat ggacagtgtg ttctaaaggc   3240
gagcgtgttg agacctatcg caatccgaaa aagaacaacg agtgggacac gcaaaagatt   3300
gatcttacct ttgagctaaa gaaattattt aatgactatt caattagcct gttggacggt   3360
gatttaagag aacagatggg taagatcgat aaagcagact tctacaagaa atttatgaaa   3420
ttattcgccc tgattgtcca gatgcgaaat tccgatgagc gtgaagacaa actgatttca   3480
ccggttctga ataaatatgg tgctttcttt gaaactggaa agaacgagcg gatgccgctg   3540
gacgcggacg cgaacggagc gtacaatatt gcgcgtaaag gcctttggat tattgagaag   3600
attaagaata ccgatgttga acagcttgat aaggtgaaac tcaccattag taacaaagag   3660
tggcttcagt atgcgcagga gcatatctta taa                                3693
```

<210> SEQ ID NO 19
<211> LENGTH: 3708
<212> TYPE: DNA
<213> ORGANISM: Artificial Sequence
<220> FEATURE:
<223> OTHER INFORMATION: Modified MAD nuclease nucleic acid sequence

<400> SEQUENCE: 19

```
atggttgcct ttatcgatga attcgtaggt cagtacccag tttcaaagac ccttcgcttc     60
gaagcacgtc cggttccaga gacgaagaaa tggttggaat cggatcaatg ttccgtcctc    120
tttaacgacc agaagcgcaa cgaatactac ggtgtactta aggaactgct ggacgattac    180
tatcgcgcgt atattgaaga tgccctgacc tccttcacgc tagataaagc cttgctcgag    240
aacgcgtatg atctgtattg taaccgtgat acgaacgcct tctcttcatg ctgcgagaag    300
ctacgtaaag acctggtcaa ggcatttgga aacttgaagg actacctgtt aggctcggat    360
cagttgaagg atctggttaa gctgaaagca aaggttgatg cacctgcggg caagggaaaa    420
aagaaaattg aagtggactc tcgtttaatt aattggttaa acaataacgc gaaatactct    480
gcagaagacc gtgagaagta cattaaggcg attgaatctt tcgaaggctt cgttacctat    540
ctgactaatt ataaacaggc tcgcgagaat atgtttagca gtgaagacaa gagcaccgcg    600
atcgcgttta gagtgattga ccagaacatg gtgacctatt tcggcaatat cagaatatat    660
gagaagatca aggcgaagta tcccgaatta tatagcgcgc tgaagggctt cgagaagttt    720
ttctcaccca ccgcgtatag tgaaatcctc tcccaaagta agattgatga atataactac    780
caatgtattg gccgcccgat tgacgatgcc gactttaagg gcgtgaacag ccttataaat    840
gaatatcgcc agaagaacgg catcaaagca cgcgaactgc cggttatgtc tatgctttat    900
aaacagatcc tatcagacag agataactcg tttatgtccg aggtcataaa tcgtaacgag    960
gaggcgattg agtgcgctaa gaatggatac aaggtatcat acgcgctgtt taacgagctg   1020
ctgcagctgt ataagaaaat attcacagaa gacaactacg gcaatatcta tgttaagact   1080
caacctctta ccgaacttag tcaggcgctc ttcggcgatt ggagcatcct gcgcaatgcc   1140
ttggacaacg gtaaatatga caaagacatc attaatttag cggagttgga gaaatacttc   1200
agcgaatact gcaaggttct ggacgcagat gacgcagcga agattcagga caagttcaac   1260
cttaaagatt atttcatcca gaaaaacgcc ctggatgcga cactcccgga tctggataag   1320
attacgcagt acaagccgca tttagacgcc atgctacagg cgatccgcaa atacaagcta   1380
ttctcgatgt acaacggcag gaagaaaatg gacgttccgg agaacggtat cgatttcagt   1440
```

```
aacgaattta acgccatata tgataagctt tctgaattct caatcttgta tgaccgtatc   1500
cgcaatttcg cgaccaagaa accttactcc gatgagaaga tgaaactgtc ctttaatatg   1560
cctaccatgc tggcaggctg ggattacaac aatgagaccg caaatgggtg ctttctcttc   1620
atcaaggacg gcaaatactt cttaggtgtt gcggacagta aaagtaagaa tatcttcgac   1680
tttaagaaga atccgcatct attagacaaa tattcctcta aggatattta ctacaaagtg   1740
aagtataaac aggtatctgg gtccgccaag atgctgccga aagtcgtctt tgctggttcg   1800
aacgagaaga tctttggtca tttgattagc aaacgcattc tggaaatccg tgagaaaaaa   1860
ctatacactg ccgctgccgg tgatcgcaag gccgttgcag agtggattga cttcatgaaa   1920
tctgcgattg ctattcaccc ggagtggaac gaatacttca agttcaagtt taagaacacc   1980
gcagaatatg ataacgcgaa taaattctat gaagacattg ataaacaaac ctatagtcta   2040
gagaaagtcg aaatacctac ggaatatatc gacgaaatgg tgtcccaaca taagctctac   2100
ctgtttcagc tttatacgaa agatttctcg gacaagaaaa agaagaaggg tacagacaat   2160
cttcatacaa tgtactggca cggtgtcttt agcgatgaga atctgaaagc cgtgactgaa   2220
ggtacgcaac ccatcattaa actgaatgga gaggccgaga tgttcatgcg caacccgagc   2280
atcgaatttc aggttacaca tgagcacaac aaacccatag cgaacaagaa cccgttaaac   2340
acgaagaagg aatcggtatt taattacgat ttaatcaaag ataaacgcta cactgaacgt   2400
aagttctact ttcattgtcc tatcactctg aacttccgcg ccgataaacc cattaaatac   2460
aatgagaaga tcaatcggtt cgtggagaac aacccggacg tctgcattat aggtatcgat   2520
cgtggagagc gtcacctgct gtattataca gtgatcaatc agaccggcga tattcttgag   2580
caaggaagtt tgaacaagat cagcggcagc tatacgaacg ataaaggtga gaaggtgaac   2640
aaagaaaccg attaccatga cctgctggat cggaaggaga aggaaagca tgttgcgcag   2700
caggcatggg aaacaattga gaacatcaaa gaactcaagg cgggttattt aagccaggta   2760
gtgtataaac tgacccagtt aatgttgcag tacaacgcgg tgattgttct ggagaatctc   2820
aatgttggat tcaaacgtgg ccgtacgaaa gtcgagaagc aggtctatca gaaattcgag   2880
aaggcgatga tcgacaagtt aaattacttg gtctttaaag atcgtggtta tgagatgaac   2940
ggtagctacg ctaagggtct gcagctaact gataaatttg aatcgtttga caagattggt   3000
aagcagacgg gatgtattta ttatgttata ccgtcttata cgagccatat tgaccctaag   3060
acgggattcg tgaacctgct aaatgcgaaa ctacgctatg agaatataac gaaagcacaa   3120
gataccattc gtaaatttga ttcgattagc tacaacgcta aagcggatta tttcgagttt   3180
gcattcgatt accgttcatt tggcgtcgat atggcccgta atgaatgggt ggtatgcacg   3240
tgcggtgact tacgctggga atattccgcc aagacacgtg aaaccaaagc gtattcggtg   3300
accgaccgtc ttaaagaact cttcaaggcg cacggtattg attacgtcgg aggcgagaat   3360
ttagtatcgc acattaccga ggtcgcagat aaacatttcc tgtcgactct gctgttctat   3420
ttacggttgg ttcttaagat gcgttatacc gtcagcggca ccgagaacga gaatgacttt   3480
atactctcgc cggttgagta cgcaccaggg aagttctttg actcacgcga ggccactagc   3540
accgaaccga tgaatgcaga cgcaaatggt gcttatcata ttgcgcttaa gggattgatg   3600
acaattcgtg gaattgaaga cggcaagtta cacaactatg gtaaaggagg cgagaacgct   3660
gcctggttca aatttatgca gaaccaagaa tacaagaata atggttaa                3708
```

<210> SEQ ID NO 20
<211> LENGTH: 3780

<212> TYPE: DNA
<213> ORGANISM: Artificial Sequence
<220> FEATURE:
<223> OTHER INFORMATION: Modified MAD nuclease nucleic acid sequence

<400> SEQUENCE: 20

```
atgaattata agaccggcct ggaagatttc atcggcaaag aatctttaag taagacgctg     60
cgcaatgcgt tgattccaac agaaagtacg aagattcaca tggaagaaat gggcgtgatt    120
cgtgacgatg aactgagagc ggagaaacag caggaactga aggaaatcat ggacgattat    180
tatcgcgcgt ttatagaaga gaagctcggt cagatacaag gaattcagtg gaacagccta    240
tttcaaaaga tggaggagac catggaggat attagtgtga ggaaagatct ggataagatt    300
cagaacgaga aacgcaaaga gatttgttgc tacttcacta gcgataagcg attcaaagac    360
ctgtttaatg cgaaattaat caccgatatc ctgccaaact tcattaaaga taacaaagaa    420
tatacggaag aagagaaggc agagaaagaa caaactcgcg tattgttcca gcgctttgct    480
accgcattca ctaactactt taaccagcga cgtaataact ttagtgaaga caatatttcg    540
accgcaatct catttcgcat cgtgaatgag aattctgaga ttcatctgca gaatatgcgt    600
gccttccagc gcattgagca gcagtacccg gaagaagtct gtggcatgga ggaagaatat    660
aaagatatgc ttcaagaatg gcaaatgaag catatttact ctgtggattt ctatgatcgc    720
gaacttactc agccaggaat agagtactat aacggcattt gcggaaagat taatgagcac    780
atgaatcaat tctgtcagaa aaaccgcatt aataagaatg acttcagaat gaagaaattg    840
cacaaacaaa tattatgcaa gaaatctagt tactatgaaa taccattccg ctttgaatcc    900
gaccaagaag tatatgacgc attgaatgag tttataaaga caatgaagaa gaaagaaatt    960
attcgccgtt gtgttcactt gggtcaggaa tgcgacgact acgacttagg aaagatctac   1020
attagcagca ataaaatatga gcagataagc aatgctttgt atggatcttg ggacaccatt   1080
cgtaaatgca tcaaagaaga atacatggat gcgttaccgg gcaaaggcga gaagaaggaa   1140
gagaaggcag aagctgccgc caagaaggag gaatatcgca gtatagctga tattgacaag   1200
attattagcc tctacggaag tgagatggac cggaccataa gcgccaagaa atgcattaca   1260
gagatctgcg atatggcggg ccaaattagc atcgacccgc ttgtgtgtaa ctccgacatt   1320
aaactgctgc agaataagga gaagaccacg gagattaaga cgattctgga ctcgtttctg   1380
catgtttatc aatggggcca gacatttatc gtaagcgata ttattgagaa ggacagctat   1440
ttctacagtg aacttgaaga tgttctagaa gactttgaag gtattactac cctgtataac   1500
cacgtgcgta gctatgtgac ccagaagccg tatagtaccg tcaaattcaa actccacttt   1560
gggtcgccga cgctggcaaa cggttggagt cagtccaagg aatatgataa taatgccatc   1620
ctgctgatgc gcgaccagaa attctacctg ggcatattca acgttcgtaa taaaccagac   1680
aaacaaataa ttaaaggaca cgagaaagaa gagaagggcg actacaaaaa gatgatctat   1740
aacctgctgc ctggtccgtc gaagatgctg cctaaggtgt tcataaccag ccgctccggc   1800
caggagacct ataagcctag caaacatatc ttggatgggt ataatgagaa acgtcacatc   1860
aaatcatctc ccaagtttga tctgggctat tgttgggatt tgatagatta ttataaggaa   1920
tgcattcaca agcacccgga ttggaagaat tatgactttc acttctccga caccaaagat   1980
tacgaggata ttagcggatt ctatagagaa gtagaaatgc agggctacca gattaagtgg   2040
acgtatatct cagcagatga aatccagaag cttgacgaga aaggccaaat attcctgttt   2100
cagatctata acaaagactt ctcggtacat tcaactggca aggacaacct ccataccatg   2160
```

```
tatttgaaga acctgttctc agaagagaac cttaaggata tagtactcaa attaaatggc   2220

gaggccgaac tgttctttcg taaagcgtct atcaagactc caattgttca caagaaaggg   2280

tcggttctgg tcaaccgttc gtatactcaa accgtgggta acaaagagat aagagttagc   2340

attcctgaag aatactatac agaaatttat aactacctga atcacattgg caaaggcaaa   2400

ttatctagcg aagcccagcg ttacctggac gaaggaaaga taaagagttt cacggcgacc   2460

aaagacattg ttaagaacta tcgttattgc tgcgatcatt atttcttaca cttaccgatt   2520

actattaact ttaaagctaa gagcgacatc gcggttaacg aacgtacact ggcgtatatc   2580

gcgaagaagg aagatatcca tatcataggc atagaccgag gtgagagaaa cctgctctat   2640

ataagcgtaa tcgatgtgca cggcaacatt cgtgaacagc gcagcttcaa tattgtaaat   2700

ggttacgact accagcagaa acttaaagac cgggagaaga gtcgcgacgc agcacgaaag   2760

aactgggaag aaatcgagaa gatcaaagaa ctcaaggagg gctacttatc tatggttatc   2820

cactatatcg cgcgcttggt tgtcaagtac aatgcagtgg tggcgatgga ggacctgaac   2880

tatgggttta agaccggacg gtttaaagtg gaacgtcagg tttatcagaa atttgaaacg   2940

atgctgattg agaagttgca ttaccttgta tttaaagacc gtgaagtgtg tgaggaaggt   3000

ggagtactgc gcgggtatca actgacttat atcccagaat cactcaagaa ggtaggcaaa   3060

cagtgcgggt tcatcttcta cgttccggca ggctatacta gtaagatcga cccaactact   3120

ggctttgtta atctgttcag ctttaagaac ttgaccaacc gggaatcacg tcaggacttc   3180

gttggtgagt tcgatgaaat ccgttatgat cgtgacaaga acatgtttga attctccttc   3240

gactataata attatataaa gaagggcacc atgctggcta gcacgaaatg gaaggtttac   3300

accaacggta cacgtttaaa gagaatagtt gttaatggca aatataccag tcagtccatg   3360

gaagtagaac taactgatgc catggagaag atgttacaac gtgctggtat cgaataccac   3420

gacggcaaag acctgaaagg gcaaatcgtt gagaagggca tcgaagccga gattattgat   3480

atcttccgtc taaccgtcca gatgaggaac tcgcgttcgg aatctgagga tcgtgaatat   3540

gatagactaa tttctcccgt gcttaatgat aaaggtgagt tctttgatac agccactgcc   3600

gacaagacgt taccgcaaga tgccgacgca aatggtgcgt actgtattgc gctgaaaggt   3660

ctgtatgaag tgaagcagat caaagagaac tggaaagaga acgaacaatt cccgcgaaat   3720

aagcttgtgc aggacaacaa gacgtggttt gacttcatgc aaaagaagcg atatctgtaa   3780
```

<210> SEQ ID NO 21
<211> LENGTH: 3903
<212> TYPE: DNA
<213> ORGANISM: Artificial Sequence
<220> FEATURE:
<223> OTHER INFORMATION: Modified MAD nuclease nucleic acid sequence

<400> SEQUENCE: 21

```
atgagcattt accaggaatt tgtgaacaag tatagtctgt ccaagacact gcggttcgaa     60

ctaatcccac agggtaagac cctggagaat atcaaagccc gcggccttat tctggatgac    120

gagaagcgcg cgaaggacta caagaaagcg aaacagatca tcgataaata ccaccaattc    180

ttcattgagg agatcctgtc atcggtatgt atttcagaag atttattaca gaattatagt    240

gacgtttatt tcaaactcaa aaagagtgac gatgataatc tgcagaaaga ctttaagagt    300

gcgaaagaca ccataaagaa acagatttct gaatacatca aggatagtga gaaatttaag    360

aacctgttca atcagaatct gatcgatgcg aagaaagggc aagaatcaga tttaatcctg    420

tggctcaagc agtcgaaaga taatggtatt gaattattta aagccaattc tgacatcacg    480
```

-continued

```
gatattgatg aagcgctgga aatcataaag agcttcaagg gttggacaac gtacttcaag    540
ggcttccatg agaatcgcaa gaatgtatat agttctaacg acatcccaac ctccatcatt    600
tatcgtatcg tagatgataa ccttcccaag tttctggaga ataaagcgaa atacgagtct    660
ttgaaagata aagcgccaga ggccattaac tacgaacaga ttaagaagga tctggcagaa    720
gaattgacat tcgatattga ttacaagaca tccgaagtga accaaagggt gttcagctta    780
gatgaagtct ttgaaattgc taatttcaat aattatttaa atcaatccgg cattaccaaa    840
tttaacacca taataggtgg caaattcgtg aatggcgaga acactaagcg caaaggtatt    900
aacgagtaca tcaatctgta ttcacagcag attaacgaca agaccctgaa gaagtataag    960
atgtcagtct tgtttaaaca gatcctcagt gatacagaga gcaaatcgtt cgtaatagat   1020
aaactggaag atgactctga cgtcgtaacc actatgcagt cgttctatga gcagatcgcg   1080
gcctttaaga ccgttgaaga gaagagcatt aaggaaacgt tatcactcct gtttgacgac   1140
cttaaagcac agaaactgga cctttcgaag atttacttta agaatgataa atctctgact   1200
gatctgtctc aacaggtatt tgatgattac tcggtgattg gcactgctgt gttagaatat   1260
attacccagc aaattgcacc taagaatttg gataatccct ccaagaagga acaggagctc   1320
atagctaaga agacggagaa agctaagtac ctgtcactgg aaacaattaa gctggcctta   1380
gaagagttta acaaacatcg cgatatcgat aagcagtgtc ggtttgaaga aatcttagct   1440
aacttcgccg ctatacctat gatcttcgat gaaattgccc agaacaagga taatctggct   1500
caaattagca tcaaatatca gaatcaaggg aagaaagact tgttacaggc tagcgcggag   1560
gatgatgtta aagcgattaa ggacttactg gaccagacga ataacttatt acataaactt   1620
aagatctttc acatctcaca gtctgaagat aaggccaaca tcctggataa agatgaacat   1680
ttctatcttg tgtttgaaga atgctatttc gagttagcta atatagtacc tttatacaac   1740
aagattcgta attacatcac acagaaacca tacagcgacg agaagtttaa gttgaacttt   1800
gagaactcca cccttgctaa tggctgggac aagaataaag aaccagataa taccgcaatc   1860
ctctttatca aagatgacaa atactacctg ggtgttatga acaagaagaa taacaagatc   1920
tttgacgata aggccattaa agagaacaaa ggagaaggtt acaagaagat cgtttataaa   1980
ttgttgcccg gcgcgaacaa gatgctccct aaggtcttct ttagtgctaa gagcattaag   2040
ttctataacc cgtcagaaga tattctgcgc atccgaaatc acagcaccca cacgaagaac   2100
ggatctccac agaaaggcta tgagaaattc gagtttaaca tagaggattg tcgcaagttt   2160
attgacttct ataagcagag catttcaaag catcctgaat ggaaagattt cggattccgc   2220
ttcagtgata cccagcgcta taatagcatt gatgaattct accgagaagt cgagaaccaa   2280
ggctacaaac tgacgtttga gaacatctct gaatcctata ttgattcggt ggttaatcag   2340
ggcaagctgt acttatttca aatttataat aaggatttct ccgcctacag taaaggtcga   2400
cctaacctgc acaccctgta ttggaaagcg ttatttgatg agcgtaatct ccaagacgtt   2460
gtgtacaaac tcaacggtga agccgaatta ttctatcgca aacagtcgat tcccaagaaa   2520
atcacccatc cggcgaagga ggctattgcg aacaagaaca aagataatcc taagaaggaa   2580
tctgtgttcg aatacgatct aattaaagac aagagattca cggaggacaa gttcttcttc   2640
cactgcccga tcaccattaa cttcaaatcc agcggcgcca ataagtttaa cgacgaaatc   2700
aacctgttgc tcaaagagaa ggctaacgac gtgcacatac tgagtataga tcgaggcgaa   2760
cggcacttag cgtattatac cttagtggat ggcaagggta atattatcaa gcaagacaca   2820
```

```
tttaatatta tcggtaatga ccgcatgaag acaaattacc acgacaagct ggccgccatc   2880
gagaaggatc gtgatagtgc tcgtaaagat tggaagaaga ttaacaatat caaagagatg   2940
aaagaaggtt atttgagcca ggtagttcat gaaatcgcca aattagttat tgaatataat   3000
gcaatcgttg tatttgaaga cctgaacttc ggctttaaac gcggtcgatt caaagttgag   3060
aagcaggtgt atcagaagct ggaaaagatg ctgattgaga aattgaacta ccttgtgttt   3120
aaagacaatg agttcgacaa gacgggcggc gtgctgaggg cctatcagct aaccgcgccg   3180
tttgagacat ttaagaaaat gggtaaacaa acaggcatca tttactacgt tccagcgggc   3240
ttcaccagca agatatgtcc tgtcacaggc ttcgtgaatc agctgtaccc aaagtacgaa   3300
agtgttagta aatctcagga atttttctct aaatttgata agatttgcta caatttggat   3360
aaaggctatt tcgaatttag ctttgattac aagaacttcg gtgacaaggc tgcgaaaggc   3420
aaatggacaa ttgcatcgtt cgggagccgt ctgattaact ttcgtaatag tgacaagaat   3480
cataactggg ataccaggga agtgtatcca accaaagaac tggagaaact tctcaaagac   3540
tattccatcg aatacggcca tggtgaatgt attaaagcgg cgatctgcgg agagagtgac   3600
aagaaattct tcgccaaact gacctcagtg ttaaacacca ttctgcagat gcgaaacagt   3660
aagactggta cagagctgga ctatttaatt tcaccggttg cagatgtaaa tggcaacttc   3720
tttgatagcc gtcaggcacc gaagaatatg ccacaggatg cagatgcaaa cggtgcatac   3780
catattggtt tgaaaggtct gatgctcctg ggtcgcataa agaacaacca agagggcaag   3840
aagctgaacc tggttataaa gaacgaagaa tacttcgaat tcgttcagaa tcgtaacaac   3900
taa                                                                 3903
```

```
<210> SEQ ID NO 22
<211> LENGTH: 3624
<212> TYPE: DNA
<213> ORGANISM: Artificial Sequence
<220> FEATURE:
<223> OTHER INFORMATION: Modified MAD nuclease nucleic acid sequence

<400> SEQUENCE: 22

atgtattatc agaatttaac caagatgtat ccgattagta agacccttcg taacgaacta     60
attccggtag gaaagactct ggagaacata cggaagaatg gtatcttgga agcagatatc    120
caacgtaaag ccgactatga acatgtcaag aaattgatgg acaattacca caaacaacta    180
atcaacgaag cgctgcaggg agtgcatctg tcggatctga gcgacgctta tgacctgtac    240
tttaatcttt ctaaagagaa gaactcagta gatgccttct ccaaatgcca ggataaactt    300
cggaaagaga tcgtgtcttt cctgaagaat cacgagaatt ttccgaagat cggaaataaa    360
gaaattatca aactgatcca gagcctgaat gacaacgacg cagacaataa cgcgctcgat    420
tccttctcga atttctatac ctacttcagc agctataacg aggttagaaa gaatctctac    480
agcgatgagg agaagagtag cacagtagca tataggttaa taaacgagaa cttgccgaaa    540
tcgttagata atattaaagc gtacgccatc gctaagaaag ccggtgtccg tgcggaaggc    600
ctctcggaag aggaacagga ttgtttattc attattgaaa cctttgaacg taccctgaca    660
caggacggca tcgataatta caatgctgat atcggcaagc ttaacaccgc aatcaatctg    720
tacaatcaac agaacaagaa gcaggaaggt ttccgcaaag taccgcagat gaaatgcctg    780
tacaaacaga ttctgagcga ccgggaagag gcattcatcg atgaatttag tgatgacgag    840
gacctgataa ccaacattga aagcttcgct gagaatatga atgtattcct aaactccgaa    900
ataatcaccg actttaagaa tgcgctcgta gaatctgacg gctccctggt ctatataaag    960
```

-continued

```
aatgatgtgt ccaagacctt attctcaaat attgtattcg gaagctggaa cgcaattgat   1020
gagaagttat cggatgaata cgatctggcg aattcaaaga agaaaaaaga cgagaagtat   1080
tatgagaagc gtcagaagga actaaagaag aataagagct atgatctgga aactattatt   1140
gggctgtttg atgactctat cgacgtcatc ggtaaataca tagagaagct cgagtcagac   1200
attaccgcca ttgctgaagc caagaacgac ttcgatgaga tcgtccttcg taagcatgat   1260
aagaacaaat cacttcgtaa gaacacaaac gcggttgaag ccataaagag ttacctggac   1320
accgttaaag atttcgaacg ggatattaaa ctgattaacg ggtctggcca ggaggtggag   1380
aagaatctgg ttgtatatgc agagcaggag aacatactcg cagagatcaa gaacgtggac   1440
agtctctata acatgtcacg taactatctg acacagaaac cattctcgac ggagaaattt   1500
aaactgaact ttgagaatcc cacgttacta aatggttggg accgtaacaa agagaaagac   1560
tatctaggaa tactgttcga gaaagagggt atgtattatc ttggcatcat caataacaat   1620
caccgtaaga tcttcgagaa cgagaaactg tgcaccggta aagaaagttg cttcaataag   1680
atcgtgtata aacagatctc gaatgcggcc aaatacctgt ctagcaaaca gattaacccg   1740
cagaacccgc ctaaggaaat tgcagagatc ctgctgaaac gcaaagcaga tagcagttcc   1800
ttaagtcgta aagaaacgga actgttcatc gattatttga aagacgattt cttagtaaat   1860
tatccaatga tcatcaacag tgacggcgag aatttcttta actttcactt taaacaggct   1920
aaggactacg gctcgttaca ggagttcttc aaggaagtgg aacatcaagc gtattccttg   1980
aagacacgtc cgattgacga ttcttacatt tatcggatga ttgacgaagg taagctgtac   2040
ctgtttcaga ttcataataa agacttcagc ccgtactcga aggaaatct caacctgcat   2100
actatatatc tccagatgtt attcgatcag cgtaatctga ataacgttgt atataaactg   2160
aacggcgaag cagaagtgtt ttatcgccca gcgtccatta acgatgagga agttattatc   2220
cacaaagcag gtgaagaaat taagaacaag aatagcaaac gggccgttga caaacctacg   2280
agcaaattcg gctatgatat tattaaagac cgccggtatt cgaaagataa gtttatgctt   2340
catatccctg tgaccatgaa cttcggcgtt gacgagaccc gccgcttcaa tgatgtcgta   2400
aatgatgcct tacgcaatga tgagaaggtt cgcgtgattg gcattgatag aggtgaacgc   2460
aacctgttat acgtcgtagt ggtcgatacg gatggaacta tccttgaaca gattagtctc   2520
aacagtatta ttaataacga gtatagcatt gaaactgatt atcacaagct gctggacgag   2580
aaagagggtg atcgcgaccg cgccagaaag aactggacca caattgagaa tattaaggaa   2640
ctgaaagagg gctatctgtc acaagttgta aatgttatcg cgaagttggt gttaaagtac   2700
aatgcgatta tttgcctgga agatttaaat ttcggtttca aacgtgggcg ccagaaggtc   2760
gagaagcagg tgtatcagaa gtttgaaaag atgctgatcg ataaactgaa ttatttagta   2820
attgataaat cgcgtaaaca ggagaagccg gaagaattcg gtggtgcttt gaacgcattg   2880
cagttaacaa gcaaatttac ttctttcaaa gatatgggta aacagacagg aattatttat   2940
tatgtccctg cgtatcttac ctctaagatt gacccaacca cgggctttgc gaacctgttc   3000
tatgtgaaat atgagaatgt cgagaaagcc aaggaattct tttctagatt cgactctatc   3060
agctataaca acgagagcgg atactttgaa tttgcctttg attataagaa attcactgat   3120
cgcgcctgtg gcgctcggag ccagtggaca gtttgcacct atggcgagcg aattattaag   3180
taccgtaacg cggacaagaa taacagcttt gatgacaaga ccatcgtact gtcggaagaa   3240
ttcaaagagt tgtttagcat ctatggtatc agctacgaag atggcgcgga attaaagaac   3300
```

aagatcatga gcgtagatga ggcggatttc tttcgttgtc tgaccggctt attacagaag 3360
acattacaaa tgcgtaacag cagtaatgat ggcacacggg attacattat aagcccaatt 3420
atgaacgata gaggcgagtt cttcaattct gaggcgtgtg atgcttcgaa accgaaagat 3480
gccgatgcca acggcgcctt caacattgcg cgcaaaggcc tgtgggtgtt agagcagatt 3540
cgcaatactc ccagcggcga taaattgaat ctggcgatga gcaacgctga atggctggag 3600
tacgcacaga ggaatcagat ctaa 3624

<210> SEQ ID NO 23
<211> LENGTH: 3621
<212> TYPE: DNA
<213> ORGANISM: Artificial Sequence
<220> FEATURE:
<223> OTHER INFORMATION: Modified MAD nuclease nucleic acid sequence

<400> SEQUENCE: 23
atgtattacc agaatttaac gaagaaatac ccggtgagca agactatacg gaatgaactg 60
attcctattg gtaagactct ggagaacatt cgtaagaata atatcctcga atccgatgtc 120
aagcgcaagc aagattatga acatgtgaaa gggattatgg acgaatatca taaacaactg 180
attaacgaag cgctggataa ctacatgctg ccgagtctga atcaagccgc agagatctat 240
ctaaagaaac atgttgacgt cgaggacaga gaggaattta agaagaccca ggatctgttg 300
cgcagagagg ttacgggtcg cttgaaggaa cacgagaatt atacgaagat cggaaagaaa 360
gatatccttg atcttctgga gaagctgccg tctatttcgg aagaagatta taatgccctg 420
gagagcttcc gcaatttcta cacatacttc acctcttata acaaggtgcg tgagaacctg 480
tattcggatg aagagaagtc aagcacagtg gcctacagat taatcaacga gaaccttccg 540
aaatttcttg ataatattaa gagttacgcg tttgtcaaag ccgcaggcgt cctggcagat 600
tgcattgaag aagaagagca agatgcactg tttatggttg agaccttcaa tatgactctg 660
actcaagaag gcatcgatat gtataattat caaatcggga aggtgaactc cgcgattaat 720
ctgtataatc agaagaatca caaagttgaa gaatttaaga agatcccgaa gatgaaagtt 780
ctatacaaac agatcctgag tgatagggag gaggtattca taggagagtt caaagacgat 840
gaaacgttgc tcagctcaat cggcgcgtat ggcaatgtct taatgacata tcttaaatcc 900
gagaagatta acatcttctt cgatgcactc cgggaatctg aagggaagaa cgtgtacgta 960
aagaacgacc tttcaaagac caccatgtcg aatatcgtct tcggaagctg gagcgcattc 1020
gatgaattgt tgaaccagga gtatgatctt gccaacgaga acaagaagaa ggacgacaaa 1080
tactttgaga agcgccagaa ggagctaaag aagaataaga gttatacgct ggagcaaatg 1140
tctaatctga gtaaggaaga cattagccct attgagaatt acatcgaacg gatttcagaa 1200
gacatcgaga agatatgcat atataatggc gaattcgaga agattgtggt gaacgaacat 1260
gacagctctc gtaaactgag taagaacatc aaagcggtta aagtcatcaa ggattacttg 1320
gattcgatca aagaactgga acacgacatt aaattgatca acggtagtgg ccaggaattg 1380
gagaagaact tggttgtcta tgtgggtcaa gaagaagccc tggagcagct ccgtccagtg 1440
gatagtttat acaaccttac tcgaaactat ttaacaaaga agcccttctc aactgagaaa 1500
gtgaaactta acttcaacaa gagtacgctg ttaaatggtt gggacaagaa caaagaaacg 1560
gataatctcg gtatcttgtt cttcaaagac gggaagtatt atcttggcat catgaataca 1620
actgctaaca aagcctttgt gaatccgccc gccgccaaga ccgagaatgt ctttaagaaa 1680
gttgattata agttactgcc gggcagtaat aagatgctgc caaaggtctt tttcgctaag 1740

```
agcaacattg gatactataa cccatctacg gaactgtact ctaattataa gaaaggcacc   1800
cacaagaaag gcccgtcatt ctctatcgat gattgtcata acttaattga tttcttcaaa   1860
gaaagcatta agaaacatga ggactggtcg aaatttggtt tcgaattctc tgacaccgca   1920
gactaccgcg atatttcaga gttctaccgc gaagtagaga aacagggcta taaacttacg   1980
tttacggaca tagacgaaag ctatattaac gatctgattg aaaagaatga actgtattta   2040
ttccaaattt ataacaaaga tttcagtgaa tatagcaaag gtaaactcaa cctgcatacc   2100
ctgtacttca tgatgttgtt cgatcagcgc aacttggaca atgtggtcta caaactgaac   2160
ggtgaggcag aagttttcta ccgcccggca tcgatcgccg agaatgaact ggttattcat   2220
aaagcaggtg agggtataaa gaacaagaat ccgaaccgtg caaaggtcaa agaaactagc   2280
acgttctctt acgatattgt gaaagataaa cgatatagca aatacaaatt taccctgcat   2340
attcctatta ccatgaactt cggagtcgac gaagtgcggc gtttcaatga cgtgatcaac   2400
aacgccctgc gtacggacga taatgtcaat gttattggca tcgatcgtgg tgaacgcaat   2460
ctgctttacg tcgttgtaat aaacagtgaa ggaaagattc tcgaacagat ttctttaaat   2520
tctatcatca acaaagaata tgatatcgaa accaactacc atgctctgtt ggatgaacgt   2580
gaggacgatc ggaacaaagc gcgtaaagat tggaatacga tcgagaatat taaagaattg   2640
aagaccggct atctttcaca ggttgtcaat gttgttgcta aattagtgct gaaatataac   2700
gcgatcattt gcctggaaga tttaaacttt gggttcaaac gaggccgtca gaaagtggag   2760
aagcaagttt accagaagtt cgagaagatg cttattgaga aactaaacta cctcgtgatt   2820
gacaagagcc gcgaacaggt gtcaccggag aaaatgggtg gcgcgttgaa tgcattgcag   2880
ttaacttcta aatttaagtc gttcgctgaa ctaggcaagc aaagcggtat tatctattac   2940
gtaccggcct acttaactag taagattgat cccacgaccg gctttgtaaa cctcttctat   3000
attaaatacg agaacatcga gaaagccaag cagttcttcg atggatttga cttcattcgt   3060
ttcaacaaga aagacgacat gtttgagttc tcgtttgatt ataagtcatt cacccagaaa   3120
gcttgtggaa tccgtagcaa atggattgtg tacacgaatg gagaacgtat tattaaatat   3180
ccgaacccgg agaagaataa tttgtttgat gagaaagtga ttaacgtgac cgacgagatt   3240
aagggtttgt tcaaacaata ccgcatcccg tacgagaacg gtgaagacat taaggaaatt   3300
ataatcagca aagcagaggc tgacttctat aaacgcctat tccgcctgtt gcatcagact   3360
ttgcagatgc gcaactccac cagcgatggc actcgtgact acataatttc tccggtgaag   3420
aacgatagag gtgagttttt ctgttccgaa ttctcagaag ggaccatgcc gaaagatgcg   3480
gatgccaatg gagcgtacaa tatcgcgcgc aagggtctgt gggtactgga acagataaga   3540
cagaaggatg aaggagagaa ggtaaactta tcgatgacaa atgcagaatg gctgaagtat   3600
gcccaactgc acctgctgta a                                             3621
```

<210> SEQ ID NO 24
<211> LENGTH: 3756
<212> TYPE: DNA
<213> ORGANISM: Artificial Sequence
<220> FEATURE:
<223> OTHER INFORMATION: Modified MAD nuclease nucleic acid sequence

<400> SEQUENCE: 24

```
atgaatcaca tgaaacagtt cactaatcaa ttctcgttat cgaagacact tagattcgaa     60
ctcatcccac agggaaagac gaaagaattt attgaaataa atggcctgat cgagaaggat    120
```

```
aacgaacgtg ccgtgagcta caagaaagtc aagaagatca tcgatgaata tcacaagtac    180
tttattgaaa tggttctgtg cgactttaaa ctgcacggtc tggagaccta tgaaacgatc    240
ttcaataaga aggagaaaga tgacaccgac aagaaggagt ttgacaacat tcgtaattct    300
ctgcgcaagc aaatcgcgga cgccttcgca aagaatccga acgatgaaat caaagaacgt    360
tttaagaatc tgttcgctaa ggaactgatt aaacaggacc ttcttaactt cgtggatgac    420
gagcagaagg agctggtgaa cgaatttaag gacttcacta cttactttac cggcttccat    480
cagaatcgtc gtaacatgta cgttgcagat gagaaggcaa ccgcgatcgc ataccgtctc    540
gttaacgaga acctgcccaa gttcatcgat aatcttaaga tctatgagaa gatcaagaag    600
gacgctccgg aactgatctc cgatcttaac aagacactgg ttgagatgga agaaatcgtg    660
cagggcaaga cactggatga aatatttagc ttaagcttct tcaaccagac cttaacgcaa    720
actggcattg aactgtataa tattgttatt ggtgggcgca ccgcggacga agggaagaca    780
aagattaaag gactgaatga atatatcaac acagactaca accagaaaca aacggacaag    840
aagaagaaac aagccaagtt taaacagctc tataaacaaa ttctgagtga ccgtcattct    900
gtgagcttcg ttgcggagac ctttgagacc gatgcacaat tactggagaa tattgaacag    960
ttctactcat ccgtgctgtg taactatgaa gatgatggtc acaccacaaa tatattcgaa   1020
gcgataaaga atctgataat aggtctcaag acgttcgacc tatcaaagat ctatctccga   1080
aacgatacgt ccttaaccga tattagtcag aaactgtttg gcgactggag catcatcagc   1140
agcgcactca acgactatta tgagaagcag aacccgatct cgtctaagga gaagcaggag   1200
aagtatgatg agaggaaagc gaaatggttg aaacaggact ttaatatcga aactattcaa   1260
acggcgctca atgaatgcga ctcagaaatc attaaagaga aaaacaacaa gaatattgtt   1320
agcgagtatt tcgcgaaatt aggcttagat aaagacaaca agattgacct cttgcaaaag   1380
atccaccata attacgttgt aattaaggac ttgctgaatg agccgtatcc agagaatatc   1440
aaactgggaa atcagaagga acaagtgtct cagattaagg actttctgga tagcatccta   1500
aaccttatac acttcttgaa accgctcagt ctgaaagata aagataaaga gaaggatgag   1560
ttattttatt ctttgttcac cgcgctgttc gagcacctgt cgcagaccat atcgatctat   1620
aacaaggttc gcaactactt gacgcagaag gcttacagta ccgaaaagat caagttgaac   1680
tttgagaata gtacattgct gaacggatgg gacgtgaaca aagagccggt gaatactagc   1740
gtcatattcc gtaagaatgg tttgttctac ctgggaatca tgtctaaatc caataaccgc   1800
atctttgaac gtaatgtacc ggtgtgtaag aatgaagaaa ccgcctttga gaaaatgaat   1860
tataaattac tgccgggcgc taacaagatg ctcccgaagg tattcctgag cgctaagggg   1920
atagaaagct ttcagccgtc agcagaaatc cagagcaaat atcagaagga gacccataag   1980
aaaggtgatg cgttcgtgcg caaagatatg gagaacctta tcgacttctt taaacaaagt   2040
attgccaaac ataccgattg gaagcacttc aaccaccagt tctcgaagac ggaaacttac   2100
aacgatttaa gtgaattcta taaggaggtt gagaagcaag gatataaatt aacctttacc   2160
aagttggacg agacttatat taaccaactg gtggatgagg gtaaactgta tctgttccaa   2220
atctataaca aggacttcag tcccttcagt aagggcaagc cgaacatgca taccctgtat   2280
tggaagatgt tatttgacga acagaatctg cagaatgttg tatataaact gaatggtgaa   2340
gccgaagtct tcttccggca gagttccatc aaacagaccg accgtatcat tcacaaagca   2400
aaccaagcca ttgacaacaa gaatccactg aacaataaga agcagtcgtc tttcaattac   2460
gacttaatta aggacaaacg gtttaccctg gataaatttc agttccacgt tccgattacg   2520
```

```
ctgaacttca aagccgaagg gaatgaatac ctgaacacta aagtgaacga ataccttaag   2580

agcaacagtg atgtgaagat cattggcttg gacagaggtg agcgacattt gatctatctg   2640

actttaatca atcagaaggg tgaactactc aaacagcaaa gtcttaacgt cattgctact   2700

agccaagaac atgagactga ctataagaac ttactggtta acaaggagaa cgaaagagca   2760

aatgccaggc aagattggaa gaccatcgag actattaaag aattgaaaga aggttactta   2820

tcgcaggtcg tacatcaaat agcaaccatg atggtggacg agaacgcgat cgtggttatg   2880

gaagatctga atgccggatt catgcgtggc agacagaagg ttgaacggca ggtgtatcag   2940

aagctggaga aaatgcttat tgagaagtta aactacctgg tgttcaagaa taatgatgtg   3000

aatgaaaccg ccggtgtatt aaatgcgtta cagctcacga ataaatttga aagtttcgag   3060

aagatgggca agcagagtgg ctttctgttc tatgtgcccg cgtggaacac gagtaagatc   3120

gacccggcca caggatttgt cgactttctt aaacccaaat acgaaagcgt cgagaaagct   3180

aagctcttct ttgagaagtt tgaatccatt aaatttaacg cggacaagaa ttacttcgaa   3240

tttgaatttg attacaagaa gttcaccgag aaggcggaag gcagtcaaac caaatggacg   3300

gtctgcacgc atagtgacgt ccgctaccgc tataatccgc agaccaaagc tagcgatgaa   3360

gtcaatgtaa ctaacgaact taaactgata tttgacaaat ttaagattga atacaagaat   3420

gggaagaact taaagaccga attgcttctc caagatgata agcagctgtt ctccaaactc   3480

ctccattatc tggcgctgac ccttatgctc agacaaagta agagtggcac ggatatcgat   3540

ttcattctta gcccggtcgc caagaacggt gtgttctatg actcgaggaa tgccatgcca   3600

aacttaccta aggatgccga tgcgaacgga gccttccaca ttgctctgaa aggcctgtgg   3660

tgtgtgcagc aaataaagaa ggcggatgac ctgaagaaaa ttaagctggc aatttcgaat   3720

aaagaatggc tctcatttgt ccagaatctg aaataa                             3756
```

```
<210> SEQ ID NO 25
<211> LENGTH: 30
<212> TYPE: DNA
<213> ORGANISM: Artificial Sequence
<220> FEATURE:
<223> OTHER INFORMATION: Primer sequence

<400> SEQUENCE: 25

atggcaccca agaagaagag gaaggtgtta                                      30


<210> SEQ ID NO 26
<211> LENGTH: 10
<212> TYPE: PRT
<213> ORGANISM: Artificial Sequence
<220> FEATURE:
<223> OTHER INFORMATION: Artificial peptide

<400> SEQUENCE: 26

Met Ala Pro Lys Lys Lys Arg Lys Val Leu
1               5                   10


<210> SEQ ID NO 27
<211> LENGTH: 20
<212> TYPE: DNA
<213> ORGANISM: Artificial Sequence
<220> FEATURE:
<223> OTHER INFORMATION: Primer sequence

<400> SEQUENCE: 27

ttgggtaacg ccagggtttt                                                 20
```

<210> SEQ ID NO 28
<211> LENGTH: 20
<212> TYPE: DNA
<213> ORGANISM: Artificial Sequence
<220> FEATURE:
<223> OTHER INFORMATION: Primer sequence

<400> SEQUENCE: 28
tgtgtggaat tgtgagcgga 20

<210> SEQ ID NO 29
<211> LENGTH: 199
<212> TYPE: DNA
<213> ORGANISM: Artificial Sequence
<220> FEATURE:
<223> OTHER INFORMATION: Yeast editing cassette

<400> SEQUENCE: 29
ggccccaaat tctaatttct actgttgtag atacgacgtt gaagcttcac aatttttacg 60
ccgacataga ggagaagcat atgtacaatg agccggtcac aaccctcgag acacgacgtt 120
gaagcttaac aaacacacca cagacgtggg tcaataccat tgaaagatga gaaaagtaac 180
aatatacgcg ctcctgccc 199

<210> SEQ ID NO 30
<211> LENGTH: 199
<212> TYPE: DNA
<213> ORGANISM: Artificial Sequence
<220> FEATURE:
<223> OTHER INFORMATION: Yeast editing cassette sequence

<400> SEQUENCE: 30
ggccccaaat tctaatttct actcttgtag atacgacgtt gaagcttcac aatttttacg 60
ccgacataga ggagaagcat atgtacaatg agccggtcac aaccctcgag acacgacgtt 120
gaagcttaac aaacacacca cagacgtggg tcaataccat tgaaagatga gaaaagtaac 180
aatatacgcg ctcctgccc 199

<210> SEQ ID NO 31
<211> LENGTH: 199
<212> TYPE: DNA
<213> ORGANISM: Artificial Sequence
<220> FEATURE:
<223> OTHER INFORMATION: Yeast editing cassette sequence

<400> SEQUENCE: 31
ggccccaaat tctaatttct actattgtag atacgacgtt gaagcttcac aatttttacg 60
ccgacataga ggagaagcat atgtacaatg agccggtcac aaccctcgag acacgacgtt 120
gaagcttaac aaacacacca cagacgtggg tcaataccat tgaaagatga gaaaagtaac 180
aatatacgcg ctcctgccc 199

<210> SEQ ID NO 32
<211> LENGTH: 200
<212> TYPE: DNA
<213> ORGANISM: Artificial Sequence
<220> FEATURE:
<223> OTHER INFORMATION: Yeast editing cassette sequence

<400> SEQUENCE: 32
ggccccaaat tctaatttct actgtgtgta gatacgacgt tgaagcttca caatttttac 60
gccgacatag aggagaagca tatgtacaat gagccggtca caaccctcga gacacgacgt 120
tgaagcttaa caaacacacc acagacgtgg gtcaatacca ttgaaagatg agaaaagtaa 180
caatatacgc gctcctgccc 200

<210> SEQ ID NO 33
<211> LENGTH: 195
<212> TYPE: DNA
<213> ORGANISM: Artificial Sequence
<220> FEATURE:
<223> OTHER INFORMATION: Yeast editing cassette sequence

<400> SEQUENCE: 33
ggccccaaat tctaatttct actgttgtag atcttttctc atctttcaat ggtttttgta 60
tcctcgccat ttactctcgt cgggaaagag cgcaatggat acaattcccc acttttctca 120
tcttacaatg gtattgaccc acgtctgtgg tgtgtttgtg aagcttcaac gtcgtcaata 180
tacgcgctcc tgccc 195

<210> SEQ ID NO 34
<211> LENGTH: 195
<212> TYPE: DNA
<213> ORGANISM: Artificial Sequence
<220> FEATURE:
<223> OTHER INFORMATION: Yeast editing cassette sequence

<400> SEQUENCE: 34
ggccccaaat tctaatttct actcttgtag atcttttctc atctttcaat ggtttttgta 60
tcctcgccat ttactctcgt cgggaaagag cgcaatggat acaattcccc acttttctca 120
tcttacaatg gtattgaccc acgtctgtgg tgtgtttgtg aagcttcaac gtcgtcaata 180
tacgcgctcc tgccc 195

<210> SEQ ID NO 35
<211> LENGTH: 195
<212> TYPE: DNA
<213> ORGANISM: Artificial Sequence
<220> FEATURE:
<223> OTHER INFORMATION: Yeast editing cassette sequence

<400> SEQUENCE: 35
ggccccaaat tctaatttct actattgtag atcttttctc atctttcaat ggtttttgta 60
tcctcgccat ttactctcgt cgggaaagag cgcaatggat acaattcccc acttttctca 120
tcttacaatg gtattgaccc acgtctgtgg tgtgtttgtg aagcttcaac gtcgtcaata 180
tacgcgctcc tgccc 195

<210> SEQ ID NO 36
<211> LENGTH: 196
<212> TYPE: DNA
<213> ORGANISM: Artificial Sequence
<220> FEATURE:
<223> OTHER INFORMATION: Yeast editing cassette sequence

<400> SEQUENCE: 36
ggccccaaat tctaatttct actgtgtgta gatcttttct catctttcaa tggtttttgt 60
atcctcgcca tttactctcg tcgggaaaga gcgcaatgga tacaattccc cacttttctc 120
atcttacaat ggtattgacc cacgtctgtg gtgtgtttgt gaagcttcaa cgtcgtcaat 180
atacgcgctc ctgccc 196

```
<210> SEQ ID NO 37
<211> LENGTH: 201
<212> TYPE: DNA
<213> ORGANISM: Artificial Sequence
<220> FEATURE:
<223> OTHER INFORMATION: Yeast editing cassette sequence

<400> SEQUENCE: 37

ggccccaaat tctaatttct actgttgtag atccgacgag agtaaatggc gatttttttca     60

ataccattga aagatgagaa aagtaaagaa ttgtatccat tgcgctcgtt cccgacgaga    120

gtataaggcg aggatacgtt ctctatggag gatggcatag gtgatgaaga tgaaggagaa    180

gcaatatacg cgctcctgcc c                                               201


<210> SEQ ID NO 38
<211> LENGTH: 201
<212> TYPE: DNA
<213> ORGANISM: Artificial Sequence
<220> FEATURE:
<223> OTHER INFORMATION: Yeast editing cassette sequence

<400> SEQUENCE: 38

ggccccaaat tctaatttct actcttgtag atccgacgag agtaaatggc gatttttttca     60

ataccattga aagatgagaa aagtaaagaa ttgtatccat tgcgctcgtt cccgacgaga    120

gtataaggcg aggatacgtt ctctatggag gatggcatag gtgatgaaga tgaaggagaa    180

gcaatatacg cgctcctgcc c                                               201


<210> SEQ ID NO 39
<211> LENGTH: 201
<212> TYPE: DNA
<213> ORGANISM: Artificial Sequence
<220> FEATURE:
<223> OTHER INFORMATION: Yeast editing cassette sequence

<400> SEQUENCE: 39

ggccccaaat tctaatttct actattgtag atccgacgag agtaaatggc gatttttttca     60

ataccattga aagatgagaa aagtaaagaa ttgtatccat tgcgctcgtt cccgacgaga    120

gtataaggcg aggatacgtt ctctatggag gatggcatag gtgatgaaga tgaaggagaa    180

gcaatatacg cgctcctgcc c                                               201


<210> SEQ ID NO 40
<211> LENGTH: 202
<212> TYPE: DNA
<213> ORGANISM: Artificial Sequence
<220> FEATURE:
<223> OTHER INFORMATION: Yeast editing cassette sequence

<400> SEQUENCE: 40

ggccccaaat tctaatttct actgtgtgta gatccgacga gagtaaatgg cgatttttttc     60

aataccattg aaagatgaga aaagtaaaga attgtatcca ttgcgctcgt tcccgacgag    120

agtataaggc gaggatacgt tctctatgga ggatggcata ggtgatgaag atgaaggaga    180

agcaatatac gcgctcctgc cc                                              202


<210> SEQ ID NO 41
<211> LENGTH: 201
<212> TYPE: DNA
<213> ORGANISM: Artificial Sequence
<220> FEATURE:
<223> OTHER INFORMATION: Yeast editing cassette sequence
```

<400> SEQUENCE: 41

```
ggccccaaat tctaatttct actgttgtag attccacacc tctgaccaac gctttttatt     60

ggtatgattg cccttggtgg tactattggt acaggtcttt tcattggatt atccacacct    120

ctgtaaaacg ccggcccagt gggcgctctt atatcatatt tatttatggg ttctttggca    180

tcaatatacg cgctcctgcc c                                              201
```

<210> SEQ ID NO 42
<211> LENGTH: 201
<212> TYPE: DNA
<213> ORGANISM: Artificial Sequence
<220> FEATURE:
<223> OTHER INFORMATION: Yeast editing cassette sequence

<400> SEQUENCE: 42

```
ggccccaaat tctaatttct actcttgtag attccacacc tctgaccaac gctttttatt     60

ggtatgattg cccttggtgg tactattggt acaggtcttt tcattggatt atccacacct    120

ctgtaaaacg ccggcccagt gggcgctctt atatcatatt tatttatggg ttctttggca    180

tcaatatacg cgctcctgcc c                                              201
```

<210> SEQ ID NO 43
<211> LENGTH: 201
<212> TYPE: DNA
<213> ORGANISM: Artificial Sequence
<220> FEATURE:
<223> OTHER INFORMATION: Yeast editing cassette sequence

<400> SEQUENCE: 43

```
ggccccaaat tctaatttct actattgtag attccacacc tctgaccaac gctttttatt     60

ggtatgattg cccttggtgg tactattggt acaggtcttt tcattggatt atccacacct    120

ctgtaaaacg ccggcccagt gggcgctctt atatcatatt tatttatggg ttctttggca    180

tcaatatacg cgctcctgcc c                                              201
```

<210> SEQ ID NO 44
<211> LENGTH: 202
<212> TYPE: DNA
<213> ORGANISM: Artificial Sequence
<220> FEATURE:
<223> OTHER INFORMATION: Yeast editing cassette sequence

<400> SEQUENCE: 44

```
ggccccaaat tctaatttct actgtgtgta gattccacac ctctgaccaa cgctttttat     60

tggtatgatt gcccttggtg gtactattgg tacaggtctt ttcattggat tatccacacc    120

tctgtaaaac gccggcccag tgggcgctct tatatcatat ttatttatgg gttctttggc    180

atcaatatac gcgctcctgc cc                                             202
```

<210> SEQ ID NO 45
<211> LENGTH: 201
<212> TYPE: DNA
<213> ORGANISM: Artificial Sequence
<220> FEATURE:
<223> OTHER INFORMATION: Yeast editing cassette sequence

<400> SEQUENCE: 45

```
ggccccaaat tctaatttct actgttgtag atacagtttt ctcacaaaga tttttttttct     60

gtcacgcagt ccttgggtga aatggctaca ttcatccctg ttacatcctc gttcacagtt    120

ttctcataaa gattcctttc tccagcattt ggtgcggcca atggttacat gtattggttt    180
```

tcaatatacg cgctcctgcc c 201

<210> SEQ ID NO 46
<211> LENGTH: 201
<212> TYPE: DNA
<213> ORGANISM: Artificial Sequence
<220> FEATURE:
<223> OTHER INFORMATION: Yeast editing cassette sequence

<400> SEQUENCE: 46
ggccccaaat tctaatttct actcttgtag atacagtttt ctcacaaaga tttttttct 60 gtcacgcagt ccttgggtga aatggctaca ttcatccctg ttacatcctc gttcacagtt 120
ttctcataaa gattcctttc tccagcattt ggtgcggcca atggttacat gtattggttt 180
tcaatatacg cgctcctgcc c 201

<210> SEQ ID NO 47
<211> LENGTH: 201
<212> TYPE: DNA
<213> ORGANISM: Artificial Sequence
<220> FEATURE:
<223> OTHER INFORMATION: Yeast editing cassette sequence

<400> SEQUENCE: 47
ggccccaaat tctaatttct actattgtag atacagtttt ctcacaaaga tttttttct 60 gtcacgcagt ccttgggtga aatggctaca ttcatccctg ttacatcctc gttcacagtt 120
ttctcataaa gattcctttc tccagcattt ggtgcggcca atggttacat gtattggttt 180
tcaatatacg cgctcctgcc c 201

<210> SEQ ID NO 48
<211> LENGTH: 202
<212> TYPE: DNA
<213> ORGANISM: Artificial Sequence
<220> FEATURE:
<223> OTHER INFORMATION: Yeast editing cassette sequence

<400> SEQUENCE: 48
ggccccaaat tctaatttct actgtgtgta gatacagttt tctcacaaag atttttttc 60 tgtcacgcag tccttgggtg aaatggctac attcatccct gttacatcct cgttcacagt 120
tttctcataa agattccttt ctccagcatt tggtgcggcc aatggttaca tgtattggtt 180
ttcaatatac gcgctcctgc cc 202

<210> SEQ ID NO 49
<211> LENGTH: 197
<212> TYPE: DNA
<213> ORGANISM: Artificial Sequence
<220> FEATURE:
<223> OTHER INFORMATION: Yeast editing cassette sequence

<400> SEQUENCE: 49
ggccccaaat tctaatttct actgttgtag atggtaatta tcacaataat gatttttcat 60
tcaattttgg acgtacaaag ttccactggc ggcatggatt agtatttgga aggtaattat 120
cacataaatg aacttgttcc ctgtcaaata ttacggtgaa ttcgagttct gggtcgccaa 180
tatacgcgct cctgccc 197

<210> SEQ ID NO 50
<211> LENGTH: 197
<212> TYPE: DNA

-continued

```
<213> ORGANISM: Artificial Sequence
<220> FEATURE:
<223> OTHER INFORMATION: Yeast editing cassette sequence

<400> SEQUENCE: 50

ggccccaaat tctaatttct actcttgtag atggtaatta tcacaataat gatttttcat     60

tcaattttgg acgtacaaag ttccactggc ggcatggatt agtatttgga aggtaattat    120

cacataaatg aacttgttcc ctgtcaaata ttacggtgaa ttcgagttct gggtcgccaa    180

tatacgcgct cctgccc                                                   197


<210> SEQ ID NO 51
<211> LENGTH: 197
<212> TYPE: DNA
<213> ORGANISM: Artificial Sequence
<220> FEATURE:
<223> OTHER INFORMATION: Yeast editing cassette sequence

<400> SEQUENCE: 51

ggccccaaat tctaatttct actattgtag atggtaatta tcacaataat gatttttcat     60

tcaattttgg acgtacaaag ttccactggc ggcatggatt agtatttgga aggtaattat    120

cacataaatg aacttgttcc ctgtcaaata ttacggtgaa ttcgagttct gggtcgccaa    180

tatacgcgct cctgccc                                                   197


<210> SEQ ID NO 52
<211> LENGTH: 198
<212> TYPE: DNA
<213> ORGANISM: Artificial Sequence
<220> FEATURE:
<223> OTHER INFORMATION: Yeast editing cassette sequence

<400> SEQUENCE: 52

ggccccaaat tctaatttct actgtgtgta gatggtaatt atcacaataa tgatttttca     60

ttcaattttg gacgtacaaa gttccactgg cggcatggat tagtatttgg aaggtaatta    120

tcacataaat gaacttgttc cctgtcaaat attacggtga attcgagttc tgggtcgcca    180

atatacgcgc tcctgccc                                                  198
```

NUCLEIC ACID-GUIDED NUCLEASES

RELATED CASES

The present application is a continuation of U.S. Ser. No. 16/868,472, entitled "Nucleic Acid-Guided Nucleases," filed 6 May 2020, now U.S. Pat. No. 10,724,021; which is a continuation of U.S. Ser. No. 16/714,320, entitled "Nucleic Acid-Guided Nucleases," filed 13 Dec. 2019, now U.S. Pat. No. 10,704,033.

FIELD OF THE INVENTION

This invention relates to novel enzymes for making rational and direct edits to the genome of live cells.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the methods referenced herein do not constitute prior art under the applicable statutory provisions.

The ability to make precise, targeted changes to the genome of living cells has been a long-standing goal in biomedical research and development. Recently, various nucleases have been identified that allow manipulation of gene sequence, hence gene function. These nucleases include nucleic acid-guided nucleases. The range of target sequences that nucleic acid-guided nucleases can recognize, however, is constrained by the need for a specific PAM to be located near the desired target sequence. PAMs are short nucleotide sequences recognized by a gRNA/nuclease complex where this complex directs editing of the target sequence. The precise PAM sequence and pam length requirements for different nucleic acid-guided nucleases vary; however, PAMs typically are 2-7 base-pair sequences adjacent or in proximity to the target sequence and, depending on the nuclease, can be 5' or 3' to the target sequence. Screening the natural diversity of nucleic acid-guided nucleases that exist across species may allow for the discovery of enzymes with enhanced nuclease activity or increased cleavage fidelity when used in a given organism; both changes that may increase the versatility of a nucleic acid-guided nuclease for certain editing tasks.

There is thus a need in the art of nucleic acid-guided nuclease gene editing for improved nucleases with varied activity in cells from different organisms and/or altered enzyme fidelity. The novel MAD-series nucleases described herein satisfy this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present disclosure provides novel MAD-series nucleases with varied activity in cells from different organisms.

Thus, there is provided a novel MAD-series nuclease having a codon-optimized nucleic acid sequence comprising at least 65% homology to any of SEQ ID Nos. 3-7, 11, 13, 15-22 and 24. In some aspects, the novel MAD-series nuclease having a codon-optimized nucleic acid sequence comprises at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% homology to any of SEQ ID Nos. 3-7, 11, 13, 15-22 and 24

In some aspects, the novel MAD-series nucleases are in a system comprising a gRNA having an optimal crRNA variable loop comprising UGUU, UCUU OR UAUU.

Also provided is a novel MAD-series nuclease for editing in bacteria comprising at least 80% homology to any of SEQ ID Nos. 4, 11, 15, 16, 17, 19, 21, 22 or 24; and a novel MAD-series nuclease for editing in yeast comprising at least 80% homology to any of SEQ ID Nos. 3-6, 13, 15-22 or 24.

These aspects and other features and advantages of the invention are described below in more detail.

DETAILED DESCRIPTION

Figure 1:
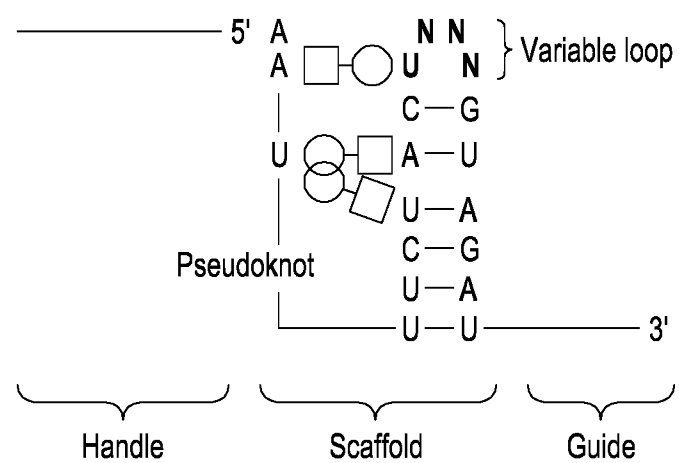
FIG. 1 depicts the minimal structure of a crRNA sequence delineating the scaffold (variable loop sequence), the location of the nuclease-targeting guide sequence and extended handle structures.

The description set forth below in connection with the appended drawings is intended to be a description of various, illustrative embodiments of the disclosed subject matter. Specific features and functionalities are described in connection with each illustrative embodiment; however, it will be apparent to those skilled in the art that the disclosed embodiments may be practiced without each of those specific features and functionalities. Moreover, all of the functionalities described in connection with one embodiment are intended to be applicable to the additional embodiments described herein except where expressly stated or where the feature or function is incompatible with the additional embodiments. For example, where a given feature or function is expressly described in connection with one embodiment but not expressly mentioned in connection with an alternative embodiment, it should be understood that the feature or function may be deployed, utilized, or implemented in connection with the alternative embodiment unless the feature or function is incompatible with the alternative embodiment.

The practice of the techniques described herein may employ, unless otherwise indicated, conventional techniques and descriptions of organic chemistry, polymer technology, molecular biology (including recombinant techniques), cell biology, biochemistry, biological emulsion generation, and sequencing technology, which are within the skill of those who practice in the art. Such conventional techniques include polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds. (1999), *Genome Analysis: A Laboratory Manual Series* (Vols. I-IV); Weiner, Gabriel, Stephens, Eds. (2007), *Genetic Variation: A Laboratory Manual*; Dieffenbach, Dveksler, Eds. (2003), *PCR Primer: A Laboratory Manual*; Bowtell and Sambrook (2003), *DNA Microarrays: A Molecular Cloning Manual*; Mount (2004), *Bioinformatics: Sequence and Genome Analysis*; Sambrook and Russell (2006), *Condensed Protocols from Molecular Cloning: A Laboratory Manual*; and Sambrook and Russell (2002), *Molecular Cloning: A Laboratory Manual* (all from Cold Spring Harbor Laboratory Press); Stryer, L. (1995) *Biochemistry* (4th Ed.) W. H. Freeman, New York N.Y.; Gait, "*Oligonucleotide Synthesis: A Practical Approach*" 1984, IRL Press, London; Nelson and Cox (2000), *Lehninger, Principles of Biochemistry* 3rd Ed., W. H. Freeman Pub., New York, N.Y.; Berg et al. (2002) *Biochemistry,* 5th Ed., W. H. Freeman Pub., New York, N.Y.; *Cell and Tissue Culture: Laboratory Procedures in Biotechnology* (Doyle & Griffiths, eds., John Wiley & Sons 1998); *Mammalian Chromosome Engineering—Methods and Protocols* (G. Hadlaczky, ed., Humana Press 2011); *Essential Stem Cell Methods*, (Lanza and Klimanskaya, eds., Academic Press 2011), all of which are herein incorporated in their entirety by reference for all purposes. Nuclease-specific techniques can be found in, e.g., *Genome Editing and Engineering From TALENs and CRISPRs to Molecular Surgery*, Appasani and Church, 2018; and *CRISPR: Methods and Protocols*, Lindgren and Charpentier, 2015; both of which are herein incorporated in their entirety by reference for all purposes. Basic methods for enzyme engineering may be found in, *Enzyme Engineering Methods and Protocols*, Samuelson, ed., 2013; *Protein Engineering*, Kaumaya, ed., (2012); and Kaur and Sharma, "*Directed Evolution: An Approach to Engineer Enzymes*", Crit. Rev. Biotechnology, 26:165-69 (2006).

Note that as used herein and in the appended claims, the singular forms "a," "an," and "the" include plural referents unless the context clearly dictates otherwise. Thus, for example, reference to "an oligonucleotide" refers to one or more oligonucleotides, and reference to "an automated system" includes reference to equivalent steps and methods for use with the system known to those skilled in the art, and so forth. Additionally, it is to be understood that terms such as "left," "right," "top," "bottom," "front," "rear," "side," "height," "length," "width," "upper," "lower," "interior," "exterior," "inner," "outer" that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, methods and cell populations that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of ordinary skill in the art that the present invention may be practiced without one or more of these specific details. In other instances, well-known features and procedures well known to those skilled in the art have not been described in order to avoid obscuring the invention.

The term "complementary" as used herein refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" or "percent homology" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'; and the nucleotide sequence 3'-TCGA-5' is 100% complementary to a region of the nucleotide sequence 5'-TAGCTG-3'.

The term DNA "control sequences" refers collectively to promoter sequences, polyadenylation signals, transcription termination sequences, upstream regulatory domains, origins of replication, internal ribosome entry sites, nuclear localization sequences, enhancers, and the like, which collectively provide for the replication, transcription and translation of a coding sequence in a recipient cell. Not all of these types of control sequences need to be present so long as a selected coding sequence is capable of being replicated, transcribed and—for some components—translated in an appropriate host cell.

As used herein the term "donor DNA" or "donor nucleic acid" refers to nucleic acid that is designed to introduce a DNA sequence modification (insertion, deletion, substitution) into a locus by homologous recombination using nucleic acid-guided nucleases. For homology-directed repair, the donor DNA must have sufficient homology to the regions flanking the "cut site" or site to be edited in the genomic target sequence.

The length of the homology arm(s) will depend on, e.g., the type and size of the modification being made. In many instances and preferably, the donor DNA will have two regions of sequence homology (e.g., two homology arms) to the genomic target locus. Preferably, an "insert" region or "DNA sequence modification" region—the nucleic acid modification that one desires to be introduced into a genome target locus in a cell—will be located between two regions of homology. The DNA sequence modification may change one or more bases of the target genomic DNA sequence at one specific site or multiple specific sites. A change may include changing 1, 2, 3, 4, 5, 10, 15, 20, 25, 30, 35, 40, 50, 75, 100, 150, 200, 300, 400, or 500 or more base pairs of the target sequence. A deletion or insertion may be a deletion or insertion of 1, 2, 3, 4, 5, 10, 15, 20, 25, 30, 40, 50, 75, 100, 150, 200, 300, 400, or 500 or more base pairs of the target sequence.

The terms "guide nucleic acid" or "guide RNA" or "gRNA" or "crRNA" refer to a polynucleotide comprising 1) a guide sequence capable of hybridizing to a genomic target locus, and 2) a scaffold sequence capable of interacting or complexing with a nucleic acid-guided nuclease (see, e.g., FIG. 1).

"Homology" or "identity" or "similarity" refers to sequence similarity between two peptides or, more often in the context of the present disclosure, between two nucleic acid molecules. The term "homologous region" or "homology arm" refers to a region on the donor DNA with a certain degree of homology with the target genomic DNA sequence. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

"Operably linked" refers to an arrangement of elements where the components so described are configured so as to perform their usual function. Thus, control sequences operably linked to a coding sequence are capable of effecting the transcription, and in some cases, the translation, of a coding sequence. The control sequences need not be contiguous with the coding sequence so long as they function to direct the expression of the coding sequence. Thus, for example, intervening untranslated yet transcribed sequences can be present between a promoter sequence and the coding sequence and the promoter sequence can still be considered "operably linked" to the coding sequence. In fact, such sequences need not reside on the same contiguous DNA molecule (i.e. chromosome) and may still have interactions resulting in altered regulation.

A "promoter" or "promoter sequence" is a DNA regulatory region capable of binding RNA polymerase and initiating transcription of a polynucleotide or polypeptide coding sequence such as messenger RNA, ribosomal RNA, small nuclear or nucleolar RNA, guide RNA, or any kind of RNA transcribed by any class of any RNA polymerase I, II or III. Promoters may be constitutive or inducible and, in some embodiments—particularly many embodiments in which selection is employed—the transcription of at least one component of the nucleic acid-guided nuclease editing system is under the control of an inducible promoter.

As used herein the term "selectable marker" refers to a gene introduced into a cell, which confers a trait suitable for artificial selection. General use selectable markers are well-known to those of ordinary skill in the art. Drug selectable markers such as ampicillin/carbenicillin, kanamycin, chloramphenicol, erythromycin, tetracycline, gentamicin, bleomycin, streptomycin, rhamnose, puromycin, hygromycin, blasticidin, and G418 may be employed. In other embodiments, selectable markers include, but are not limited to human nerve growth factor receptor (detected with a MAb, such as described in U.S. Pat. No. 6,365,373); truncated human growth factor receptor (detected with MAb); mutant human dihydrofolate reductase (DHFR; fluorescent MTX substrate available); secreted alkaline phosphatase (SEAP; fluorescent substrate available); human thymidylate synthase (TS; confers resistance to anti-cancer agent fluorodeoxyuridine); human glutathione S-transferase alpha (GSTA1; conjugates glutathione to the stem cell selective alkylator busulfan; chemoprotective selectable marker in CD34+cells); CD24 cell surface antigen in hematopoietic stem cells; human CAD gene to confer resistance to N-phosphonacetyl-L-aspartate (PALA); human multi-drug resistance-1 (MDR-1; P-glycoprotein surface protein selectable by increased drug resistance or enriched by FACS); human CD25 (IL-2a; detectable by Mab-FITC); Methylguanine-DNA methyltransferase (MGMT; selectable by carmustine); and Cytidine deaminase (CD; selectable by Ara-C). "Selective medium" as used herein refers to cell growth medium to which has been added a chemical compound or biological moiety that selects for or against selectable markers.

The terms "target genomic DNA sequence", "target sequence", or "genomic target locus" refer to any locus in vitro or in vivo, or in a nucleic acid (e.g., genome) of a cell or population of cells, in which a change of at least one nucleotide is desired using a nucleic acid-guided nuclease editing system. The target sequence can be a genomic locus or extrachromosomal locus.

A "vector" is any of a variety of nucleic acids that comprise a desired sequence or sequences to be delivered to and/or expressed in a cell. Vectors are typically composed of DNA, although RNA vectors are also available. Vectors include, but are not limited to, plasmids, fosmids, phagemids, virus genomes, synthetic chromosomes, and the like. As used herein, the phrase "engine vector" comprises a coding sequence for a nuclease to be used in the nucleic acid-guided nuclease systems and methods of the present disclosure. The engine vector may also comprise, in a bacterial system, the λ Red recombineering system or an equivalent thereto. Engine vectors also typically comprise a selectable marker. As used herein the phrase "editing vector" comprises a donor nucleic acid, optionally including an alteration to the target sequence that prevents nuclease binding at a PAM or spacer in the target sequence after editing has taken place, and a coding sequence for a gRNA. The editing vector may also comprise a selectable marker and/or a barcode. In some embodiments, the engine vector and editing vector may be combined; that is, the contents of the engine vector may be found on the editing vector. Further, the engine and editing vectors comprise control sequences operably linked to, e.g., the nuclease coding sequence, recombineering system coding sequences (if present), donor nucleic acid, guide nucleic acid, and selectable marker(s).

Editing in Nucleic Acid-Guided Nuclease Genome Systems

Nucleic acid-guided nucleases have been used to engineer the genomes of diverse organisms; however, differences in intrinsic DNA cutting activity, protein expression levels, cellular toxicity and activity in different organisms remain significant challenges that necessitates the screening of many candidate enzymes for editing in each organism. Nucleic acid-guided nucleases with demonstrated activity in vitro and/or in vivo in bacteria, fungi, or mammalian cells are therefore of great utility. The present disclosure provides novel gene editing MAD-series nucleases with varied PAM preferences, altered RNA-guided enzyme fidelity, and/or altered cellular toxicity or activity in different types of cells. That is, the novel MAD-series nucleases may be used to edit different cell types including, archaeal, prokaryotic, and eukaryotic (e.g., yeast, fungal, plant and animal) cells.

The novel MAD-series nucleases described herein improve RNA-guided enzyme editing systems in which nucleic acid-guided nucleases (e.g., RNA-guided nucleases) are used to edit specific target regions in an organism's genome. A nucleic acid-guided nuclease complexed with an appropriate synthetic guide nucleic acid in a cell can cut the genome of the cell at a desired location. The guide nucleic acid helps the nucleic acid-guided nuclease recognize and cut the DNA at a specific target sequence. By manipulating the nucleotide sequence of the guide nucleic acid, the nucleic acid-guided nuclease may be programmed to target any DNA sequence for cleavage as long as an appropriate protospacer adjacent motif (PAM) is nearby.

The novel MAD-series nucleases may be delivered to cells to be edited as a polypeptide; alternatively, a polynucleotide sequence encoding the novel MAD-series nuclease(s) is transformed or transfected into the cells to be edited. The polynucleotide sequence encoding the novel MAD-series nuclease may be codon optimized for expression in particular cells, such as archaeal, prokaryotic or eukaryotic cells. Eukaryotic cells can be yeast, fungi, algae, plant, animal, or human cells. Eukaryotic cells may be those of or derived from a particular organism, such as a mammal, including but not limited to human, mouse, rat, rabbit, dog, or non-human mammals including non-human primates. The choice of the novel MAD-series nuclease to be employed depends on many factors, such as what type of edit is to be made in the target sequence and whether an appropriate PAM is located close to the desired target sequence. The novel MAD-series nuclease may be encoded by a DNA sequence on a vector (e.g., the engine vector) and be under the control of a constitutive or inducible promoter. In some embodiments, the sequence encoding the nuclease is under the control of an inducible promoter, and the inducible promoter may be separate from but the same as an inducible promoter controlling transcription of the guide nucleic acid; that is, a separate inducible promoter may drive the transcription of the nuclease and guide nucleic acid sequences but the two inducible promoters may be the same type of inducible promoter (e.g., both are pL promoters). Alternatively, the inducible promoter controlling expression of the nuclease may be different from the inducible promoter controlling transcription of the guide nucleic acid; that is, e.g., the nuclease may be under the control of the pBAD inducible promoter, and the guide nucleic acid may be under the control of the pL inducible promoter.

In general, a guide nucleic acid (e.g., gRNA), also called a CRISPR RNA (e.g., crRNA), complexes with a compatible nucleic acid-guided nuclease and can then hybridize with a target sequence, thereby directing the nuclease to the target sequence. The gRNA may be encoded by a DNA sequence on a polynucleotide molecule such as a plasmid, linear construct, or the coding sequence may reside within an editing cassette and is under the control of a constitutive promoter, or, in some embodiments, an inducible promoter as described below. FIG. 1 depicts the minimal structure of the crRNA sequence delineating the scaffold (variable loop sequence), as well as the location of the nuclease-targeting guide sequence, pseudoknot and extended handle structures.

A guide nucleic acid comprises a guide sequence, where the guide sequence is a polynucleotide sequence having sufficient complementarity with a target sequence to hybridize with the target sequence and direct sequence-specific binding of a complexed nucleic acid-guided nuclease to the target sequence. The degree of complementarity between a guide sequence and the corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences. In some embodiments, a guide sequence is about or more than about 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20 nucleotides in length. Preferably the guide sequence is 10-30 or 15-20 nucleotides long, or 15, 16, 17, 18, 19, or 20 nucleotides in length.

In the present methods and compositions, the guide nucleic acid is provided as a sequence to be expressed from a plasmid or vector and comprises both the guide sequence and the scaffold sequence as a single transcript under the control of a promoter, and in some embodiments, an inducible promoter. The guide nucleic acid can be engineered to target a desired target sequence by altering the guide sequence so that the guide sequence is complementary to a desired target sequence, thereby allowing hybridization between the guide sequence and the target sequence. In general, to generate an edit in the target sequence, the gRNA/nuclease complex binds to a target sequence as determined by the guide RNA, and the nuclease recognizes a proto spacer adjacent motif (PAM) sequence adjacent to the target sequence. The target sequence can be any polynucleotide endogenous or exogenous to a prokaryotic or eukaryotic cell, or in vitro. For example, the target sequence can be a polynucleotide residing in the nucleus of a eukaryotic cell. A target sequence can be a sequence encoding a gene product (e.g., a protein) or a non-coding sequence (e.g., a regulatory polynucleotide, an intron, a PAM, or "junk" DNA).

The guide nucleic acid may be part of an editing cassette that encodes the donor nucleic acid. Alternatively, the guide nucleic acid may not be part of the editing cassette and instead may be encoded on the engine or editing vector backbone. For example, a sequence coding for a guide nucleic acid can be assembled or inserted into a vector backbone first, followed by insertion of the donor nucleic acid in, e.g., the editing cassette. In other cases, the donor nucleic acid in, e.g., an editing cassette can be inserted or assembled into a vector backbone first, followed by insertion of the sequence coding for the guide nucleic acid. In yet other cases, the sequence encoding the guide nucleic acid and the donor nucleic acid (inserted, for example, in an editing cassette) are simultaneously but separately inserted or assembled into a vector. In yet other embodiments, the sequence encoding the guide nucleic acid and the sequence encoding the donor nucleic acid are both included in the editing cassette.

The target sequence is associated with a PAM, which is a short nucleotide sequence recognized by the gRNA/nuclease complex. The precise PAM sequence and length requirements for different nucleic acid-guided nucleases vary; however, PAMs typically are 2-7 base-pair sequences adjacent or in proximity to the target sequence and, depending on the nuclease, can be 5' or 3' to the target sequence. Engineering of the PAM-interacting domain of a nucleic acid-guided nuclease may allow for alteration of PAM specificity, improve fidelity, or decrease fidelity. In certain embodiments, the genome editing of a target sequence both introduces a desired DNA change to a target sequence, e.g., the genomic DNA of a cell, and removes, mutates, or renders inactive a proto-spacer mutation (PAM) region in the target sequence. Rendering the PAM at the target sequence inactive precludes additional editing of the cell genome at that target sequence, e.g., upon subsequent exposure to a nucleic acid-guided nuclease complexed with a synthetic guide nucleic acid in later rounds of editing. Thus, cells having the desired target sequence edit and an altered PAM can be selected using a nucleic acid-guided nuclease complexed with a synthetic guide nucleic acid complementary to the target sequence. Cells that did not undergo the first editing event will be cut rendering a double-stranded DNA break, and thus will not continue to be viable. The cells containing the desired target sequence edit and PAM alteration will not be cut, as these edited cells no longer contain the necessary PAM site and will continue to grow and propagate.

Another component of the nucleic acid-guided nuclease system is the donor nucleic acid. In some embodiments, the donor nucleic acid is on the same polynucleotide (e.g., editing vector or editing cassette) as the guide nucleic acid and may be (but not necessarily) under the control of the same promoter as the guide nucleic acid (e.g., a single promoter driving the transcription of both the guide nucleic acid and the donor nucleic acid). The donor nucleic acid is designed to serve as a template for homologous recombination with a target sequence nicked or cleaved by the nucleic acid-guided nuclease as a part of the gRNA/nuclease complex. A donor nucleic acid polynucleotide may be of any suitable length, such as about or more than about 20, 25, 50, 75, 100, 150, 200, 500, or 1000 nucleotides in length. In certain preferred aspects, the donor nucleic acid can be provided as an oligonucleotide of between 20-300 nucleotides, more preferably between 50-250 nucleotides. The donor nucleic acid comprises a region that is complementary to a portion of the target sequence (e.g., a homology arm). When optimally aligned, the donor nucleic acid overlaps with (is complementary to) the target sequence by, e.g., about 20, 25, 30, 35, 40, 50, 60, 70, 80, 90 or more nucleotides. In many embodiments, the donor nucleic acid comprises two homology arms (regions complementary to the target sequence) flanking the mutation or difference between the donor nucleic acid and the target template. The donor nucleic acid comprises at least one mutation or alteration compared to the target sequence, such as an insertion, deletion, modification, or any combination thereof compared to the target sequence.

Often the donor nucleic acid is provided as an editing cassette, which is inserted into a vector backbone where the vector backbone may comprise a promoter driving transcription of the gRNA and the coding sequence of the gRNA, or the vector backbone may comprise a promoter driving the transcription of the gRNA but not the gRNA itself. Moreover, there may be more than one, e.g., two, three, four, or more guide nucleic acid/donor nucleic acid cassettes inserted into an engine vector, where each guide nucleic acid is under the control of separate different promoters, separate like promoters, or where all guide nucleic acid/donor nucleic acid pairs are under the control of a single promoter. In some embodiments—such as embodiments where cell selection is employed—the promoter driving transcription of the gRNA and the donor nucleic acid (or driving more than one gRNA/donor nucleic acid pair) is an inducible promoter. Inducible editing is advantageous in that singulated cells can be grown for several to many cell doublings before editing is initiated, which increases the likelihood that cells with edits will survive, as the double-strand cuts caused by active editing are largely toxic to the cells. This toxicity results both in cell death in the edited colonies, as well as a lag in growth for the edited cells that do survive but must repair and recover following editing. However, once the edited cells have a chance to recover, the size of the colonies of the edited cells will eventually catch up to the size of the colonies of unedited cells. See, e.g., U.S. Ser. No. 16/399,988, filed 30 Apr. 2019; U.S. Ser. No. 16/454,865, filed 26 Jun. 2019; and U.S. Ser. No. 16/540,606, filed 14 Aug. 2019. Further, a guide nucleic acid may be efficacious directing the edit of more than one donor nucleic acid in an editing cassette; e.g., if the desired edits are close to one another in a target sequence.

In addition to the donor nucleic acid, an editing cassette may comprise one or more primer sites. The primer sites can be used to amplify the editing cassette by using oligonucleotide primers; for example, if the primer sites flank one or more of the other components of the editing cassette.

In addition, the editing cassette may comprise a barcode. A barcode is a unique DNA sequence that corresponds to the donor DNA sequence such that the barcode can identify the edit made to the corresponding target sequence. The barcode typically comprises four or more nucleotides. In some embodiments, the editing cassettes comprise a collection of donor nucleic acids representing, e.g., gene-wide or genome-wide libraries of donor nucleic acids. The library of editing cassettes is cloned into vector backbones where, e.g., each different donor nucleic acid is associated with a different barcode.

Additionally, in some embodiments, an expression vector or cassette encoding components of the nucleic acid-guided nuclease system further encodes a novel MAD-series nuclease comprising one or more nuclear localization sequences (NLSs), such as about or more than about 1, 2, 3, 4, 5, 6, 7, 8, 9, 10, or more NLSs. In some embodiments, the novel nuclease comprises NLSs at or near the amino-terminus, NLSs at or near the carboxy-terminus, or a combination.

The engine and editing vectors comprise control sequences operably linked to the component sequences to be transcribed. As stated above, the promoters driving transcription of one or more components of the novel MAD-series nuclease editing system may be inducible, and an inducible system is likely employed if selection is to be performed. A number of gene regulation control systems have been developed for the controlled expression of genes in plant, microbe, and animal cells, including mammalian cells, including the pL promoter (induced by heat inactivation of the CI857 repressor), the pBAD promoter (induced by the addition of arabinose to the cell growth medium), and the rhamnose inducible promoter (induced by the addition of rhamnose to the cell growth medium). Other systems include the tetracycline-controlled transcriptional activation system (Tet-On/Tet-Off, Clontech, Inc. (Palo Alto, Calif.); Bujard and Gossen, PNAS, 89(12):5547-5551 (1992)), the Lac Switch Inducible system (Wyborski et al., Environ Mol Mutagen, 28(4):447-58 (1996); DuCoeur et al., Strategies 5(3):70-72 (1992); U.S. Pat. No. 4,833,080), the ecdysone-inducible gene expression system (No et al., PNAS, 93(8): 3346-3351 (1996)), the cumate gene-switch system (Mullick et al., BMC Biotechnology, 6:43 (2006)), and the tamoxifen-inducible gene expression (Zhang et al., Nucleic Acids Research, 24:543-548 (1996)) as well as others.

Typically, performing genome editing in live cells entails transforming cells with the components necessary to perform nucleic acid-guided nuclease editing. For example, the cells may be transformed simultaneously with separate engine and editing vectors; the cells may already be expressing the novel MAD-series nuclease (e.g., the cells may have already been transformed with an engine vector or the coding sequence for the novel MAD-series nuclease may be stably integrated into the cellular genome) such that only the editing vector needs to be transformed into the cells; or the cells may be transformed with a single vector comprising all components required to perform nucleic acid-guided nuclease genome editing.

A variety of delivery systems can be used to introduce (e.g., transform or transfect) nucleic acid-guided nuclease editing system components into a host cell. These delivery systems include the use of yeast systems, lipofection systems, microinjection systems, biolistic systems, virosomes, liposomes, immunoliposomes, polycations, lipid:nucleic acid conjugates, virions, artificial virions, viral vectors, electroporation, cell permeable peptides, nanoparticles, nanowires, exosomes. Alternatively, molecular trojan horse liposomes may be used to deliver nucleic acid-guided nuclease components across the blood brain barrier. Of particular interest is the use of electroporation, particularly flow-through electroporation (either as a stand-alone instrument or as a module in an automated multi-module system) as described in, e.g., U.S. Ser. Nos. 16/024,831; 62/566,375; 62/566,688; and 62/567,697.

After the cells are transformed with the components necessary to perform nucleic acid-guided nuclease editing, the cells are cultured under conditions that promote editing. For example, if constitutive promoters are used to drive transcription of the novel MAD-series nucleases and/or gRNA, the transformed cells need only be cultured in a typical culture medium under typical conditions (e.g., temperature, $CO_2$ atmosphere, etc.) Alternatively, if editing is inducible—by, e.g., activating inducible promoters that control transcription of one or more of the components needed for nucleic acid-guided nuclease editing, such as, e.g., transcription of the gRNA, donor DNA, nuclease, or, in the case of bacteria, a recombineering system—the cells are subjected to inducing conditions.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Example 1: Exemplary Workflow Overview

Figure 2:
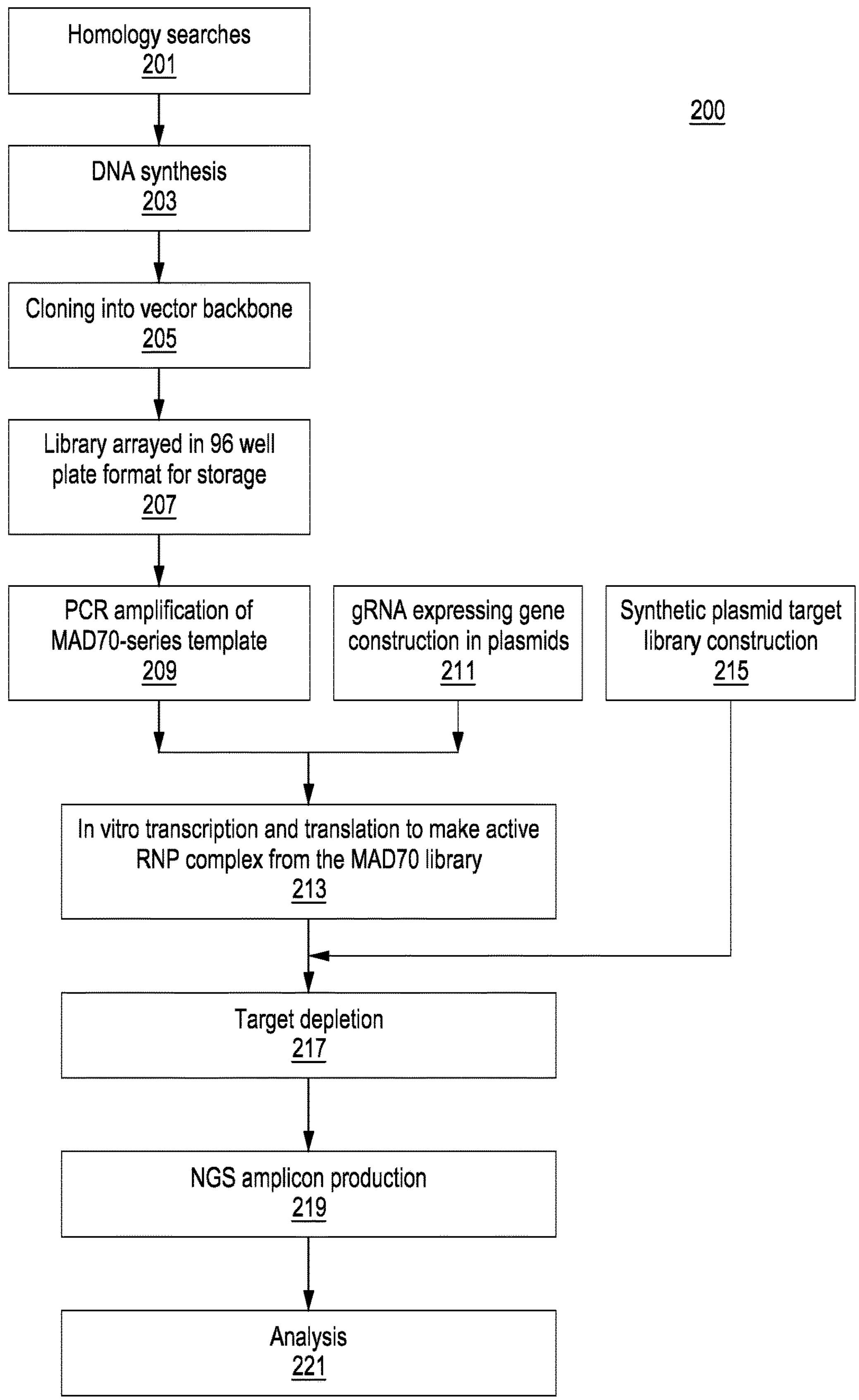
FIG. 2 is an exemplary workflow for identifying, producing, and screening the targeted nuclease activity of novel MAD-series enzymes

FIG. 2 shows an exemplary workflow 200 for creating and for in vitro screening novel MAD-series enzymes. In the first step 201, computational sequence homology searches using MAD7 as the query sequence were performed and a set of putative RNA-guided nucleases selected. In step 203, sequences with different levels of homology to MAD7 were selected for DNA synthesis with *E. coli* optimized codon bias. Selected sequences included four very close orthologs of MAD7 designated MAD7v1, MADv2, MAD7v3 and MAD7v4. Sequences with greater divergence from MAD7 were designated MAD2 through MAD110. In step 205, these synthetic genes were cloned into a vector backbone and single colonies yielding correct sequences confirmed by Sanger DNA sequencing.

The cells transformed with the novel MAD-series enzymes were arrayed in 96-well plates 207 for storage. At step 209, an aliquot of the cells from each well was taken, and the MAD-series sequences were amplified from each aliquot. At another step 211, a plasmid expressing a gRNA was constructed and combined with the amplified MAD-series nucleases to perform in vitro transcription and translation to make active ribonuclease protein complexes 213. A synthetic target library was constructed 215 in which to test target depletion 217 for each of the MAD-series variants. After target depletion, amplicons were produced for analysis using next-gen sequencing 219 and sequencing data analysis was performed 221 to determine target depletion.

Example 2: Vector Cloning and Novel MAD-Series Enzyme PCR for Template Generation The novel MAD-series enzyme coding sequences were cloned into a pUC57 vector with T7-promoter sequence attached to the 5'-end of the coding sequence and a T7-terminator sequence attached to the 3'-end of the coding sequence.

First, Q5 Hot Start 2x master mix reagent (NEB, Ipswich, Mass.) was used to amplify the novel MAD-series sequences using the pUC57 plasmid as a source of MAD-series templates. The forward primer 5'-TTGGGTAACGCCAGGGTTTT [SEQ ID No. 27] and reverse primer 5'-TGTGTGGAATTGTGAGCGGA [SEQ ID No. 28] amplified the sequences flanking the novel MAD-series variant in the pUC57 vector including the T7-promoter and T7-terminator components attached to the MAD7 variant sequence at the 5'- and 3'-end of the novel MAD-series variants, respectively. 1 μM primers and 5 ng/uL pUC57 template were used in PCR reactions to generate linear dsDNA product encoding the novel MAD-series variant. The PCR conditions shown in Table 1 were used:

TABLE 1

| STEP | TEMPERATURE | TIME |
|---|---|---|
| DENATURATION | 98° C. | 30 SEC |
| 30 CYCLES | 98° C. | 10 SEC |
| | 66° C. | 30 SEC |
| | 72° C. | 2.5 MIN |
| FINAL EXTENSION | 72° C. | 2 MIN |
| HOLD | 12° C. | |

Example 3: In Vitro Transcription and Translation for Production of MAD-Series Nucleases and gRNAs in a Single Well A PURExpress® In Vitro Protein Synthesis Kit (NEB, Ipswich, Mass.) was used to produce novel MAD-series variant proteins from the PCR-amplified linear dsDNA template and also to produce gRNAs. In each well in a 96-well plate, the reagents listed in Table 2 were mixed to start the production of MAD7 variants and gRNA:

TABLE 2

| | REAGENTS | VOLUME (μl) |
|---|---|---|
| 1 | SolA (NEB kit) | 3.3 |
| 2 | SolB (NEB kit) | 2.5 |

TABLE 2-continued

| | REAGENTS | VOLUME (µl) |
|---|---|---|
| 3 | gRNA mix (4 ng/µl stock) | 0.8 |
| 4 | Murine RNase inhibitor (NEB) | 0.2 |
| 5 | Water | 0.5 |
| 6 | PCR amplified T7 MAD-series variants | 1.0 |

A master mix with all reagents except the PCR-amplified T7-MAD-series variants was prepared and kept on ice. After 7.3 µL of the master mix was distributed in each well in 96 well plates, 1 µL of the PCR amplified MAD-series variants under the control of T7 promoter was added. The 96-well plates were sealed and incubated for 4 hrs at 37° C. in a thermal cycler. The plates were kept at room temperature until the target pool was added to perform the target depletion reaction.

Example 4: Performing Target Depletion, PCR and NGS

After 4 hours incubation to allow production of the novel MAD-series variants and gRNAs, 4 µL of the target library pool (10 ng/µL) was added to the in vitro transcription/translation reaction mixture. After the target library was added, reaction mixtures were incubated overnight at 37° C. The target depletion reaction mixtures were diluted into PCR-grade water that contains RNAse A and then boiled for 5 min at 95° C. The mixtures were then amplified and sequenced. The PCR conditions are shown in Table 3:

TABLE 3

| STEP | TEMPERATURE | TIME |
|---|---|---|
| DENATURATION | 98° C. | 30 SEC |
| 6 CYCLES | 98° C. | 10 SEC |
| | 61° C. | 30 SEC |
| | 72° C. | 10 SEC |
| 22 CYCLES | 98° C. | 10 SEC |
| | 72° C. | 10 SEC |
| FINAL EXTENSION | 72° C. | 2 MINUTES |
| HOLD | 12° C. | |

Table 4 shows the results of the in vitro assay.

TABLE 4

| Nuclease | Native crRNA loop | Active in vitro | Optimal crRNA loop (variable loop - see FIG. 1) | SEQ ID NO. |
|---|---|---|---|---|
| MAD7 | UGUU | Active | UGUU | SEQ ID No. 1 |
| MAD7v1 | UGUU | Active | UGUU | SEQ ID No. 3 |
| MAD7v2 | UGUU | Active | UGUU | SEQ ID No. 4 |
| MAD7v3 | UGUU | Active | UGUU | SEQ ID No. 5 |
| MAD7v4 | UGUU | Active | UGUU | SEQ ID No. 6 |
| MAD2 | Unknown | Active | UGUU, UCUU | SEQ ID No. 7 |
| MAD3 | UCUUU | Active | UCUUU | SEQ ID No. 8 |
| MAD4 | UGUU | Active | UGUU, UCUU | SEQ ID No. 9 |
| MAD5 | UAGU | Inactive | UAGU | SEQ ID No. 10 |
| MAD6 | UAUU | Active | UAUU | SEQ ID No. 11 |
| MAD12 | UCUU | Active | UCUU, UAUU | SEQ ID No. 12 |
| MAD31 | unknown | Active | UCUU, UAUU | SEQ ID No. 13 |
| MAD35 | unknown | Active | UGUU, UAUU | SEQ ID No. 14 |
| MAD41 | UGUGU | Active | UAUU, UCUU | SEQ ID No. 15 |
| MAD44 | UAUU | Active | UCUU, UAUU | SEQ ID No. 16 |
| MAD50 | UGUU | Active | UCUU, UGUU | SEQ ID No. 17 |
| MAD53 | unknown | Active | UAUU | SEQ ID No. 18 |
| MAD54 | unknown | Active | UGUU | SEQ ID No. 19 |
| MAD57 | UAGU | Active | UAUU | SEQ ID No. 20 |
| MAD82 | UGUU | Active | UCUU, UGUU | SEQ ID No. 21 |
| MAD89 | UAUU | Active | UGUU, UAUU | SEQ ID No. 22 |

TABLE 4-continued

| Nuclease | Native crRNA loop | Active in vitro | Optimal crRNA loop (variable loop - see FIG. 1) | SEQ ID NO. |
|---|---|---|---|---|
| MAD90 | unknown | Active | UAUU, UGUU | SEQ ID No. 23 |
| MAD92 | UAUU | Weakly Active | UAUU | SEQ ID No. 24 |
| MAD8 | UAUU | Inactive | | |
| MAD10 | UUUU | Inactive | | |
| MAD28 | UUUU | Inactive | | |
| MAD29 | Unknown | Inactive | | |
| MAD30 | UUUU | Inactive | | |
| MAD32 | UUUU | Inactive | | |
| MAD33 | UUUU | Inactive | | |
| MAD37 | Unknown | Inactive | | |
| MAD38 | uACUAu | Inactive | | |
| MAD40 | UUUU | Inactive | | |
| MAD43 | UUUU | Inactive | | |
| MAD45 | unknown | Inactive | | |
| MAD49 | UUUU | Inactive | | |
| MAD52 | UUCG | Inactive | | |
| MAD71 | unknown | Inactive | | |
| MAD95 | unknown | Inactive | | |
| MAD107 | unknown | Inactive | | |
| MAD108 | UGUU | Inactive | | |
| MAD110 | unknown | Inactive | | |

Example 5: *E. coli* Genome Editing

Library Amplification:

50 µL reactions were run with 5 µL of the diluted synthetic oligonucleotide editing cassettes from a chip. The PCR conditions were 95° C. for 1 minute, then 18 rounds of 95° C. for 30 seconds/60° C. for 30 seconds/72° C. for 2 minutes 30 seconds with a final hold at 72° C. for 5 minutes. The product was run on an agarose gel to check for homogeneity. For amplifying the backbone, ten-fold serial dilutions were performed of the pL backbone—a backbone with the pL inducible promoter positioned to drive transcription of the galK editing cassette. The PCR conditions were 95° C. for 1 minute, then 30 rounds of 95° C. for 1 minute/60° C. for 1 minute 30 seconds/72° C. for 2 minutes 30 seconds with a final hold at 72° C. for 5 minutes. Again, the product was run on an agarose gel to check for homogeneity. Amplicons were pooled, miniprepped, and 6 µL of CUTSMART® (NEB, Ipswich, Mass.) enzyme was added and the digestion was allowed to proceed at 37° C. for 1 hour. The linearized backbone was quantified before isothermal assembly with the purified cassette library.

A Gibson reaction was performed with 150 ng backbone, 100 ng insert, and GIBSON® (NEB, Ipswich Mass.) MASTER MIX. The reaction was incubated for 45 minutes at 50° C. The reaction was dialyzed for 30 minutes. 5 µL of the dialyzed Gibson reaction was transformed into E. cloni competent cells. The E.cloni® SUPREME electrocompetent cells (Lucigen, Middleton Wis.) were outgrown in 25 ML SOB+100 µg/mL Carb and a midiprep was performed. 100 ng of the cloned library was transformed into 50 µL competent cells at 2400V in a 2 mm cuvette. The cells were allowed to recover in SOB and 10-fold dilutions were spot-plated. To induce editing, 50 µL of outgrowth was transferred into SOB/chlor/carb/1% arabinose in a well plate. The cells were allowed to reach mid log phase and then were incubated at 42° C. for 2-2.5 hours. Serial dilutions were performed and the cells were plated to determine editing efficiency.

Figure 3:
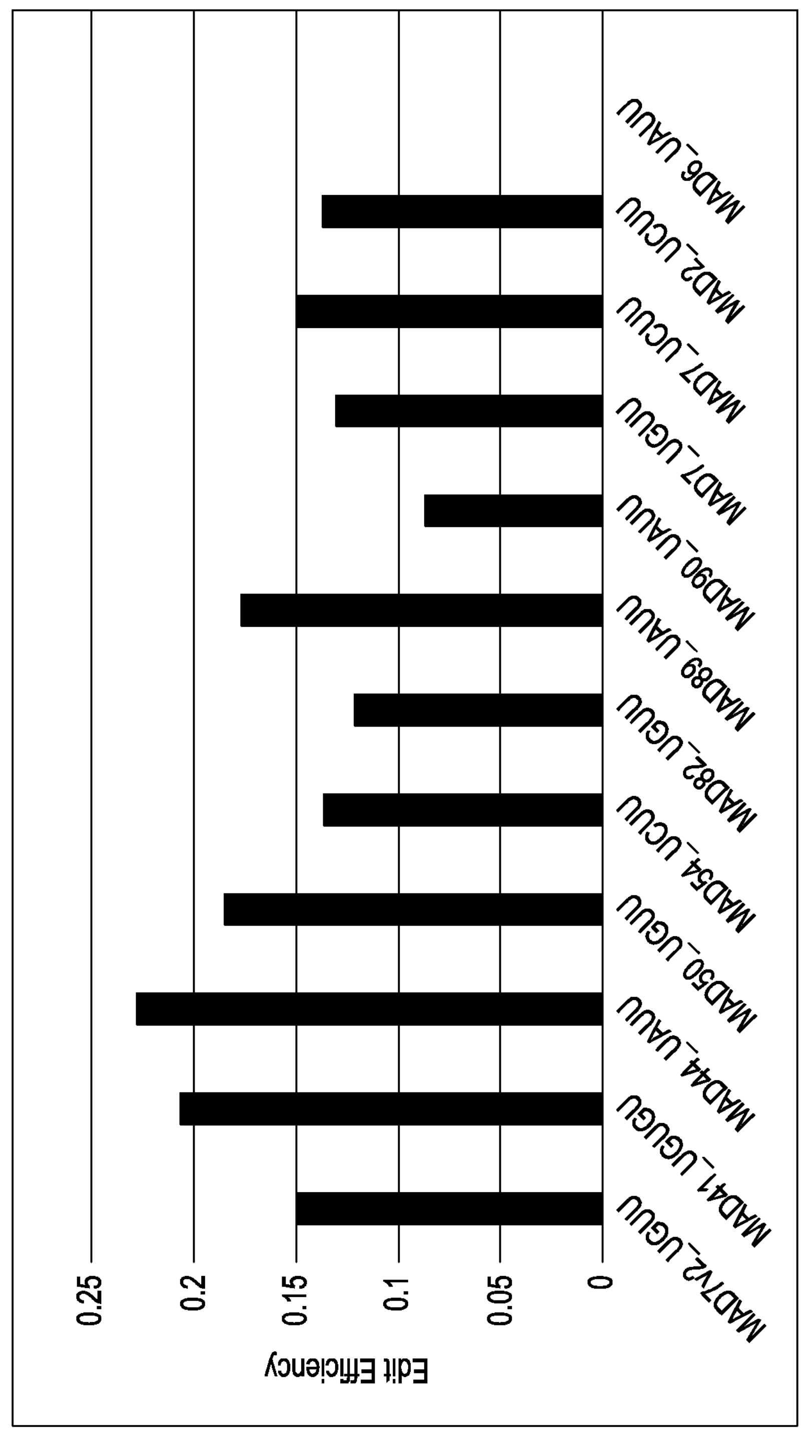
FIG. 3 shows the results of editing in *E. coli* as assessed by colorimetric screening of precise edits in the galK locus by the indicated MAD-series nuclease with the indicated variable loop sequence.

FIG. 3 shows the results of in vivo editing of *E. coli* assessed by colorimetric screening of precise edits in the galK locus by the indicated protein with the indicated variable loop sequence. Table 5 shows the results of in vivo *E. coli* editing:

TABLE 5

| Nuclease | Active in *E. coli* | crRNA loop | SEQ ID No. |
|---|---|---|---|
| MAD7 | Active | UGUU, UCUU | SEQ ID No. 1 |
| MAD7v2 | Active | UGUU | SEQ ID No. 4 |
| MAD2 | Active | UCUU | SEQ ID No. 7 |
| MAD3 | Inactive | | SEQ ID No. 8 |
| MAD4 | Inactive | | SEQ ID No. 9 |
| MAD6 | Weakly Active | UAUU | SEQ ID No. 11 |
| MAD41 | Active | UGUGU | SEQ ID No. 15 |
| MAD44 | Active | UAUU | SEQ ID No. 16 |
| MAD50 | Active | UGUU | SEQ ID No. 17 |
| MAD54 | Active | UCUU | SEQ ID No. 19 |
| MAD82 | Active | UGUU | SEQ ID No. 21 |
| MAD89 | Active | UAUU | SEQ ID No. 22 |
| MAD92 | Active | UAUU | SEQ ID No. 24 |

Example 6: *S. cerevisiae* Genome Editing

For the enzymes that showed activity in vitro, the genome editing activity was tested in vivo in *S. cerevisiae*. A two-micron plasmid with the KanMX resistance gene was constructed for the sequential introduction of DNA containing an editing cassette with SNR52 promoter-driven crRNA and a CYC1 promoter-driven nuclease protein. The editing cassette consisted of the crRNA to guide the nuclease to cut at a specific DNA sequence, a short pentaT linker, and a repair template containing the mutation of interest flanked by regions of homology to the genome. The screening plasmid was linearized by the StuI restriction endonuclease, and the editing cassette was introduced downstream of the SNR52p promoter by isothermal assembly. The editing cassettes (see Table 6 below) all targeted TTTV PAM sequences in the CAN1 locus and introduce a premature stop codon to knock out the functional Can1 protein.

TABLE 6

List of yeast editing cassette sequences tested

| Cassette name | PAM Targeted | crRNA scaffold | Yeast Editing Cassette Sequence | SEQ ID No. |
|---|---|---|---|---|
| Can1_S3 0 stop | TTTA | UGUU | GGCCCCAAATTCTAATTTCTAC**TGTT**GTAGATACGACGTTGAAGCTTCACAATTTTTACGCCGACATAGAGGAGAAGCATATGTACAATGAGCCGGTCACAACCCTCGAGACACGACGTTGAAGCTTAACAAACACACCACAGACGTGGGTCAATACCATTGAAAGATGAGAAAAGTAACAATATACGCGCTCCTGCCC | SEQ ID No. 29 |
| Can1_S3 0 stop | TTTA | UCUU | GGCCCCAAATTCTAATTTCTAC**TCTT**GTAGATACGACGTTGAAGCTTCACAATTTTTACGCCGACATAGAGGAGAAGCATATGTACAATGAGCCGGTCACAACCCTCGAGACACGACGTTGAAGCTTAACAAACACACCACAGACGTGGGTCAATACCATTGAAAGATGAGAAAAGTAACAATATACGCGCTCCTGCCC | SEQ ID No. 30 |
| Can1_53 0 stop | TTTA | UAUU | GGCCCCAAATTCTAATTTCTAC**TATT**GTAGATACGACGTTGAAGCTTCACAATTTTTACGCCGACATAGAGGAGAAGCATATGTACAATGAGCCGGTCACAACCCTCGAGACACGACGTTGAAGCTTAACAAACACACCACAGACGTGGGTCAATACCATTGAAAGATGAGAAAAGTAACAATATACGCGCTCCTGCCC | SEQ ID No. 31 |
| Can1_53 0 stop | TTTA | UGUGU | GGCCCCAAATTCTAATTTCTAC**TGTGT**GTAGATACGACGTTGAAGCTTCACAATTTTTACGCCGACATAGAGGAGAAGCATATGTACAATGAGCCGGTCACAACCCTCGAGACACGACGTTGAAGCTTAACAAACACACCACAGACGTGGGTCAATACCATTGAAAGATGAGAAAAGTAACAATATACGCGCTCCTGCCC | SEQ ID No. 32 |
| Can1_K4 2 stop | TTTA | UGUU | GGCCCCAAATTCTAATTTCTAC**TGTT**GTAGATCTTTTCTCATCTTTCAATGGTTTTTGTATCCTCGCCATTTACTCTCGTCGGGAAAGAGCGCAATGGATACAATTCCCCACTTTTCTCATCTTACAATGGTATTGACCCACGTCTGTGGTGTGTTTGTGAAGCTTCAACGTCGTCAATATACGCGCTCCTGCCC | SEQ ID No. 33 |
| Can1_K4 2 stop | TTTA | UCUU | GGCCCCAAATTCTAATTTCTAC**TCTT**GTAGATCTTTTCTCATCTTTCAATGGTTTTTGTATCCTCGCCATTTACTCTCGTCGGGAAAGAGCGCAATGGATACAATTCCCCACTTTTCTCATCTTACAATGGTATTGACCCACGTCTGTGGTGTGTTTGTGAAGCTTCAACGTCGTCAATATACGCGCTCCTGCCC | SEQ ID No. 34 |

TABLE 6 -continued

List of yeast editing cassette sequences tested

| Cassette name | PAM Targeted | crRNA scaffold | Yeast Editing Cassette Sequence | SEQ ID No. |
|---|---|---|---|---|
| Can1_K4 2 stop | TTTA | UAUU | GGCCCCAAATTCTAATTTCTAC**TATT**GTAG ATCTTTTCTCATCTTTCAATGGTTTTTGTAT CCTCGCCATTTACTCTCGTCGGGAAAGAG CGCAATGGATACAATTCCCCACTTTTCTCA TCTTACAATGGTATTGACCCACGTCTGTGG TGTGTTTGTGAAGCTTCAACGTCGTCAATA TACGCGCTCCTGCCC | SEQ ID No. 35 |
| Can1_K4 2 stop | TTTA | UGUGU | GGCCCCAAATTCTAATTTCTAC**TGTGT**GT AGATCTTTTCTCATCTTTCAATGGTTTTTGT ATCCTCGCCATTTACTCTCGTCGGGAAAGA GCGCAATGGATACAATTCCCCACTTTTCTC ATCTTACAATGGTATTGACCCACGTCTGTG GTGTGTTTGTGAAGCTTCAACGTCGTCAAT ATACGCGCTCCTGCCC | SEQ ID No. 36 |
| Can1_N6 0 stop | TTTC | UGUU | GGCCCCAAATTCTAATTTCTAC**TGTT**GTAG ATCCGACGAGAGTAAATGGCGATTTTTTC AATACCATTGAAAGATGAGAAAAGTAAAG AATTGTATCCATTGCGCTCGTTCCCGACGA GAGTATAAGGCGAGGATACGTTCTCTATG GAGGATGGCATAGGTGATGAAGATGAAG GAGAAGCAATATACGCGCTCCTGCCC | SEQ ID No. 37 |
| Can1_N6 0 stop | TTTC | UCUU | GGCCCCAAATTCTAATTTCTAC**TCTT**GTAG ATCCGACGAGAGTAAATGGCGATTTTTTC AATACCATTGAAAGATGAGAAAAGTAAAG AATTGTATCCATTGCGCTCGTTCCCGACGA GAGTATAAGGCGAGGATACGTTCTCTATG GAGGATGGCATAGGTGATGAAGATGAAG GAGAAGCAATATACGCGCTCCTGCCC | SEQ ID No. 38 |
| Can1_N6 0 stop | TTTC | UAUU | GGCCCCAAATTCTAATTTCTAC**TATT**GTAG ATCCGACGAGAGTAAATGGCGATTTTTTC AATACCATTGAAAGATGAGAAAAGTAAAG AATTGTATCCATTGCGCTCGTTCCCGACGA GAGTATAAGGCGAGGATACGTTCTCTATG GAGGATGGCATAGGTGATGAAGATGAAG GAGAAGCAATATACGCGCTCCTGCCC | SEQ ID No. 39 |
| Can1_N6 0 stop | TTTC | UGUGU | GGCCCCAAATTCTAATTTCTAC**TGTGT**GT AGATCCGACGAGAGTAAATGGCGATTTTT TCAATACCATTGAAAGATGAGAAAAGTAA AGAATTGTATCCATTGCGCTCGTTCCCGAC GAGAGTATAAGGCGAGGATACGTTCTCTA TGGAGGATGGCATAGGTGATGAAGATGAA GGAGAAGCAATATACGCGCTCCTGCCC | SEQ ID No. 40 |
| Can1_T1 15 stop | TTTA | UGUU | GGCCCCAAATTCTAATTTCTAC**TGTT**GTAG ATTCCACACCTCTGACCAACGCTTTTTATT GGTATGATTGCCCTTGGTGGTACTATTGGT ACAGGTCTTTTCATTGGATTATCCACACCT CTGTAAAACGCCGGCCCAGTGGGCGCTCT TATATCATATTTATTTATGGGTTCTTTGGC ATCAATATACGCGCTCCTGCCC | SEQ ID No. 41 |
| Can1_T1 15 stop | TTTA | UCUU | GGCCCCAAATTCTAATTTCTAC**TCTT**GTAG ATTCCACACCTCTGACCAACGCTTTTTATT GGTATGATTGCCCTTGGTGGTACTATTGGT ACAGGTCTTTTCATTGGATTATCCACACCT CTGTAAAACGCCGGCCCAGTGGGCGCTCT TATATCATATTTATTTATGGGTTCTTTGGC ATCAATATACGCGCTCCTGCCC | SEQ ID No. 42 |
| Can1_T1 15 stop | TTTA | UAUU | GGCCCCAAATTCTAATTTCTAC**TATT**GTAG ATTCCACACCTCTGACCAACGCTTTTTATT GGTATGATTGCCCTTGGTGGTACTATTGGT ACAGGTCTTTTCATTGGATTATCCACACCT CTGTAAAACGCCGGCCCAGTGGGCGCTCT TATATCATATTTATTTATGGGTTCTTTGGC ATCAATATACGCGCTCCTGCCC | SEQ ID No. 43 |

TABLE 6 -continued

List of yeast editing cassette sequences tested

| Cassette name | PAM Targeted | crRNA scaffold | Yeast Editing Cassette Sequence | SEQ ID No. |
|---|---|---|---|---|
| Can1_T1 15 stop | TTTA | UGUGU | GGCCCCAAATTCTAATTTCTAC**TGTGT**GTAGATTCCACACCTCTGACCAACGCTTTTTATTGGTATGATTGCCCTTGGTGGTACTATTGGTACAGGTCTTTTCATTGGATTATCCACACCTCTGTAAAACGCCGGCCCAGTGGGCGCTCTTATATCATATTTATTTATGGGTTCTTTGGCATCAATATACGCGCTCCTGCCC | SEQ ID No. 44 |
| Can1_Q1 58 stop | TTTC | UGUU | GGCCCCAAATTCTAATTTCTAC**TGTT**GTAGATACAGTTTTCTCACAAAGATTTTTTTCTGTCACGCAGTCCTTGGGTGAAATGGCTACATTCATCCCTGTTACATCCTCGTTCACAGTTTTCTCATAAAGATTCCTTTCTCCAGCATTTGGTGCGGCCAATGGTTACATGTATTGGTTTTCAATATACGCGCTCCTGCCC | SEQ ID No. 45 |
| Can1_Q1 58 stop | TTTC | UCUU | GGCCCCAAATTCTAATTTCTAC**TCTT**GTAGATACAGTTTTCTCACAAAGATTTTTTTCTGTCACGCAGTCCTTGGGTGAAATGGCTACATTCATCCCTGTTACATCCTCGTTCACAGTTTTCTCATAAAGATTCCTTTCTCCAGCATTTGGTGCGGCCAATGGTTACATGTATTGGTTTTCAATATACGCGCTCCTGCCC | SEQ ID No. 46 |
| Can1_Q1 58 stop | TTTC | UAUU | GGCCCCAAATTCTAATTTCTAC**TATT**GTAGATACAGTTTTCTCACAAAGATTTTTTTCTGTCACGCAGTCCTTGGGTGAAATGGCTACATTCATCCCTGTTACATCCTCGTTCACAGTTTTCTCATAAAGATTCCTTTCTCCAGCATTTGGTGCGGCCAATGGTTACATGTATTGGTTTTCAATATACGCGCTCCTGCCC | SEQ ID No. 47 |
| Can1_Q1 58 stop | TTTC | UAUU | GGCCCCAAATTCTAATTTCTAC**TGTGT**GTAGATACAGTTTTCTCACAAAGATTTTTTTCTGTCACGCAGTCCTTGGGTGAAATGGCTACATTCATCCCTGTTACATCCTCGTTCACAGTTTTCTCATAAAGATTCCTTTCTCCAGCATTTGGTGCGGCCAATGGTTACATGTATTGGTTTTCAATATACGCGCTCCTGCCC | SEQ ID No. 48 |
| Can1_I2 14 stop | TTTG | UGUU | GGCCCCAAATTCTAATTTCTAC**TGTT**GTAGATGGTAATTATCACAATAATGATTTTTCATTCAATTTTGGACGTACAAAGTTCCACTGGCGGCATGGATTAGTATTTGGAAGGTAATTATCACATAAATGAACTTGTTCCCTGTCAAATATTACGGTGAATTCGAGTTCTGGGTCGCCAATATACGCGCTCCTGCCC | SEQ ID No. 49 |
| Can1_I2 14 stop | TTTG | UCUU | GGCCCCAAATTCTAATTTCTAC**TCTT**GTAGATGGTAATTATCACAATAATGATTTTTCATTCAATTTTGGACGTACAAAGTTCCACTGGCGGCATGGATTAGTATTTGGAAGGTAATTATCACATAAATGAACTTGTTCCCTGTCAAATATTACGGTGAATTCGAGTTCTGGGTCGCCAATATACGCGCTCCTGCCC | SEQ ID No. 50 |
| Can1_I2 14 stop | TTTG | UAUU | GGCCCCAAATTCTAATTTCTAC**TATT**GTAGATGGTAATTATCACAATAATGATTTTTCATTCAATTTTGGACGTACAAAGTTCCACTGGCGGCATGGATTAGTATTTGGAAGGTAATTATCACATAAATGAACTTGTTCCCTGTCAAATATTACGGTGAATTCGAGTTCTGGGTCGCCAATATACGCGCTCCTGCCC | SEQ ID No. 51 |
| Can1_I2 14 stop | TTTG | UGUGU | GGCCCCAAATTCTAATTTCTAC**TGTGT**GTAGATGGTAATTATCACAATAATGATTTTTCATTCAATTTTGGACGTACAAAGTTCCACTGGCGGCATGGATTAGTATTTGGAAGGTAATTATCACATAAATGAACTTGTTCCCTGTCAAATATTACGGTGAATTCGAGTTCTGGGTCGCCAATATACGCGCTCCTGCCC | SEQ ID No. 52 |

The nuclease proteins were amplified by polymerase chain reaction with oligonucleotide primers to introduce an SV40 nuclear localization sequence at the N-terminus consisting of the DNA sequence ATGGCAC- CCAAGAAGAAGAGGAAGGTGTTA [SEQ ID No. 25] corresponding to a protein sequence of MAPKKKRKVL [SEQ ID NO. 26]. The resulting amplified DNA fragment (400 ng, purified) was then co-transformed along with a PsiI-linearized screening plasmid (250 ng) that already contained one of the above editing cassettes to assemble the complete editing plasmid by in vivo gap repair. Cells containing a repaired plasmid were selected for in yeast peptone-dextrose (YPD) containing 200 mg/L Geneticin for 3 days at 30° C. in a humidified shaking incubator. The resulting saturated culture was diluted 1:100 to 1:200 into synthetic complete yeast media lacking arginine and containing 50 mg/L of canavanine and grown overnight at 30° C. in a humidified shaking incubator. Because knockout of the Cant protein allows yeast to grow in the presence of the otherwise toxic analog canavanine, the relative OD600 of the overnight cultures is proportional to the rate of genome mutation induced by the transformed nuclease protein. Table 7 shows the results of in vivo *S. cerevisiae* editing:

TABLE 7

| Nuclease | Active in *S. cerevisiae* | crRNA loop | SEQ ID No. |
|---|---|---|---|
| MAD7 | Active | UGUU, UCUU | SEQ ID No. 1 |
| MAD7v1 | Active | UGUU | SEQ ID No. 3 |
| MAD7v2 | Active | UGUU | SEQ ID No. 4 |
| MAD7v3 | Active | UGUU | SEQ ID No. 5 |
| MAD7v4 | Active | UGUU | SEQ ID No. 6 |
| MAD2 | Weakly Active | UCUU | SEQ ID No. 7 |
| MAD4 | Weakly Active | UGUU | SEQ ID No. 9 |
| MAD6 | Inactive | | SEQ ID No. 11 |
| MAD31 | Active | UCUU | SEQ ID No. 13 |
| MAD41 | Active | UGUGU, UCUU | SEQ ID No. 15 |
| MAD44 | Active | UAUU, UCUU | SEQ ID No. 16 |
| MAD50 | Active | UCUU, UGUU | SEQ ID No. 17 |
| MAD53 | Active | UAUU | SEQ ID No. 18 |
| MAD54 | Active | UCUU | SEQ ID No. 19 |
| MAD57 | Active | UCUU | SEQ ID No. 20 |
| MAD82 | Active | UCUU, UGUU | SEQ ID No. 21 |
| MAD89 | Active | UCUU, UAUU | SEQ ID No. 22 |
| MAD92 | Weakly Active | UAUU | SEQ ID No. 24 |

Figure 4:
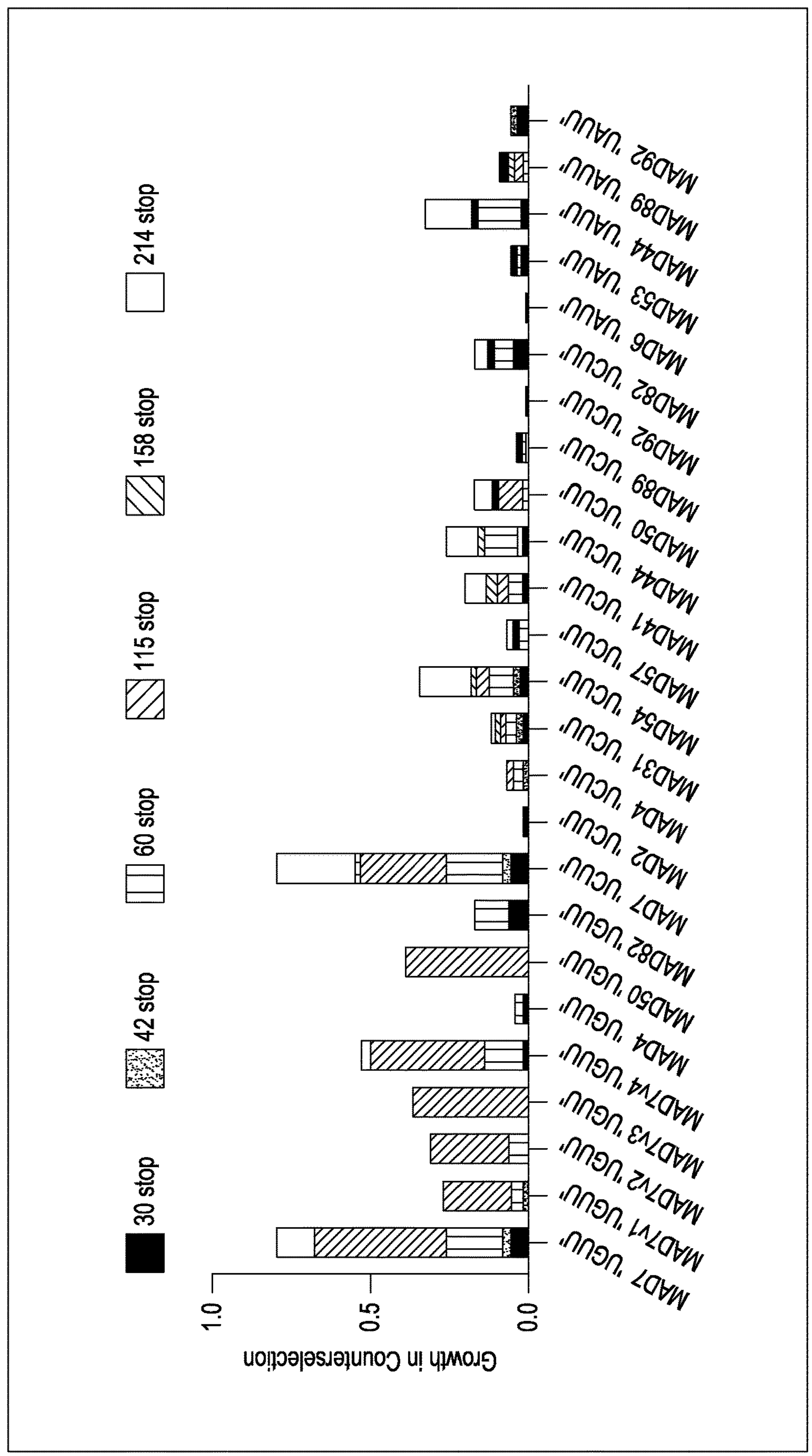
FIG. 4 shows the results of editing in *S. cerevisiae* as assessed by growth in canavanine-containing medium induced by precise edits in the Can1 locus using the indicated MAD-series nuclease with the indicated variable loop sequence.
Figure 5:
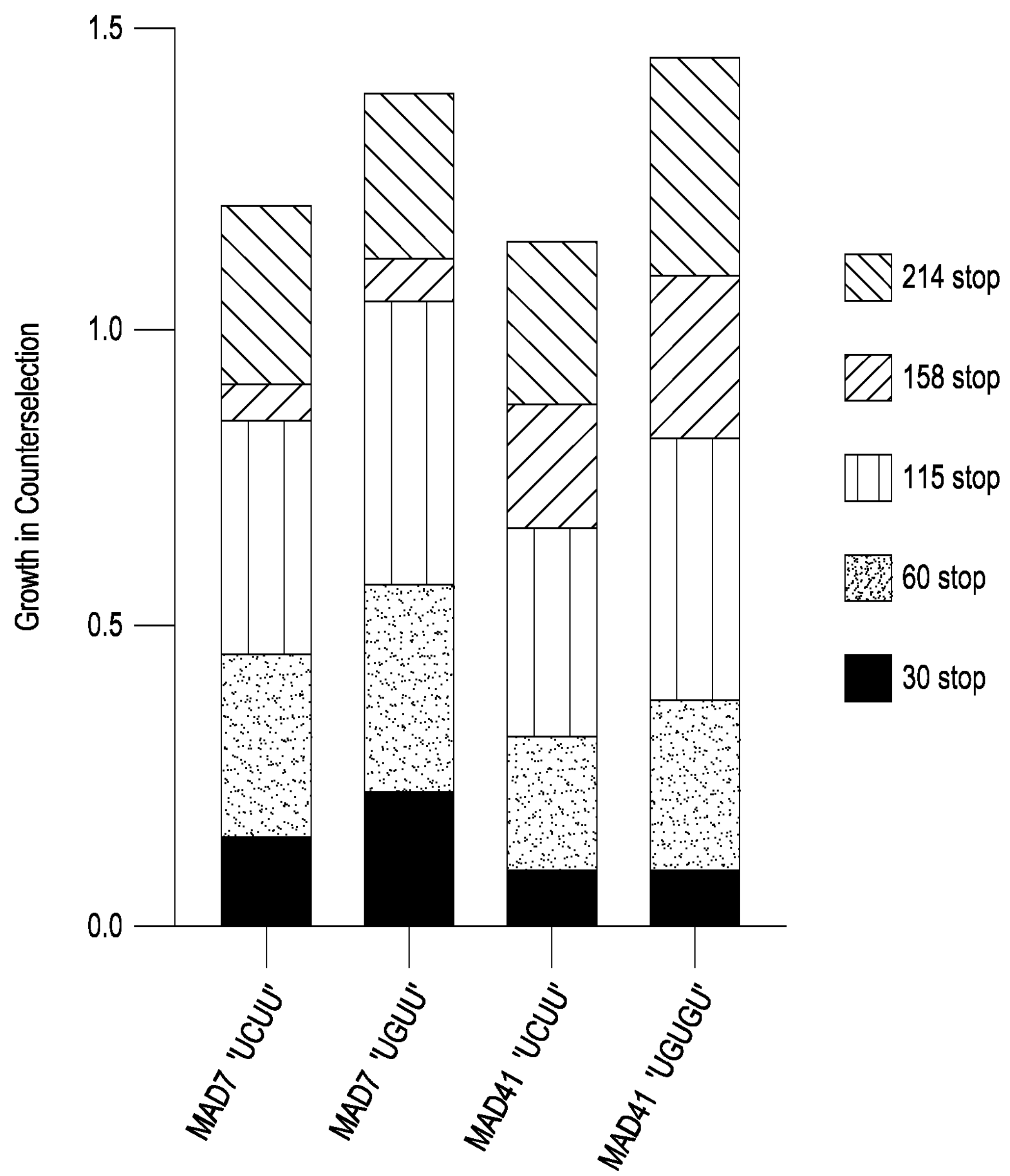
FIG. 5 shows the results of editing in *S. cerevisiae* by MAD7 and MAD41 using additional variable loop scaffolds.

FIG. 4 shows the results of in vivo editing of *S. cerevisiae* assessed by growth in canavanine-containing medium induced by precise edits in the Can1 locus using the indicated nuclease with the indicated variable loop sequence. FIG. 5 shows the results of in vivo editing of *S. cerevisiae* by MAD7 and MAD41 using additional variable loop scaffolds.

Example 7: Mammalian Cell Line Genome Editing

HEK293T cells were transfected in 96-well plates using 2 μL polyfect and 200 ng of each of the engine and editing plasmids. After 48 hours, the medium was aspirated and 100 μL of Taq lysis buffer with proteinase K (1 mg/mL final) was added (10× Taq lysis buffer: 100 mM Tris pH8, 500 mM NaCl, 15 mM $MgCL_2$, 1% Triton X-100). The cells were incubated at room temperature for 5 minutes and then transferred to a new 96-well plate. The cells were further incubated at 30 minutes at 56° C. and for 10 minutes at 98° C. 5 μL of lysate was used for PCR analysis.

Figure 6:
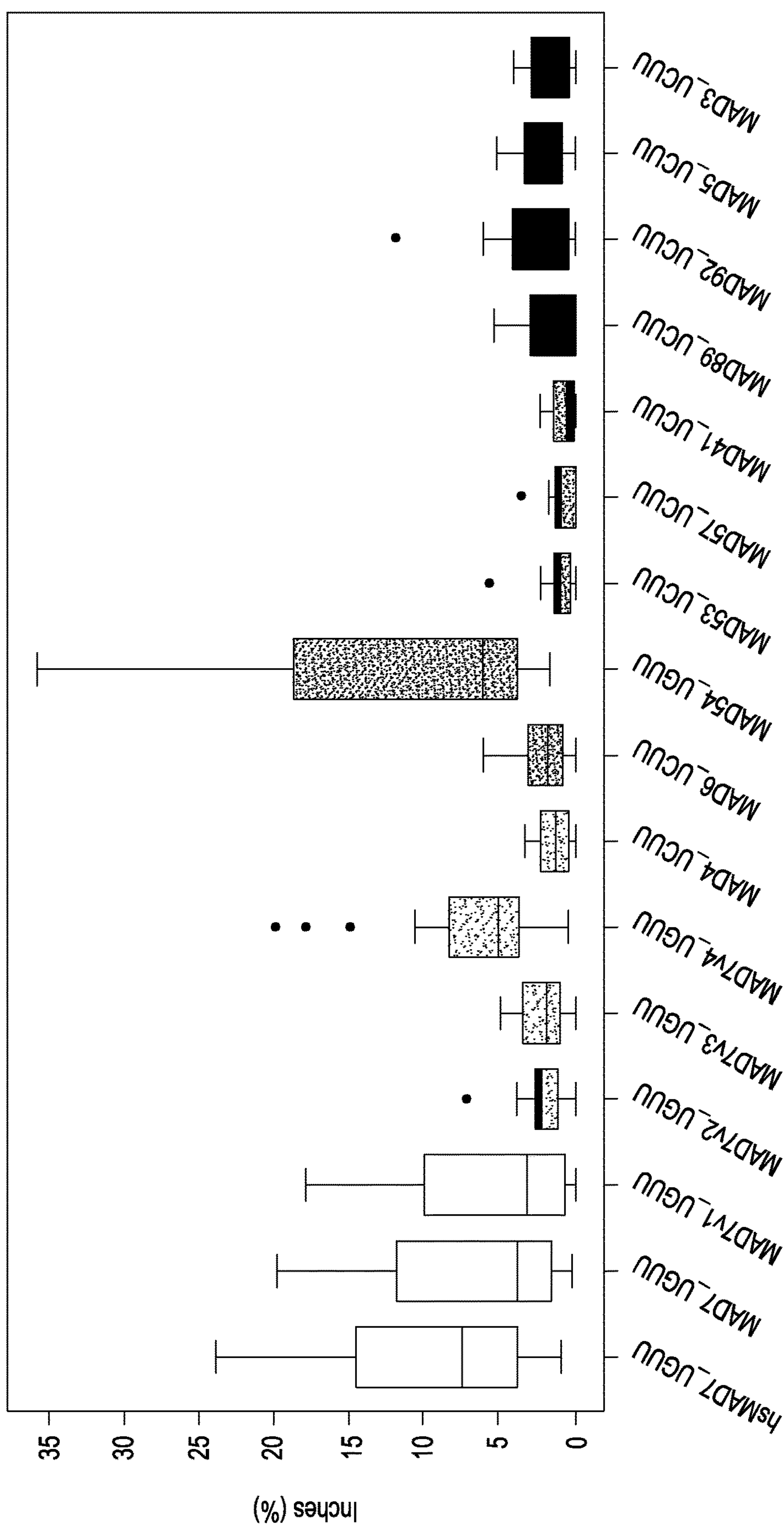
FIG. 6 shows the rate of indels induced by site-directed nuclease cleavage of HEK293T human cells induced by the indicated nuclease with the indicated variable loop.

FIG. 6 shows the rate of indels induced by site-directed nuclease cleavage in HEK293T human cells induced by the indicated nuclease with the indicated variable loop. hsMAD7 is the human codon-optimized nucleotide sequence [SEQ ID No. 53], while MAD7 indicates the broad-spectrum codon usage nucleotide sequence used in the *E. coli* and *S. cerevisiae* studies [SEQ ID No. 1].

TABLE 8

MAD7 Sequences

| Sequence and SEQ ID No. | Sequence | |
|---|---|---|
| MAD7 Native sequence Eubacterium rectale SEQ ID No. 1 | ATGAACAACG GCACAAATAA TTTTCAGAAC TTCATCGGGA TCTCAAGTTT GCAGAAAACG | 60 |
| | CTGCGCAATG CTCTGATCCC CACGGAAACC ACGCAACAGT TCATCGTCAA GAACGGAATA | 120 |
| | ATTAAAGAAG ATGAGTTACG TGGCGAGAAC CGCCAGATTC TGAAAGATAT CATGGATGAC | 180 |
| | TACTACCGCG GATTCATCTC TGAGACTCTG AGTTCTATTG ATGACATAGA TTGGACTAGC | 240 |
| | CTGTTCGAAA AAATGGAAAT TCAGCTGAAA AATGGTGATA ATAAAGATAC CTTAATTAAG | 300 |
| | GAACAGACAG AGTATCGGAA AGCAATCCAT AAAAAATTTG CGAACGACGA TCGGTTTAAG | 360 |
| | AACATGTTTA GCGCCAAACT GATTAGTGAC ATATTACCTG AATTTGTCAT CCACAACAAT | 420 |
| | AATTATTCGG CATCAGAGAA AGAGGAAAAA ACCCAGGTGA TAAAATTGTT TTCGCGCTTT | 480 |
| | GCGACTAGCT TTAAAGATTA CTTCAAGAAC CGTGCAAATT GCTTTTCAGC GGACGATATT | 540 |
| | TCATCAAGCA GCTGCCATCG CATCGTCAAC GACAATGCAG AGATATTCTT TTCAAATGCG | 600 |
| | CTGGTCTACC GCCGGATCGT AAAATCGCTG AGCAATGACG ATATCAACAA AATTTCGGGC | 660 |
| | GATATGAAAG ATTCATTAAA AGAAATGAGT CTGGAAGAAA TATATTCTTA CGAGAAGTAT | 720 |
| | GGGGAATTTA TTACCCAGGA AGGCATTAGC TTCTATAATG ATATCTGTGG GAAAGTGAAT | 780 |
| | TCTTTTATGA ACCTGTATTG TCAGAAAAAT AAAGAAAACA AAAATTTATA CAAACTTCAG | 840 |
| | AAACTTCACA AACAGATTCT ATGCATTGCG GACACTAGCT ATGAGGTCCC GTATAAATTT | 900 |
| | GAAAGTGACG AGGAAGTGTA CCAATCAGTT AACGGCTTCC TTGATAACAT TAGCAGCAAA | 960 |
| | CATATAGTCG AAAGATTACG CAAAATCGGC GATAACTATA ACGGCTACAA CCTGGATAAA | 1020 |
| | ATTTATATCG TGTCCAAATT TTACGAGAGC GTTAGCCAAA AAACCTACCG CGACTGGGAA | 1080 |
| | ACAATTAATA CCGCCCTCGA AATTCATTAC AATAATATCT TGCCGGGTAA CGGTAAAAGT | 1140 |
| | AAAGCCGACA AAGTAAAAAA AGCGGTTAAG AATGATTTAC AGAAATCCAT CACCGAAATA | 1200 |
| | AATGAACTAG TGTCAAACTA TAAGCTGTGC AGTGACGACA ACATCAAAGC GGAGACTTAT | 1260 |
| | ATACATGAGA TTAGCCATAT CTTGAATAAC TTTGAAGCAC AGGAATTGAA ATACAATCCG | 1320 |
| | GAAATTCACC TAGTTGAATC CGAGCTCAAA GCGAGTGAGC TTAAAAACGT GCTGGACGTG | 1380 |
| | ATCATGAATG CGTTTCATTG GTGTTCGGTT TTTATGACTG AGGAACTTGT TGATAAAGAC | 1440 |
| | AACAATTTTT ATGCGGAACT GGAGGAGATT TACGATGAAA TTTATCCAGT AATTAGTCTG | 1500 |
| | TACAACCTGG TTCGTAACTA CGTTACCCAG AAACCGTACA GCACGAAAAA GATTAAATTG | 1560 |
| | AACTTTGGAA TACCGACGTT AGCAGACGGT TGGTCAAAGT CCAAAGAGTA TTCTAATAAC | 1620 |
| | GCTATCATAC TGATGCGCGA CAATCTGTAT TATCTGGGCA TCTTTAATGC GAAGAATAAA | 1680 |
| | CCGGACAAGA AGATTATCGA GGGTAATACG TCAGAAAATA AGGGTGACTA CAAAAAGATG | 1740 |

TABLE 8-continued

MAD7 Sequences

| Sequence and SEQ ID No. | Sequence | |
|---|---|---|
| | ATTTATAATT TGCTCCCGGG TCCCAACAAA ATGATCCCGA AAGTTTTCTT GAGCAGCAAG | 1800 |
| | ACGGGGGTGG AAACGTATAA ACCGAGCGCC TATATCCTAG AGGGGTATAA ACAGAATAAA | 1860 |
| | CATATCAAGT CTTCAAAAGA CTTTGATATC ACTTTCTGTC ATGATCTGAT CGACTACTTC | 1920 |
| | AAAAACTGTA TTGCAATTCA TCCCGAGTGG AAAAACTTCG GTTTTGATTT TAGCGACACC | 1980 |
| | AGTACTTATG AAGACATTTC CGGGTTTTAT CGTGAGGTAG AGTTACAAGG TTACAAGATT | 2040 |
| | GATTGGACAT ACATTAGCGA AAAAGACATT GATCTGCTGC AGGAAAAAGG TCAACTGTAT | 2100 |
| | CTGTTCCAGA TATATAACAA AGATTTTTCG AAAAAATCAA CCGGGAATGA CAACCTTCAC | 2160 |
| | ACCATGTACC TGAAAAATCT TTTCTCAGAA GAAAATCTTA AGGATATCGT CCTGAAACTT | 2220 |
| | AACGGCGAAG CGGAAATCTT CTTCAGGAAG AGCAGCATAA AGAACCCAAT CATTCATAAA | 2280 |
| | AAAGGCTCGA TTTTAGTCAA CCGTACCTAC GAAGCAGAAG AAAAAGACCA GTTTGGCAAC | 2340 |
| | ATTCAAATTG TGCGTAAAAA TATTCCGGAA AACATTTATC AGGAGCTGTA CAAATACTTC | 2400 |
| | AACGATAAAA GCGACAAAGA GCTGTCTGAT GAAGCAGCCA AACTGAAGAA TGTAGTGGGA | 2460 |
| | CACCACGAGG CAGCGACGAA TATAGTCAAG GACTATCGCT ACACGTATGA TAAATACTTC | 2520 |
| | CTTCATATGC CTATTACGAT CAATTTCAAA GCCAATAAAA CGGGTTTTAT TAATGATAGG | 2580 |
| | ATCTTACAGT ATATCGCTAA AGAAAAAGAC TTACATGTGA TCGGCATTGA TCGGGGCGAG | 2640 |
| | CGTAACCTGA TCTACGTGTC CGTGATTGAT ACTTGTGGTA ATATAGTTGA ACAGAAAAGC | 2700 |
| | TTTAACATTG TAAACGGCTA CGACTATCAG ATAAAACTGA AACAACAGGA GGGCGCTAGA | 2760 |
| | CAGATTGCGC GGAAAGAATG GAAAGAAATT GGTAAAATTA AAGAGATCAA AGAGGGCTAC | 2820 |
| | CTGAGCTTAG TAATCCACGA GATCTCTAAA ATGGTAATCA AATACAATGC AATTATAGCG | 2880 |
| | ATGGAGGATT TGTCTTATGG TTTTAAAAAA GGGCGCTTTA AGGTCGAACG GCAAGTTTAC | 2940 |
| | CAGAAATTTG AAACCATGCT CATCAATAAA CTCAACTATC TGGTATTTAA AGATATTTCG | 3000 |
| | ATTACCGAGA ATGGCGGTCT CCTGAAAGGT TATCAGCTGA CATACATTCC TGATAAACTT | 3060 |
| | AAAAACGTGG GTCATCAGTG CGGCTGCATT TTTTATGTGC CTGCTGCATA CACGAGCAAA | 3120 |
| | ATTGATCCGA CCACCGGCTT TGTGAATATC TTTAAATTTA AAGACCTGAC AGTGGACGCA | 3180 |
| | AAACGTGAAT TCATTAAAAA ATTTGACTCA ATTCGTTATG ACAGTGAAAA AAATCTGTTC | 3240 |
| | TGCTTTACAT TTGACTACAA TAACTTTATT ACGCAAAACA CGGTCATGAG CAAATCATCG | 3300 |
| | TGGAGTGTGT ATACATACGG CGTGCGCATC AAACGTCGCT TTGTGAACGG CCGCTTCTCA | 3360 |
| | AACGAAAGTG ATACCATTGA CATAACCAAA GATATGGAGA AAACGTTGGA AATGACGGAC | 3420 |
| | ATTAACTGGC GCGATGGCCA CGATCTTCGT CAAGACATTA TAGATTATGA AATTGTTCAG | 3480 |
| | CACATATTCG AAATTTTCCG TTTAACAGTG CAAATGCGTA ACTCCTTGTC TGAACTGGAG | 3540 |
| | GACCGTGATT ACGATCGTCT CATTTCACCT GTACTGAACG AAAATAACAT TTTTTATGAC | 3600 |
| | AGCGCGAAAG CGGGGGATGC ACTTCCTAAG GATGCCGATG CAAATGGTGC GTATTGTATT | 3660 |
| | GCATTAAAAG GGTTATATGA AATTAAACAA ATTACCGAAA ATTGGAAAGA AGATGGTAAA | 3720 |
| | TTTTCGCGCG ATAAACTCAA AATCAGCAAT AAAGATTGGT TCGACTTTAT CCAGAATAAG | 3780 |
| | CGCTATCTCT AA | |
| MAD7 human codon optimized sequence SEQ ID No. 2 | ATGAATAATG GCACTAACAA CTTTCAGAAT TTCATAGGCA TCAGTAGTCT CCAAAAGACG | 60 |
| | TTGCGCAACG CACTTATTCC AACCGAGACA ACTCAACAGT TCATCGTGAA GAATGGGATT | 120 |
| | ATTAAAGAGG ACGAACTCCG AGGAGAGAAC CGGCAAATTC TTAAGGACAT CATGGACGAT | 180 |
| | TATTACAGAG GGTTTATTTC TGAGACATTA TCAAGTATTG ACGACATCGA CTGGACCTCA | 240 |
| | CTGTTCGAGA AGATGGAAAT TCAGTTGAAG AACGGAGACA ACAAGGACAC TCTAATCAAG | 300 |
| | GAACAAACAG AGTACCGGAA AGCTATACAT AAGAAGTTTG CCAATGATGA CCGGTTTAAG | 360 |
| | AACATGTTCT CCGCGAAACT CATCAGCGAC ATTCTGCCAG AATTCGTGAT CCACAACAAT | 420 |
| | AACTATTCAG CCTCTGAGAA GGAGGAAAAG ACCCAGGTCA TCAAGCTTTT CTCTAGATTC | 480 |
| | GCCACTAGCT TCAAGGACTA TTTCAAGAAC CGCGCCAATT GTTTCTCTGC TGACGATATC | 540 |
| | TCCAGCAGCA GTTGCCATAG GATCGTGAAC GACAATGCTG AAATCTTCTT CTCTAATGCC | 600 |
| | CTTGTATACA GACGGATCGT GAAGTCACTG AGCAATGATG ACATTAACAA GATAAGCGGT | 660 |
| | GATATGAAAG ATAGTCTCAA GGAAATGTCA CTCGAAGAAA TTTATAGCTA CGAGAAATAC | 720 |
| | GGAGAGTTCA TCACCCAGGA GGGAATCAGT TTCTACAACG ATATTTGTGG CAAGGTAAAC | 780 |
| | TCCTTCATGA ATCTATATTG CCAGAAAAAC AAGGAGAATA AGAATCTTTA TAAGCTGCAG | 840 |
| | AAGTTACATA AGCAGATCCT GTGTATTGCA GATACCTCCT ATGAAGTGCC ATATAAGTTT | 900 |
| | GAGTCTGACG AGGAAGTGTA TCAATCCGTA AATGGGTTCC TCGACAACAT CAGCTCTAAG | 960 |
| | CATATAGTTG AACGACTTAG AAAGATAGGC GACAACTATA ATGGCTACAA CCTCGACAAG | 1020 |
| | ATTTATATAG TGTCCAAATT CTACGAGTCC GTATCCCAAA AGACATACAG AGATTGGGAA | 1080 |
| | ACAATCAATA CAGCCCTCGA AATCCACTAC AATAATATCC TACCCGGCAA TGGGAAATCC | 1140 |
| | AAGGCAGATA AGGTAAAGAA GGCAGTCAAG AACGACCTCC AGAAGTCCAT CACCGAGATT | 1200 |
| | AACGAACTGG TGAGCAATTA CAAACTCTGT AGTGACGATA ATATCAAGGC TGAGACGTAC | 1260 |
| | ATCCATGAGA TTTCACACAT ATTGAACAAC TTCGAAGCAC AGGAACTGAA GTACAATCCG | 1320 |
| | GAAATTCATC TCGTAGAATC CGAGCTTAAA GCCAGCGAGC TTAAGAACGT GCTCGATGTG | 1380 |
| | ATTATGAACG CGTTTCACTG GTGTAGTGTC TTCATGACTG AAGAATTAGT TGACAAGGAC | 1440 |
| | AACAATTTCT ATGCCGAACT GGAAGAAATT TACGATGAGA TCTATCCTGT TATCAGTCTG | 1500 |
| | TATAACCTCG TACGGAACTA TGTGACCCAG AAGCCCTACT CGACCAAAAA GATCAAACTG | 1560 |
| | AACTTCGGCA TTCCAACCCT GGCCGATGGA TGGAGCAAAT CCAAAGAGTA CTCTAATAAC | 1620 |
| | GCTATCATTC TCATGCGAGA CAATCTCTAC TATCTCGGAA TATTCAATGC AAAGAATAAA | 1680 |
| | CCAGACAAAA AGATTATTGA AGGGAACACA TCCGAGAACA AAGGTGATTA TAAGAAAATG | 1740 |
| | ATTTACAACC TGCTTCCAGG GCCCAATAAG ATGATTCCCA AGGTCTTTCT TTCAAGCAAG | 1800 |
| | ACTGGAGTTG AGACTTACAA GCCGTCCGCA TACATTCTCG AGGGCTATAA GCAGAACAAG | 1860 |
| | CACATTAAGA GCAGTAAAGA CTTCGATATC ACTTTCTGCC ATGATCTCAT TGACTACTTT | 1920 |
| | AAGAATTGTA TCGCTATTCA TCCGGAATGG AAGAACTTTG GATTTGACTT CAGCGATACA | 1980 |
| | AGTACCTACG AGGATATCTC TGGGTTCTAC CGGGAAGTGG AACTTCAGGG ATACAAGATC | 2040 |
| | GACTGGACAT ATATCTCTGA GAAAGACATC GATCTGCTGC AGGAGAAAGG CCAGCTGTAC | 2100 |
| | CTGTTCCAGA TTTATAATAA AGATTTCTCA AAGAAGAGCA CAGGAAACGA TAATCTTCAT | 2160 |
| | ACTATGTATC TGAAGAATCT CTTCTCCGAA GAGAACCTGA AGGATATCGT CCTCAAACTG | 2220 |
| | AACGGAGAAG CCGAGATTTT CTTCAGGAAG AGTAGTATTA AGAATCCCAT TATTCATAAG | 2280 |
| | AAAGGCTCCA TCTTGGTTAA CCGCACTTAC GAGGCTGAAG AGAAGGACCA GTTTGGAAAT | 2340 |

TABLE 8-continued

MAD7 Sequences

| Sequence and SEQ ID No. | Sequence | |
|---|---|---|
| | ATCCAAATCG TGAGGAAGAA TATTCCAGAG AATATCTACC AGGAACTGTA TAAGTACTTT | 2400 |
| | AATGATAAGA GCGATAAAGA ACTGAGCGAC GAGGCAGCGA AGTTGAAGAA TGTGGTGGGC | 2460 |
| | CATCACGAAG CTGCCACAAA CATTGTGAAA GACTATAGGT ACACATATGA TAAATACTTT | 2520 |
| | CTGCATATGC CTATAACCAT AAATTTCAAG GCCAATAAGA CTGGGTTCAT TAATGACCGC | 2580 |
| | ATCCTGCAGT ACATCGCTAA GGAGAAGGAC CTGCACGTCA TAGGGATCGA CCGCGGTGAA | 2640 |
| | CGGAATTTGA TTTATGTGTC CGTTATCGAT ACCTGCGGGA ATATCGTGGA GCAAAAGAGC | 2700 |
| | TTTAATATCG TCAATGGATA CGACTACCAG ATCAAGTTAA AGCAGCAAGA AGGCGCCAGG | 2760 |
| | CAAATCGCCA GGAAAGAGTG GAAAGAGATC GGCAAGATAA AGGAAATTAA GGAAGGCTAC | 2820 |
| | CTTTCCCTGG TCATCCATGA AATTAGTAAG ATGGTCATTA AGTACAATGC CATCATAGCA | 2880 |
| | ATGGAAGACT TAAGTTACGG ATTTAAGAAG GGAAGATTCA AAGTGGAAAG GCAGGTGTAT | 2940 |
| | CAGAAGTTTG AAACGATGCT AATAAACAAA CTTAATTATC TTGTGTTCAA AGACATTAGC | 3000 |
| | ATCACAGAGA ATGGAGGGCT TCTCAAGGGA TACCAACTGA CCTACATCCC AGATAAGCTT | 3060 |
| | AAGAACGTTG GCCACCAATG CGGCTGCATA TTCTACGTCC CGGCTGCTTA CACTTCTAAG | 3120 |
| | ATCGATCCAA CCACCGGCTT TGTGAATATC TTTAAGTTTA AAGACTTGAC CGTGGATGCT | 3180 |
| | AAGCGCGAGT TCATCAAGAA GTTTGACAGC ATCAGGTACG ACTCAGAAAA GAACCTCTTC | 3240 |
| | TGTTTCACAT TCGATTATAA CAACTTTATT ACTCAGAATA CTGTCATGAG TAAGTCATCC | 3300 |
| | TGGTCAGTGT ATACCTACGG AGTGAGGATC AAGCGAAGGT TTGTGAACGG CAGGTTTAGT | 3360 |
| | AATGAGTCTG ACACAATCGA TATTACCAAA GACATGGAGA AAACACTGGA GATGACAGAC | 3420 |
| | ATCAACTGGA GGGATGGACA TGACCTGCGC CAGGATATCA TAGATTACGA GATCGTGCAA | 3480 |
| | CATATATTCG AAATCTTTAG GCTGACAGTG CAGATGCGCA ACTCCCTGAG CGAGCTCGAA | 3540 |
| | GACAGAGATT ATGATAGACT AATCAGTCCG GTTCTGAACG AGAACAATAT CTTCTACGAT | 3600 |
| | AGTGCTAAGG CAGGAGACGC GCTGCCCAAG GACGCAGATG CCAATGGCGC GTATTGCATT | 3660 |
| | GCACTTAAAG GACTGTACGA AATTAAGCAG ATTACCGAGA ACTGGAAGGA GGACGGCAAG | 3720 |
| | TTTAGCAGGG ATAAGCTGAA GATTAGTAAC AAAGATTGGT TTGACTTTAT ACAGAATAAG | 3780 |
| | CGTTATCTGT AA | 3792 |

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, 916.

We claim:

1. A coding sequence for a nucleic acid-guided nuclease comprising a nucleic acid sequence of any of SEQ ID Nos. 20, 21, 22 or 24.

2. The coding sequence for the nucleic acid-guided nuclease of claim 1 comprising the nucleic acid sequence SEQ ID No. 20.

3. The coding sequence for the nucleic acid-guided nuclease of claim 2, wherein a compatible guide RNA to the nucleic-acid-guided nuclease has an optimal crRNA variable loop comprising UCUU.

4. The coding sequence for the nucleic acid-guided nuclease of claim 1 comprising the nucleic acid sequence SEQ ID No. 21.

5. The coding sequence for the nucleic acid-guided nuclease of claim 4, wherein a compatible guide RNA to the nucleic-acid-guided nuclease has an optimal crRNA variable loop comprising UCUU or UGUU.

6. The coding sequence for the nucleic acid-guided nuclease of claim 1 comprising the nucleic acid sequence SEQ ID No. 22.

7. The coding sequence for the nucleic acid-guided nuclease of claim 6, wherein a compatible guide RNA to the nucleic-acid-guided nuclease has an optimal crRNA variable loop comprising UCUU or UAUU.

8. The coding sequence for the nucleic acid-guided nuclease of claim 1 comprising the nucleic acid sequence SEQ ID No. 24.

9. The coding sequence for the nucleic acid-guided nuclease of claim 8, wherein a compatible guide RNA to the nucleic-acid-guided nuclease has an optimal crRNA variable loop comprising UAUU.

10. The coding sequence for a nucleic acid-guided nuclease of claim 1 for editing in bacteria.

11. The coding sequence for a nucleic acid-guided nuclease of claim 1 for editing in yeast.

12. The coding sequence for a nucleic acid-guided nuclease of claim 1 for editing in isolated mammalian cells.

* * * * *